United States Patent
DeMarco et al.

(10) Patent No.: US 11,752,190 B2
(45) Date of Patent: *Sep. 12, 2023

(54) MODULATORS OF COMPLEMENT ACTIVITY

(71) Applicant: Ra Pharmaceuticals, Inc., Cambridge, MA (US)

(72) Inventors: Steven James DeMarco, Boxford, MA (US); Michelle Denise Hoarty, Billerica, MA (US); Grace Victoria Parker, Somerville, MA (US); Alonso Ricardo, Winchester, MA (US); Sylvia Tobe, Winchester, MA (US); Douglas A. Treco, Arlington, MA (US)

(73) Assignee: Ra Pharmaceuticals, Inc., Cambridge, MA (US)

( * ) Notice: Subject to any disclaimer, the term of this patent is extended or adjusted under 35 U.S.C. 154(b) by 323 days.

This patent is subject to a terminal disclaimer.

(21) Appl. No.: 17/065,560

(22) Filed: Oct. 8, 2020

(65) Prior Publication Data

US 2021/0077572 A1 Mar. 18, 2021

Related U.S. Application Data

(63) Continuation of application No. 16/062,653, filed as application No. PCT/US2016/065228 on Dec. 7, 2016, now Pat. No. 10,835,574.

(60) Provisional application No. 62/347,486, filed on Jun. 8, 2016, provisional application No. 62/331,320, filed on May 3, 2016, provisional application No. 62/268,360, filed on Dec. 16, 2015.

(51) Int. Cl.
*A61K 38/12* (2006.01)
*A61K 9/00* (2006.01)
*A61P 7/00* (2006.01)
*A61P 37/02* (2006.01)

(52) U.S. Cl.
CPC ............ *A61K 38/12* (2013.01); *A61K 9/0019* (2013.01); *A61P 7/00* (2018.01); *A61P 37/02* (2018.01)

(58) Field of Classification Search
None
See application file for complete search history.

(56) References Cited

U.S. PATENT DOCUMENTS

| | | |
|---|---|---|
| 4,033,940 A | 7/1977 | Hughes |
| 4,179,337 A | 12/1979 | Davis |
| 4,216,141 A | 8/1980 | Rivier |
| 4,271,068 A | 6/1981 | Kamber |
| 4,301,144 A | 11/1981 | Iwashita |
| 4,496,689 A | 1/1985 | Mitra |
| 4,640,835 A | 2/1987 | Shimizu |
| 4,670,417 A | 6/1987 | Iwasaki |
| 4,791,192 A | 12/1988 | Nakagawa |
| 5,270,170 A | 12/1993 | Schatz |
| 5,338,665 A | 8/1994 | Schatz |
| 5,371,109 A | 12/1994 | Engstroem |
| 5,427,908 A | 6/1995 | Dower |
| 5,580,717 A | 12/1996 | Dower |
| 5,585,353 A | 12/1996 | Merrifield |
| 5,591,828 A | 1/1997 | Bosslet |
| 5,596,078 A | 1/1997 | Andersson |
| 5,618,676 A | 4/1997 | Hitzeman |
| 5,643,768 A | 7/1997 | Kawasaki |
| 5,658,754 A | 8/1997 | Kawasaki |
| 5,726,287 A | 3/1998 | Andersson |
| 5,750,344 A | 5/1998 | Doyle |
| 5,766,897 A | 6/1998 | Braxton |
| 5,824,784 A | 10/1998 | Kinstler |
| 5,834,318 A | 11/1998 | Buettner |
| 5,837,500 A | 11/1998 | Ladner |
| 5,843,701 A | 12/1998 | Gold |
| 5,854,018 A | 12/1998 | Hitzeman |
| 5,856,123 A | 1/1999 | Hitzeman |
| 5,919,651 A | 7/1999 | Hitzeman |
| 5,922,680 A | 7/1999 | Fjellestad-Paulsen |
| 5,990,237 A | 11/1999 | Bentley |
| 5,990,273 A | 11/1999 | Andersson |
| 6,086,918 A | 7/2000 | Stern |
| 6,194,550 B1 | 2/2001 | Gold |
| 6,242,565 B1 | 6/2001 | Kishida |
| 6,258,558 B1 | 7/2001 | Szostak |
| 6,261,804 B1 | 7/2001 | Szostak |
| 6,268,343 B1 | 7/2001 | Knudsen |
| 6,309,669 B1 | 10/2001 | Setterstrom |

(Continued)

FOREIGN PATENT DOCUMENTS

| | | |
|---|---|---|
| EP | 3154561 | 4/2017 |
| JP | 2013543380 | 12/2013 |

(Continued)

OTHER PUBLICATIONS

Anonymous. "Formulation" cambridgemedconsulting.com/resources/formulation.html (Year: 2012).*
Ricklin, Daniel et al. "Complement in Immune and Inflammatory Disorders: Pathophysiological Mechanisms" J. Immunol. 190: 3831-3838. (Year: 2013).
Ricardo et al. "Preclinical evaluation of RA 101495, a potent cyclic peptide inhibitor of C5 for the treatment of paroxysmal nocturnal hemoglobinuria" ASH Meeting 2015, Abstract #939 (Year: 2015).
Morgan, Paul et al. "Complement, a target for therapy in inflammatory and degenerative diseases" Nature Reviews Drug Discovery 14:857-877. (Year: 2015).

(Continued)

*Primary Examiner* — Sudhakar Katakam
*Assistant Examiner* — Zachary J Miknis
(74) *Attorney, Agent, or Firm* — Glenn J. Foulds; Fenwick & West LLP

(57) ABSTRACT

The present invention relates to polypeptide modulators of complement activity, including cyclic polypeptide modulators. Included are methods of utilizing such modulators as therapeutics.

18 Claims, 20 Drawing Sheets

Specification includes a Sequence Listing.

(56) References Cited

U.S. PATENT DOCUMENTS

| | | |
|---|---|---|
| 6,348,584 B1 | 2/2002 | Hodgson |
| 6,355,245 B1 | 3/2002 | Evans |
| 6,361,943 B1 | 3/2002 | Yanagawa |
| 6,673,901 B2 | 1/2004 | Koide |
| 6,716,973 B2 | 4/2004 | Baskerville |
| 6,720,472 B2 | 4/2004 | Chada |
| 6,844,010 B1 | 1/2005 | Setterstrom |
| 6,962,781 B1 | 11/2005 | Williams |
| 7,348,401 B2 | 3/2008 | Johnson |
| 7,744,910 B2 | 6/2010 | Gschneidner |
| 8,101,586 B2 | 1/2012 | Rock |
| 8,329,169 B2 | 12/2012 | Fung |
| 8,377,437 B2 | 2/2013 | Van Lookeren Campagne |
| 8,652,477 B2 | 2/2014 | Schwaeble |
| 8,703,136 B2 | 4/2014 | Baas |
| 8,753,625 B2 | 6/2014 | Fung |
| 8,911,733 B2 | 12/2014 | Holers |
| 9,937,222 B2 | 4/2018 | Hoarty |
| 10,106,579 B2 * | 10/2018 | Hoarty ............... A61K 47/64 |
| 10,208,089 B2 | 2/2019 | Hoarty |
| 10,328,115 B2 * | 6/2019 | Hoarty ............... A61P 31/00 |
| 10,435,438 B2 | 10/2019 | Hoarty |
| 10,588,936 B2 * | 3/2020 | Hoarty ............... A61P 37/06 |
| 10,835,574 B2 * | 11/2020 | DeMarco ............. A61P 7/00 |
| 11,123,399 B2 * | 9/2021 | Ricardo ............... G01N 33/68 |
| 2003/0040472 A1 | 2/2003 | Larsen |
| 2005/0191343 A1 | 9/2005 | Liang |
| 2006/0270590 A1 | 11/2006 | Lockwood |
| 2008/0146490 A1 | 6/2008 | Joabsson |
| 2008/0269318 A1 | 10/2008 | Romano |
| 2008/0313749 A1 | 12/2008 | Timmerman |
| 2009/0054623 A1 | 2/2009 | Defrees |
| 2010/0015139 A1 | 1/2010 | Bansal |
| 2010/0093624 A1 | 4/2010 | Low |
| 2010/0099113 A1 | 4/2010 | Sebastian |
| 2010/0143344 A1 | 6/2010 | Baas |
| 2010/0166748 A1 | 7/2010 | Guild |
| 2011/0172126 A1 | 7/2011 | Brust |
| 2011/0190221 A1 | 8/2011 | Francois |
| 2011/0269807 A1 | 11/2011 | Baciu |
| 2012/0225056 A1 | 9/2012 | Rother |
| 2013/0029912 A1 | 1/2013 | Holers |
| 2013/0053302 A1 | 2/2013 | Lambris |
| 2013/0053311 A1 | 2/2013 | Kalthoff |
| 2013/0246083 A1 | 9/2013 | Bell |
| 2013/0273052 A1 | 10/2013 | Gies |
| 2013/0344082 A1 | 12/2013 | Lambris |
| 2013/0345257 A1 | 12/2013 | Hahn |
| 2014/0234275 A1 | 8/2014 | Williams |
| 2015/0011474 A1 | 1/2015 | Berghard |
| 2015/0057342 A1 | 2/2015 | Koren |
| 2015/0166606 A1 | 6/2015 | Wang |
| 2015/0359900 A1 | 12/2015 | Wang |
| 2016/0206580 A1 | 7/2016 | Los |
| 2016/0376355 A1 | 12/2016 | Bell |
| 2017/0137468 A1 | 5/2017 | Arata |
| 2018/0280530 A1 | 10/2018 | Guo |

FOREIGN PATENT DOCUMENTS

| | | |
|---|---|---|
| RU | 2406507 | 12/2010 |
| RU | 2505311 | 1/2014 |
| RU | 2014137303 | 4/2016 |
| WO | 1993011161 | 6/1993 |
| WO | 9832427 | 7/1998 |
| WO | 1998032427 | 7/1998 |
| WO | 2000021559 | 4/2000 |
| WO | 2005023866 | 3/2005 |
| WO | 2006088888 | 8/2006 |
| WO | 2008113834 A2 | 9/2008 |
| WO | 2009014633 | 1/2009 |
| WO | 2009046198 | 4/2009 |
| WO | 2009067191 | 5/2009 |
| WO | 2011057158 | 5/2011 |
| WO | 2012044893 | 4/2012 |
| WO | 2012139081 | 11/2012 |
| WO | 2012162215 | 11/2012 |
| WO | 2012174055 | 12/2012 |
| WO | 2013037267 | 3/2013 |
| WO | 2013052736 | 4/2013 |
| WO | 2013126006 | 8/2013 |
| WO | 2013172954 | 11/2013 |
| WO | 2014078622 | 5/2014 |
| WO | 2015140304 | 9/2015 |
| WO | 2015191951 | 12/2015 |
| WO | 2016094834 | 6/2016 |
| WO | 2016123371 | 8/2016 |
| WO | 2017035362 | 3/2017 |
| WO | 2017105939 | 6/2017 |
| WO | 2017105939 A1 | 6/2017 |
| WO | 2018106859 | 6/2018 |
| WO | 2018106859 A1 | 6/2018 |
| WO | 2019051436 | 3/2019 |
| WO | 2019112984 | 6/2019 |
| WO | 2020185541 | 9/2020 |
| WO | 2020219822 | 10/2020 |

OTHER PUBLICATIONS

Rapharma: "Zilucoplan in Generalized Myasthenia Gravis", dated Dec. 10, 2018 URL:https://rapharma.com/wp-content/upload s/2018/12/Zilucoplan-in-Generalized-Myasth enia-Gravis-1.pdf.

Extended European Search Report for corresponding European Application No. 18788604.9 dated Apr. 15, 2021.

Anonymous: "History of Changes for Study: NCT04382755" May 8, 2020, XP055809235, Retrieved from the Internet: URL:https://www.clinicaltrials.gov/ct2/history/NCT04382755?V_I=View#StudyPageTop [retrieved on May 31, 2021] the whole document.

Declercq et al: "Zilucoplan in patients with acute hypoxic respiratory failure due to COVID-19 (Zilucov): A structured summary of a study protocol for a randomised controlled trial", Trials, vol. 21, No. 1, Dec. 1, 2020.

Diurno et al: "Eculizumab treatment in patients with COVID-19: preliminary results from real life ASL Napoli 2 Nord experience", Apr. 1, 2020 (Apr. 1, 2020).

Sorbera et al: "Taking aim at a fast-moving target: targets to watch for SARS-CoV-2 and COVID-19", Drugs of the Future, vol. 45, No. 4, Jan. 1, 2020.

Sun et al: Treatment With Anti-C5a Antibody Improves the Outcome of H7N9 Virus Infection in African Green Monkeys11 , Clinical Infectious Diseases, vol. 60, No. 4, Nov. 27, 2014.

Jiang et al: "Blockade of the C5a-C5aR axis alleviates lung damage in hDPP4-transgenic mice infected with MERS-CoV" , Emerging Microbes & Infections, vol. 7, No. 1, Apr. 24, 2018.

Howard et al: "Clinical Effects of the Self-administered Subcutaneous Complement Inhibitor Zilucoplan in Patients With Moderate to Severe Generalized Myasthenia Gravis: Results of a Phase 2 Randomized, Double-Blind, Placebo-Controlled, Multicenter Clinical Trial", JAMA Neurology, vol. 77. No. 5. Feb. 17, 2020.

Hillmen, P. et al. (2006) "The Complement Inhibitor Eculizumab in Paroxysmal Nocturnal Hemoglobinuria" The New England Journal of Medicine, 355(12):1233-1243.

Legendre, C.M. et al. (2013) "Terminal Complement Inhibitor Eculizumab in Atypical Hemolytic-Uremic Syndrome" The New England Journal of Medicine, 368(23):2169-2181.

International Search Report and Written Opinion in application No. PCT/US2019/057316 entitled "Neurological Disease Treatment With Complement Inhibitors" dated Apr. 2, 2020.

Jefffrey Johnston "A Phase 1 Multiple-Dose Clinical Study of RA101495, a Subcutaneously Administered Synthetic Macrocyclic Peptide Inhibitor of Complement C5 for Treatment of Paroxysmal Nocturnal Hemoglobinuria" Library of the European Hematology Association, 2016, XP055661443.

Howard, James F. et al: "Safety and efficacy of eculizumab in anti-acetylcholine receptor antibody-positive refractory generalised myasthenia gravis (REGAIN): a phase 3, randomised, double-blind, placebo-controlled, multicentre study", Lancet Neurology, vol. 16, No. 12, 2017, pp. 976-986, XP085267220.

(56) References Cited

OTHER PUBLICATIONS

US National Library of Medicine: "Phase 2 Safety and Efficacy Study of RA101495 to Treat PNH Patients", Mar. 8, 2017 (Mar. 8, 2017), XP055661467.
Ra Pharmaceuticals, Inc., Statistical Analysis Plan, RA101495-01.201: A Phase 2 Multicenter, Open-Label, Uncontrolled Study to Evaluate the Safety, Tolerability, Efficacy, Pharmacokinetics, and Pharmacodynamics of RA101495 in Subjects With Paroxysmal Nocturnal Hemoglobinuria.
Ra Pharmaceuticals, Inc., Protocol, RA101495-01.201: A Phase 2 Multicenter, Open-Label, Uncontrolled Study to Evaluate the Safety, Tolerability, Efficacy, Pharmacokinetics, and Pharmacodynamics of RA101495 in Subjects With Paroxysmal Nocturnal Hemoglobinuria.
Extended European Search Report for corresponding European Application No. 20157916.6 entitled "Modulators of Complement Activity" dated May 13, 2020.
International Search Report and Written Opinion dated Sep. 3, 2020 in PCT Application No. PCT/US2020/021330 entitled "Modulators of Complement Activity".
Freskgard, Per-Ola et al. "Antibody therapies in CNS diseases", Neuropharmacology, Pergamon Press, Oxford, GB, vol. 120, Mar. 10, 2016.
Johnston, Jeffrey et al. "A Phase 1 Single-Ascending-Dose Clinical Study of RA101495, a Subcutaneously Administered Synthetic Macrocyclic Peptide Inhibitor of Complement C5 for Treatment of Paroxysmal Nocturnal Hemoglobinuria" 2016, XP055697141, Retrieved from the Internet: URL:https://rapharma.com/wp-content/uploads/2018/12/9-Ra-Pharma-EHA-2016-RA101495-SAD-Poster.pdf.
Korean Office Action for corresponding Korean Application No. 10-2019-7014115 dated Aug. 14, 2020.
Mexican Office Action for corresponding Mexican Application No. MX/a/2016/016449 dated Jul. 20, 2020.
Huber-Lang, et al., (2006) Generation of C5a in the absence of C3: a new complement activation pathway. Nature Med. 12(6):682-687.
Krisinger, et al., (2014) Thrombin generates previously unidentified C5 products that support the terminal complement activation pathway. Blood. 120(8):1717-1725.
Rittirsch, et al., (2012) Role of complement in multiorgan failure. Clin Dev Immunol, 2012:962927.
Vogt, (1999) Cleavage of the fifth component of complement and generation of a functionally active C5b6-like complex by human leukocyte elastase. Immunobiology. 201:470-477.
Risitano et al., (2012) The complement receptor 2/factor H fusion protein TT30 protects paroxysmal nocturnal hemoglobinuria erythrocytes from complement-mediated hemolysis and C3 fragment Blood 119(6): 6307-16.
Thomas et al., (1996) Inhibition of complement activity by humanized anti-C5 antibody and single-chain Fv. Molecular Immunology. 33(17-18):1389-401.
Banks, P. et al., (2000) Impact of a red-shifted dye label for high throughput fluorescence polarization assays of G protein-coupled receptors. J Biomol Screen. 5(5):329-34.
De Boer J.P., et al., (1993) Activation patterns of coagulation and fibrinolysis in baboons following infusion with lethal or sublethal dose of *Escherichia coli*. Circulatory shock 39, 59-67.
Levi, M. et al., (2013) Sepsis and thrombosis. Seminars in thrombosis and hemostasis 39, 559-66.
Molines, T. E. et al., (2002) Essential role of the C5a receptor in *E coli*-induced oxidative burst and phagocytosis revealed by a novel lepirudin-based human whole blood model of inflammation. Blood 100, 1869-1877.
Nishimura, J. et al., (2014) Genetic variants in C5 and poor response to eculizumab. N Engl J Med. 370: 632-9.
Parker, C. et al.,(2005) Diagnosis and management of paroxysmal nocturnal hemoglobinuria. Blood. 106: 3699-709.
Parker, C.J., (2007) The pathophysiology of paroxysmal nocturnal hemoglobinuria. Exp Hematol. 35: 523-33.
Parker, C.J., (2012) Paroxysmal nocturnal hemoglobinuria. Curr Opin Hematol. 19:141-8.
Rittirsch D., et al., (2008) Harmful molecular mechanisms in sepsis. Nature Reviews Immunology 8, 776-87.
Schrezenmeier, H. et al., (2014) Baseline characteristics and disease burden in patients in the International Paroxysmal Nocturnal Hemoglobinuria Registry. Haematologica. 99: 922-9.
Abuchowski, A. et al, (1977) Effect of covalent attachment of polyethylene glycol on immunogenicity and circulating life of bovine liver catalase, J. Biol. Chem., 252, 3582.
Baskerville, S. and Bartel, D.P. (2002) A ribozyme that ligates RNA to protein, Proc. Natl. Acad. Sci. USA 99:9154-9159.
Beauchamp C. O. et al., (1983) A new procedure for the synthesis of polyethylene glycol-protein adducts; effects on function, receptor recognition, and clearance of superoxide dismutase, lactoferrin, and alpha 2-macroglobulin, Anal. Biochem., 131, 25.
Bergseth, G. et al., (2013) An international serum standard for application in assays to detect human complement activation products. Mol Immunol. 56:232-9.
Blackwell, H. E. and Grubbs, R. H. (1998) Highly Efficient Synthesis of Covalently Cross-Linked Peptide Helices by Ring-Closing Metathesis, Angew. Chem., Int. Ed. 37, 3281-3284.
Bracken, et al. (1994) Synthesis and Nuclear Magnetic Resonance Structure Determination of an .alpha.-Helical, Bicyclic, Lactam-Bridged Hexapeptide, J. Am. Chem. Soc., 116, 6431-6432.
Cantel et al. (2008) Synthesis and conformational analysis of a cyclic peptide obtained via i to i+4 intramolecular side-chain to side-chain azide-alkyne 1,3-dipolar cycloaddition, J. Org. Chem., 73 (15), 5663-5674.
Heinis, C. et al., (2009) Phage-encoded combinatorial chemical libraries based on bicyclic peptides. Nat Chem Biol. 5 (7):502-7.
Ripka, A.S. et al., (1998) Synthesis of novel cyclic protease inhibitors using grubbs olefin metathesis. Bioorg Med Chem Lett. 8(4):357-60.
Risseeuw, M.D.P., (2009) Alkylated and bicyclic sugar amino acids: synthesis and applications. Doctoral Thesis, Leiden University. Chapter 1, p. 9-26.
Schafmeister and Verdine (2000) An All-Hydrocarbon Cross-Linking System for Enhancing the Helicity and Metabolic Stability of Peptides, J. Am. Chem. Soc., 122 (24), 5891-5892.
Scott et al. (1999) Production of cyclic peptides and proteins in vivo, PNAS. vol. 96 No. 24 p. 13638-13643.
First Examination Report dated May 22, 2017 in New Zealand Application No. 727420 entitled "Modulation of Complement Activity".
International Search Report and Written Opinion dated Mar. 17, 2017 in Application No. PCT/US2016/065228, entitled: Modulators of Complement Activity.
Ricardo et al. "Preclinical Evaluation of RA101495, a Potent Cyclic Peptide Inhibitor of C5 for the Treatment of Paroxysmal Nocturnal Hemoglobinuria", Dec. 5, 2015.
Hammer, R. P. "Harnessing mRNA—Display for the Discovery of Macrocyclic Peptide Drugs" Mar. 14, 2016.
Third Examination Report for corresponding Australian Application No. 2015274482 dated Aug. 28, 2018.
Fourth Examination Report for corresponding Australian Application No. 2015274482 dated Sep. 13, 2018.
Extended European Search Report for corresponding European Application No. 16744125.2 dated Dec. 21, 2018.
Chinese Office Action for corresponding Chinese Application No. 2015800313418 dated Dec. 21, 2018.
Ricardo et al 2014 (Dec. 2014 ASH abstract) Development of RA101348, a Potent Cyclic Peptide Inhibitor of C5 for Complement-Mediated Diseases.
Cheng et al. Chromatographic separtion and Tandem MS identification of active peptides in potato protein hydrolysate that inhibit autoxidation of soybean oil-in-water emulsions. Journal of Agricultural and Food Chemistry 2010, 58 (15):8825-8832; Abstract.
Janke et al. The arginine mimicking [beta]-amino acid [beta]3hPhe(3-H2N-CH) as S1 ligand in cyclotheonamide-based [beta]-tryptase inhibitors. Bioorg Med Chem. 2011, 19(23):7236-43;p. 7237, col. 1, Scheme 2.
International Search Report and Written Opinion dated Dec. 4, 2015 in Application No. PCT/US2015/035473, entitled: Modulation of Complement Activity.

(56) References Cited

OTHER PUBLICATIONS

ARIPO Form 18 Office Action for corresponding ARIPO Application No. AP/P/2016/009612 entitled "Modulation of Complement Activity" dated Feb. 19, 2019.
Israel Office Action for corresponding Israel application No. 259762 entitled "Modulators of Complement Activity" dated Jun. 30, 2019.
International Search Report and Written Opinion dated Mar. 1, 2019 in application No. PCT/US2018/063719 entitled "Modulators of Complement Activity".
First Examination Report for corresponding India Application No. 201617040921 entitled "Modulation of Complement Activity" dated Dec. 9, 2019.
Extended European Search Report for corresponding European Application No. 19194070.9 dated Mar. 2, 2020.
International Search Report and Written Opinion dated Nov. 15, 2018 in applicaiton No. PCT/US2018/050317 entitled: Formulations for Compound Delivery.
Cichewicz et al. Cutaneous delivery of alpha-tocopherol and lipoic acid using microemulsions: influence of composition and charge J Pharm Pharmacol. Jun. 2013, vol. 65, No. 6, pp. 817-826.
Russian Office Action for corresponding Russian Application No. 2018121615 entitled "Modulators of Complement Activity" dated Mar. 16, 2020.
Josephson, K. et al., (2013) "mRNA display: from basic principles to macrocycle drug discovery" Drug Discovery Today, vol. 00, No. 00.
Ricardo A. et al. 939 Preclinical evaluation of RA101495, a potent cyclic peptide inhibitor of C5 for the treatment of paroxysmal nocturnal hemoglobinuria. 57th Annual Meeting and Exposition. Orlando, FL. Dec. 5-8, 2015.
Lee et al. "Pharmacological inhibition of complement C5a-C5a1 receptor signalling ameliorates disease pathology in the hSOD1G93A mouse model of amyotrophic lateral sclerosis" British Journal of Pharmacology, vol. 174, No. 8, Mar. 3, 2017.
Park, Brian "Zilucoplan for Myasthenia Gravis Gets Orphan Drug Designation" Neurology Advisor, Sep. 9, 2019.
Anonymous: "NCT04436497: Healey ALS Platform Trial—Regimen A Zilucoplan" Jun. 17, 2020.
Garbuzova-Davis and Sanberg "Blood-CNS Barrier Impairment in ALS patients versus an animal model" Frontiers in Cellular Neuroscience, vol. 8, Jan. 1, 2014.
Van De Walle Inge et al: "ARGX-117, a therapeutic complement inhibiting antibody targeting C2", Journal of Allergy and Clinical Immunology, Elsevier, Amsterdam, NL, vol. 147, No. 4, Sep. 11, 2020, p. 1420.
Garland Donita L. et al: "Abstract", Scientific Reports, vol. 11, No. 1, Jan. 1, 2021, Retrieved from the Internet: URL:https://www.nature.com/articles/s41598-021-89978-8.pdf.
Milletti, F., 2012 Cell-penetrating peptides: classes, origin, and current landscape. Drug Discov Today. Aug.;17 (15-16):850-60.
Hartman, M.C.T. et al. (2007) An expanded set of amino acid analogs for the ribosomal translation of unnatural peptides, PLoS One 2:e972.
Millward, S.W. et al., (2005) A general route for post-translational cyclization of mRNA display libraries, J. Am. Chem. Soc. 127:14142-14143.
Murakami, H. et al. (2006) A highly flexible tRNA acylation method for non-natural polypeptide synthesis, Nat. Methods 3:357-359.
Nemoto, H. et al., (1997) In vitro virus: bonding of mRNA bearing puromycin at the 3'-terminal end to the C-terminal and of its encoded protein on the ribosome in vitro, FEBS Lett. 414:405-408.
Nguyen A. et al., (2006) The pharmacokinetics of an albumin-binding Fab (AB.Fab) can be modulated as a function of affinity for albumin. Protein Eng Des Sel. 19:291-7.
Nishimura et al (2012) A rare genetic polymorphism in C5 confers poor response to the anti-C5 monoclonal antibody eculizumab by nine Japanese patients with PNH. Blood (ASH Annual Meeting Abstracts) 120: Abstract 3197.
Oliva, B. et al., (1997) An automated classification of the structure of protein loops, J Mol Biol. Mar. 7;266(4):814-30.

Parker, G.J. et al., (2000) Development of high throughput screening assays using fluorescence polarization: nuclear receptor-ligand-binding and kinase/phosphatase assays. J Biomol Screen. Apr. 2000;5(2):77-88.
Prystay, L. et al., (2001) Determination of equilibrium dissociation constants in fluorescence polarization. J Biomol Screen. Jun.;6(3):141-50.
Roberts, R.W., and Szostak, J.W. (1997) RNA-peptide fusions for the in vitro selection of peptides and proteins, Proc. Natl. Acad. Sci. USA 94, 12297-12302.
Rothe, A. et al. (2006) In vitro display technologies reveal novel biopharmaceutics, The FASEB Journal. 20 (10):1599-1610.
Josephson, K. et al., (2005) Ribosomal synthesis of unnatural peptides, J. Am. Chem. Soc. 127: 11727-11735.
Sando, S. et al., (2007) Unexpected preference of the *E. coli* translation system for the ester bond during incorporation of backbone-elongated substrates, J. Am. Chem. Soc. 129:6180-6186.
Seebeck, F.P. and Szostak, J.W. (2006) Ribosomal synthesis of dehydroalanine-containing peptides J. Am. Chem. Soc. Jun. 7;128(22):7150-1.
Sergeeva, A. et al. (2006). Display technologies: application for the discovery of drug and gene delivery agents, Adv. Drug Deliv. Rev. 58:1622-1654.
Shimizu, Y. et al. (2001) Cell-free translation reconstituted with purified components, Nat. Biotech. 19:751-755.
Smith, G.P. and Petrenko, V.A., (1997) Phage Display, Chem. Rev. 97:391-410.
Takashashi, T.T et al. (2003) mRNA display: ligand discovery, interaction analysis and beyond, Trends in Biochem. Sci. 28(3):159-165.
Tian, W. et al., (2012) Development of novel fluorescence polarization-based assay for studying the β-catenin/Tcf4 interaction. J Biomol Screen. Apr.;17(4):530-4.
Timmerman, P. et al., (2005) Rapid and quantitative cyclization of multiple peptide loops onto synthetic scaffolds for structural mimicry of protein surfaces, ChemBioChem 6:821-824.
Van den Eisen, J.M.H., (2002) X-ray crystal structure of the C4d fragment of human complement component C4, J. Mol. Biol. 322:1103-1115.
Goto, Y. et al. (2008) Reprogramming the translation initiation for the synthesis of physiologically stable cyclic peptides, ACS Chem. Biol. 3:120-129.
Pu, J.J. et al., (2011) Paroxysmal nocturnal hemoglobinuria from bench to bedside. Clin Transl Sci. Jun.;4(3):219-24.
Schlippe, et al. (2012) In vitro selection of highly modified cyclic peptides that act as tight binding inhibitors. J Am Chem. 134:10469-77.
Ballanti et al., (2013) Complement and autoimmunity. Immunol Res 56:477-491.
Cazander G., et al., (2012) Complement activation and inhibition in wound healing. Clin Dev Immunol, 2012:534291.
DeAngelis RA., et al., (2012) Targeted complement inhibition as a promising strategy for preventing inflammatory complications in hemodialysis.,Immunobiology, 217(11): 1097-1105.
Engelhardt, et al., (2002) Severe cold hemagglutinin disease (CHD) successfully treated with rituximab., Blood, 100 (5):1922-23.
Haeger M., et al., (1992) Complement, neutrophil, and macrophage activation in women with severe preeclampsia and the syndrome of hemolysis, elevated liver enzymes, and low platelet count in Obstetrics & Gynecology, 79(1):19-26.
Hajishengallis G. (2010) Complement and periodontitis. Biochem Pharmacol. 15; 80(12): 1.
Jennette et al., (2013) Complement in ANCA-associated vasculitis., Semin Nephrol. 33(6): 557-64.
Jha P., et al., (2007) The role of complement system in ocular diseases including uveitis and macular degeneration., Mol Immunol. 44(16):3901-3908.
Kourtzelis I., et al., (2010) Complement anaphylatoxin C5a contributes to hemodialysis-associated thrombosis., Blood, 116(4):631-639.
Subtelny et al., (2008) Ribosomal synthesis of N-methyl peptides, J. Am. Chem. Soc. 130: 6131-6136.

(56) References Cited

OTHER PUBLICATIONS

Mackworth-Young, (2004) Antiphospholipid syndrome: multiple mechanisms., Clin Exp Immunol 136:393-401.
Markiewski, et al., (2007) The role of complement in inflammatory diseases from behind the scenes into the spotlight. Am J Pathol. 171:715-27.
Meri S., (2013) Complement activation in diseases presenting with thrombotic microangiopathy., European Journal of Internal Medicine, 24: 496-502.
Quigg RJ., (2003) Complement and the kidney., J Immunol 171:3319-24.
Rock, et al., (2010) The sterile inflammatory response. Annu Rev Immunol. 28:321-342.
Roth et al., (2009) Long-term efficacy of the complement inhibitor eculizumab in cold agglutinin disease.,Blood, 113:3885-86.
Rubartelli, et al., (2013) Mechanisms of sterile inflammation. Frontiers in Immunology 4:398-99.
Salmon, et al., (2002) Complement activation as a mediator of antiphospholipid antibody induced pregnancy loss and thrombosis. Ann Rheum Dis 2002;61 (Suppl II):ii46-ii50.
Sjoberg A.T., et al., (2009) Complement activation and inhibition: a delicate balance. Trends in Immunology. 30(2):83-90.
Stahel et al., (1998) The role of the complement system in traumatic brain injury.Brain Research Reviews, 27: 243-56.
Baggio, R. et al. (2002) Identification of epitope-like consensus motifs using mRNA display, J. Mol. Recog. 15:126-134.
Van de Goot F., et al., (2009) Acute inflammation is persistent locally in burn wounds: a pivotal role for complement and C-reactive protein . J Burn Care Res 2009, 30:274-280.
Altschul et al., (1997) Gapped BLAST and PSI-BLAST: a new generation of protein database search programs, Nucleic Acids Res. 25(17):3389-3402.
Amara, et al., (2008) "Interaction Between the Coagulation and Complement System" in Current Topics in Complement II, J.D. Lambris (ed.), pp. 71-79 (Adv Exp Med Biol. 2008;632:71-9).
Amara, et al., (2010) Molecular intercommunication between the complement and coagulation systems. J. Immunol. 185:5628-5636.
Canadian Examination Report for corresponding Canadian Application No. 2949985, dated Oct. 26, 2017.
Japanese Office Action for corresponding Japanese Application No. 2017-517219, dated Nov. 21, 2017.
Australian Examination Report for corresponding Australian Application No. 2015274482, dated Nov. 24, 2017.
Russian Office Action for corresponding Russian Application No. 2016147080, dated Dec. 20, 2017.
Singapore Written Opinion for corresponding Singapore Application No. 11201610222U, dated Dec. 28, 2017.
Chang, Kyeong-Ok Characterization and inhibition of norovirus proteases of genogroups I and II using a fluorescence resonance energy transfer assay. Virology, 2012, 423(2), 125-133.
International Search Report and Written Opinion dated Apr. 22, 2016 in application No. PCT/US2016/015412, entitled: Modulators of Complement Activity.
Genbank Accession No. EKQ53330.1, hypothetical protein B655 1297 [*Methanobacterium* sp. Maddingley MBC34] Sep. 26, 2013 [online]. Retrieved from the Internet <URL: http:www.ncbi.nlm.nih.gov/protein/EKQ53330.1>.
Ricardo et al., "Development of RA101348, a Potent Cyclic Peptide Inhibitor of C5 for Complement-Mediated Diseases", Dec. 17, 2014 56th ASH Annual Meeting and Exposition. (last updated Dec. 17, 2014) Abstract retrieved from website <URL https://ash.confex.com/ash/2014/webprogram/Paper74528.html>.
International Search Report and Written Opinion dated Apr. 24, 2018 in application No. PCT/US2017/065005, entitled: Modulators of Complement Activity.
Hammer, R.P., "Harnessing mRNS-display for the Discovery of Macrocyclic Peptide Drugs" BPS Peptide Showcase East, Mar. 14, 2016.
Extended European Search Report for corresponding European Application No. 15807069.8 dated Mar. 19, 2018.
Second Examination Report for corresponding Australian Application No. 2015274482 dated May 10, 2018.
Examination Report for corresponding New Zealand Application No. 727420 dated May 25, 2018.
Russian Office Action for corresponding Russian Application No. 2016147080 dated May 30, 2018.
Japanese Office Action for corresponding Japanese Application No. 2017-517219 dated Jun. 5, 2018.
Korean Office Action for corresponding Korean Application No. 10-2016-7034788 dated Jun. 5, 2018.
Forster, A.C. et al. (2003) Programming peptidomimetic syntheses by translating genetic codes designed de novo, Proc. Natl. Acad. Sci. USA 100: 6353-6357.
Berman, H.M. et al., (2000) The Protein Data Bank, Nucleic Acids Research, 28: 235-242.
Smith, A. B. 3rd, et al. (1994) De Novo Design, Synthesis, and X-ray Crystal Structures of Pyrrolinone-Based .beta.-Strand Peptidomimetics, J. Am Chem. Soc. 116:9947-9962.
Yamagishi, Y. et al., (2011) Natural product-like macrocyclic N-methyl peptide inhibitors against a ubiquitin ligase uncovered from a ribosome-expressed de novo library. Chemistry & Biology 18:1562-70.
Brodsky (2014) Paroxysmal nocturnal hemoglobinuria. Blood 2014;124:2804-2811.
Hill et al., (2006) The incidence and prevalence of paroxysmal nocturnal hemoglobinuria (PNH) and survival of patients in Yorkshire. Blood 2006;108:Abstract 985.
Hillmen et al., (2013) Long-term safety and efficacy of sustained eculizumab treatment in patients with paroxysmal nocturnal haemoglobinuria. Br J Haematol 2013;162:62-73.
Kairemo E et al., (2010) A nationwide survey of paroxysmal nocturnal haemoglobinuria in Finland. Haematologica 2010;95[suppl. 2]:303:Abstract 0727.
Nakayama H et al., (2016) Eculizumab dosing intervals longer than 17 days may be associated with greater risk of breakthrough hemolysis in patients with paroxysmal nocturnal hemoglobinuria. Biol Pharm Bull.
Nishimura J-I et al., (2004) Clinical course and flow cytometric analysis of paroxysmal nocturnal hemoglobinuria in the United States and Japan. Medicine 2004;83:193-207.
Socie' G et al., (1996) Paroxysmal nocturnal haemoglobinura: long-term follow-up and prognostic factors. Lancet 1996;348:573-577.
Keshar et al 2014 (Dec. 2014 ASH abstract) A Novel C5 Complement Inhibitor Protects Against Sepsis-Induced Activation of Complement, Coagulation and Inflammation and Provides Survival Benefit in *E. coli* Sepsis.
Coin, I et al. (2007) Solid-phase peptide synthesis: from standard procedures to the synthesis of difficult sequences, Nature Protcols 2(12):3247-56.
Keshari et al 2015 (ASH abstract—Blood 2015 126(765)) Complement C5 Inhibition Blocks the Cytokine Storm and Consumptive Coagulopathy by Decreasing Lipopolysaccharide (LPS) Release in *E. coli* Sepsis.
Ricardo et al 2015 (Dec. 2015 ASH abstract) Preclinical Evaluation of RA101495, a Potent Cyclic Peptide Inhibitor of C5 for the Treatment of Paroxysmal Nocturnal Hemoglobinuria.
Cwirla, S.E. et al. (1990) Peptides on phage: a vast library of peptides for identifying ligands, Proc. Natl. Acad. Sci. U.S.A. 87:6378-6382.
Dedkova, L. et al. (2003) Enhanced D-amino acid incorporation into protein by modified ribosomes, J. Am. Chem. Soc. 125: 6616-6617.
Dennis et al. (2002) Albumin binding as a general strategy for improving the pharmokinetics of proteins. J Biol Chem. 277(38): 35035-43.
Devlin, J.J., et. al., (1990). Random peptide libraries: a source of specific protein binding molecules, Science 249, 404-406.
Frankel, A. et al., (2003) Encodamers: unnatural peptide oligomers encoded in RNA, Chem. Biol. 10:1043-1050.
Fredslund, F. et al. (2008). Structure of and influence of a tick complement inhibitor on human complement component 5, Nature 9:753-760.

(56) References Cited

OTHER PUBLICATIONS

Hadders, M.A. et al. (2012). Assembly and regulation of the membrane attack complex based on structures of C5b6 and sC5b9, Cell Reports 1:200-207.
He, M and Taussig, M (2002). Briefs in Functional Genomics and Proteomics. 1(2): 204-212.
Hartman et al., (2006) Enzymatic aminoacylation of tRNA with unnatural amino acids, Proc. Natl. Acad. Sci. USA 103:4356-4361.
Hollinger, P. et al., "Diabodies":Small bivalent and bispecific antibody fragments. PNAS. 1993. 90:6444-8.
Jackson, R.J., et al., (2001) Development of a tRNA-dependent in vitro translation system, RNA 7:765-773.
Kay, B.K. et al. (2001) Screening phage-displayed combinatorial peptide libraries, Methods. 24:240-246.
Keefe, A.D. and Szostak, J.W. (2001) Functional proteins from a random-sequence library, Nature 15:715-718.
Langenheim, J.F. et al., (2009) Improving the pharmacokinetics/pharmacodynamics of prolactin, GH, and their antagonists by fusion to a synthetic albumin-binding peptide. J Endocrinol. 203(3):375-87.
Law, S.K., et al. (1997). The internal thioester and the covalent binding properties of the complement proteins C3 and C4. Protein Science. 6:263-274.
Lea, W.A. et al., (2011) Fluorescence polarization assays in small molecule screening. Expert Opin Drug Discov. Jan.;6(1):17-32.
Levengood, M.R. and Van der Donk, W.A., (2008) Use of lantibiotic synthetases for the preparation of bioactive constrained peptides, Bioorg. and Med. Chem. Lett. 18:3025-3028.
Liu, R. et al. (2000). Optimized synthesis of RNA-protein fusions for in vitro protein selection, Methods Enzymol. 318:268-293.

\* cited by examiner

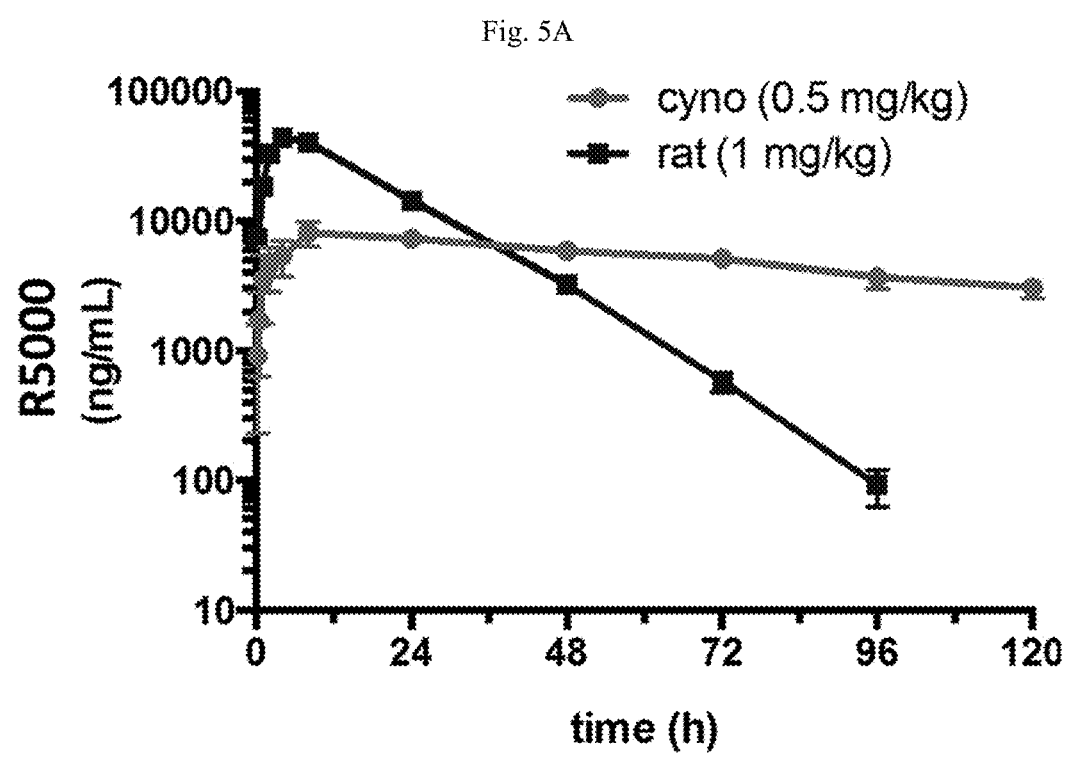

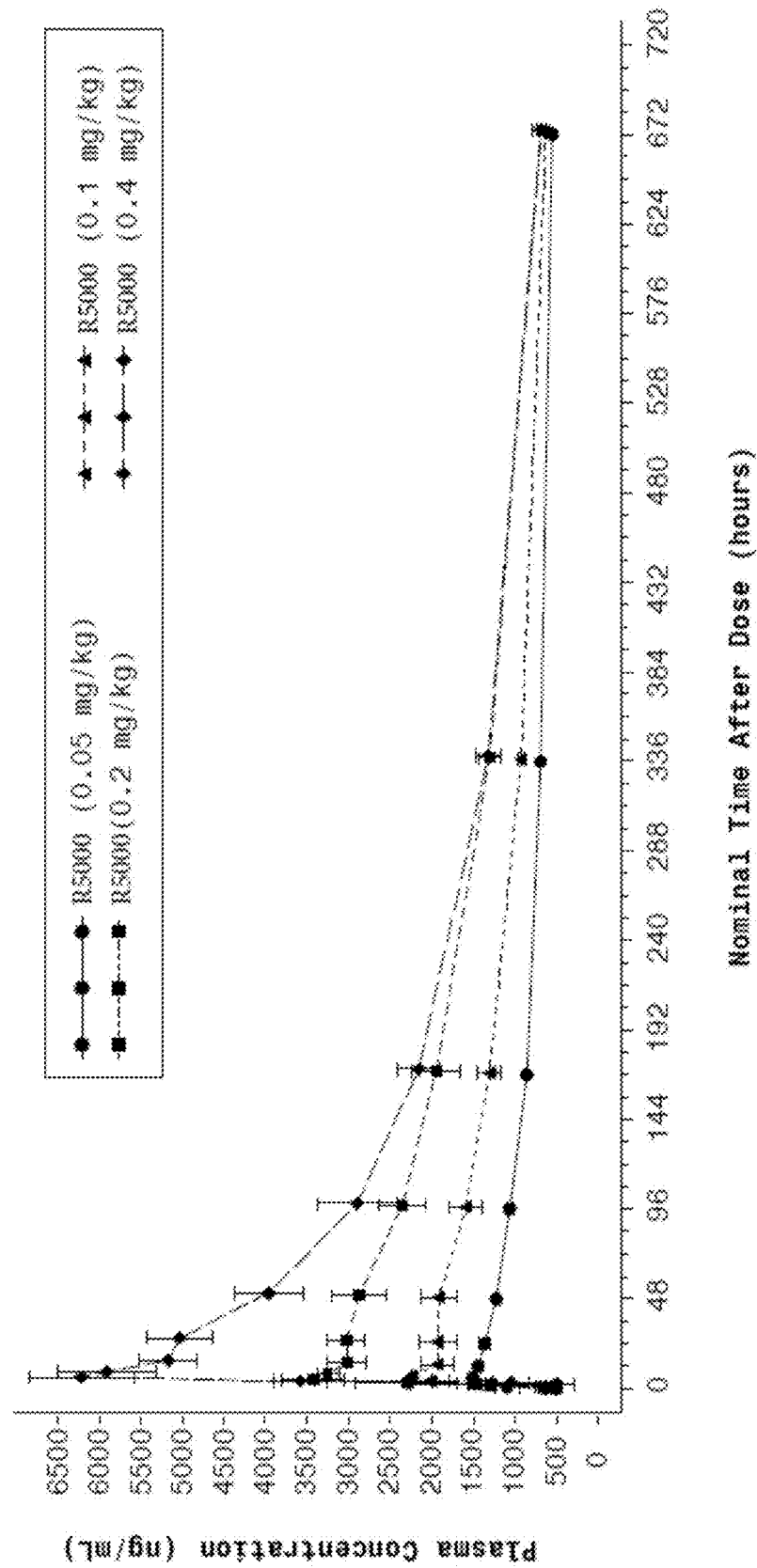

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MISC_FEATURE
<222> LOCATION: (1)..(6)
<223> OTHER INFORMATION: Lactam bridge between residues
<220> FEATURE:
<221> NAME/KEY: MOD_RES
<222> LOCATION: (7)..(7)
<223> OTHER INFORMATION: (N-Me)Asp
<220> FEATURE:
<221> NAME/KEY: MOD_RES
<222> LOCATION: (8)..(8)
<223> OTHER INFORMATION: Tert-butyl-Gly
<220> FEATURE:
<221> NAME/KEY: MOD_RES
<222> LOCATION: (10)..(10)
<223> OTHER INFORMATION: 7-aza-Trp
<220> FEATURE:
<221> NAME/KEY: MOD_RES
<222> LOCATION: (14)..(14)
<223> OTHER INFORMATION: Cyclohexyl-Gly
<220> FEATURE:
<221> NAME/KEY: MOD_RES
<222> LOCATION: (15)..(15)
<223> OTHER INFORMATION: N-epsilon-(PEG24-gamma-glutamic acid-N-alpha-
      hexadecanoyl)Lys

<400> SEQUENCE: 1

Lys Val Glu Arg Phe Asp Asp Gly Tyr Trp Glu Tyr Pro Gly Lys
1               5                   10                  15
```

MODULATORS OF COMPLEMENT ACTIVITY

CROSS REFERENCE TO RELATED APPLICATIONS

This application is a continuation of U.S. patent application Ser. No. 16/062,653 filed on Jun. 15, 2018, which is a 35 U.S.C. § 371 United States National Stage Entry of International Application Number PCT/US2016/065228 filed Dec. 7, 2016, which claims the benefit of priority of U.S. Provisional Application No. 62/268,360 entitled Modulators of Complement Activity filed on Dec. 16, 2015; U.S. Provisional Application No. 62/331,320 entitled Modulators of Complement Activity filed on May 3, 2016; and U.S. Provisional Application No. 62/347,486 entitled Modulators of Complement Activity filed on Jun. 8, 2016, the contents of each of which are herein incorporated by reference in their entirety.

SEQUENCE LISTING

The instant application contains a Sequence Listing which has been filed electronically in ASCII format and is hereby incorporated by reference in its entirety. Said ASCII copy, created on Oct. 7, 2020, is named 2011_1009USCON_SL.txt and is 1,323 bytes in size.

FIELD OF THE INVENTION

The present invention relates to compounds, including polypeptides, which are useful as modulators of complement activity. Also provided are methods of utilizing these modulators as therapeutics.

BACKGROUND OF THE INVENTION

The vertebrate immune response is comprised of adaptive and innate immune components. While the adaptive immune response is selective for particular pathogens and is slow to respond, components of the innate immune response recognize a broad range of pathogens and respond rapidly upon infection. One such component of the innate immune response is the complement system.

The complement system includes about 20 circulating complement component proteins, synthesized primarily by the liver. Components of this particular immune response were first termed "complement" due to the observation that they complemented the antibody response in the destruction of bacteria. These proteins remain in an inactive form prior to activation in response to infection. Activation occurs by way of a pathway of proteolytic cleavage initiated by pathogen recognition and leading to pathogen destruction. Three such pathways are known in the complement system and are referred to as the classical pathway, the lectin pathway, and the alternative pathway. The classical pathway is activated when an IgG or IgM molecule binds to the surface of a pathogen. The lectin pathway is initiated by the mannan-binding lectin protein recognizing the sugar residues of a bacterial cell wall. The alternative pathway remains active at low levels in the absence of any specific stimuli. While all three pathways differ with regard to initiating events, all three pathways converge with the cleavage of complement component C3. C3 is cleaved into two products termed C3a and C3b. Of these, C3b becomes covalently linked to the pathogen surface while C3a acts as a diffusible signal to promote inflammation and recruit circulating immune cells. Surface-associated C3b forms a complex with other components to initiate a cascade of reactions among the later components of the complement system. Due to the requirement for surface attachment, complement activity remains localized and minimizes destruction to non-target cells.

Pathogen-associated C3b facilitates pathogen destruction in two ways. In one pathway, C3b is recognized directly by phagocytic cells and leads to engulfment of the pathogen. In the second pathway, pathogen-associated C3b initiates the formation of the membrane attack complex (MAC). In the first step, C3b complexes with other complement components to form the C5-convertase complex. Depending on the initial complement activation pathway, the components of this complex may differ. C5-convertase formed as the result of the classical complement pathway comprises C4b and C2a in addition to C3b. When formed by the alternative pathway, C5-convertase comprises two subunits of C3b as well as one Bb component.

Complement component C5 is cleaved by either C5-convertase complex into C5a and C5b. C5a, much like C3a, diffuses into the circulation and promotes inflammation, acting as a chemoattractant for inflammatory cells. C5b remains attached to the cell surface where it triggers the formation of the MAC through interactions with C6, C7, C8 and C9. The MAC is a hydrophilic pore that spans the membrane and promotes the free flow of fluid into and out of the cell, thereby destroying it.

An important component of all immune activity is the ability of the immune system to distinguish between self and non-self cells. Pathology arises when the immune system is unable to make this distinction. In the case of the complement system, vertebrate cells express proteins that protect them from the effects of the complement cascade. This ensures that targets of the complement system are limited to pathogenic cells. Many complement-related disorders and diseases are associated with abnormal destruction of self cells by the complement cascade. In one example, subjects suffering from paroxysmal nocturnal hemoglobinuria (PNH) are unable to synthesize functional versions of the complement regulatory proteins CD55 and CD59 on hematopoietic stem cells. This results in complement-mediated hemolysis and a variety of downstream complications. Other complement-related disorders and diseases include, but are not limited to autoimmune diseases and disorders; neurological diseases and disorders; blood diseases and disorders; and infectious diseases and disorders. Experimental evidence suggests that many complement-related disorders are alleviated through inhibition of complement activity. Therefore, there is a need for compositions and methods for selectively blocking complement-mediated cell destruction to treat related indications. The present invention meets this need by providing related compositions and methods.

SUMMARY OF THE INVENTION

In some embodiments, the present disclosure provides a pharmaceutical composition that includes R5000 and a pharmaceutically acceptable excipient, wherein the pharmaceutically acceptable excipient includes sodium chloride at a concentration of from about 25 mM to about 100 mM and sodium phosphate at a concentration of from about 10 mM to about 100 mM. R5000 may be present at a concentration of from about 1 mg/mL to about 400 mg/mL. The pharmaceutical composition may include a pH of from about 6.5 to about 7.5. R5000 may bind to C5 with an equilibrium dissociation constant ($K_D$) of from about 0.1 nM to about 1 nM. R5000 may block production of C5a following activation of the alternative pathway of complement activation. R5000 may block formation of the membrane attack complex (MAC) following activation of the classical pathway, alternative pathway, or lectin pathway of complement activation.

In some embodiments, the present disclosure provides a method of inhibiting hemolysis in a subject that includes administering a pharmaceutical composition that includes R5000 and a pharmaceutically acceptable excipient, wherein the pharmaceutically acceptable excipient includes sodium chloride at a concentration of from about 25 mM to about 100 mM and sodium phosphate at a concentration of from about 10 mM to about 100 mM. The pharmaceutical composition may be administered at a dose sufficient to achieve plasma levels of R5000 of from about 0.1 μg/mL to about 20 μg/mL. Hemolysis may be inhibited from about 25% to 100% after administration. The pharmaceutical composition may be administered daily for at least two days. The pharmaceutical composition may be administered daily for 7 days. The pharmaceutical composition may be administered daily for at least 100 days. According to some methods, no adverse cardiovascular, respiratory, and/or central nervous system (CNS) effects are observed for at least 1 month subsequent to administration. According to some methods, no changes in heart rate and/or arterial blood pressure are observed for at least 1 month subsequent to administration. According to some methods, no changes to respiratory rate, tidal volume, and/or minute volume are observed for at least 1 month subsequent to administration.

In some embodiments, the present disclosure provides a method of inhibiting hemolysis in a subject that includes administering a pharmaceutical composition that includes R5000 and a pharmaceutically acceptable excipient, wherein the pharmaceutically acceptable excipient includes sodium chloride at a concentration of from about 25 mM to about 100 mM and sodium phosphate at a concentration of from about 10 mM to about 100 mM, wherein the pharmaceutical composition may be administered subcutaneously (SC) or intravenously (IV). The half-life ($t_{1/2}$) of R5000 levels in subject plasma may be at least 4 hours. The $t_{1/2}$ of R5000 levels in subject plasma may be from about 1 day to about 10 days. The steady state volume of distribution of R5000 in subject plasma may be from about 10 mL/kg to about 200 mL/kg. The steady state volume of distribution of R5000 in subject plasma may be equal to at least 50% of total blood volume. The total clearance rate of R5000 in subject plasma may be from about 0.04 mL/hr/kg to about 4 mL/hr/kg. The $T_{max}$ of R5000 in subject plasma may be from about 1 hour to about 48 hours. The presence of measurable amounts of R5000 may be substantially restricted to the plasma compartment. The pharmaceutical composition may be administered at a dose sufficient to deliver from about 0.01 mg to about 2 mg of R5000 per kg weight of the subject. From about 50% to about 99% of C5 activation in the subject may be inhibited. The pharmaceutical composition may be administered at a dose sufficient to deliver from about 0.1 mg to about 0.4 mg of R5000 per kg weight of the subject. The pharmaceutical composition may be administered subcutaneously or intravenously. The pharmaceutical composition may be administered one or more times daily. The pharmaceutical composition may be administered for a period of 7 days. The percent inhibition of hemolysis may be from at least 90% to about 95% or more by 3 hours after a first administration. The percent inhibition of hemolysis may be from at least 90% to about 95% or more as measured at least 7 days post administration. The percent inhibition of hemolysis may be from at least 90% to about 95% or more for at least 4 days after administration. The maximum inhibition of hemolysis and/or maximum inhibition of complement activity may be achieved from about 2 hours after administration to about 4 hours after administration.

In some embodiments, the present disclosure provides a method of inhibiting hemolysis in a subject that includes administering a pharmaceutical composition that includes R5000 and a pharmaceutically acceptable excipient, wherein the pharmaceutically acceptable excipient includes sodium chloride at a concentration of from about 25 mM to about 100 mM and sodium phosphate at a concentration of from about 10 mM to about 100 mM, wherein R5000 is administered at a dose of 0.2 mg/kg. Hemolysis may be ≤3% at 24 hours after the last administration. Complement activity may be reduced to from about 1 percent to about 10 percent during the period of 7 days. Complement activity may be ≤5% at 24 hours after the last administration. The pharmaceutical composition may be administered daily by subcutaneous or intravenous injection at a dose sufficient to deliver from about 0.1 mg/day to about 60 mg/day of R5000 per kg weight of the subject. The maximum serum concentration ($C_{max}$) achieved may be from about 0.1 μg/mL to about 1000 μg/mL. The area under the curve (AUC) may be from about 200 μg*hr/mL to about 10,000 μg*hr/mL.

In some embodiments, the present disclosure provides a method of treating paroxysmal nocturnal hemoglobinuria (PNH) in a subject in need thereof that includes the subcutaneous or intravenous administration of a pharmaceutical composition that includes R5000 and a pharmaceutically acceptable excipient, wherein the pharmaceutically acceptable excipient includes sodium chloride at a concentration of from about 25 mM to about 100 mM and sodium phosphate at a concentration of from about 10 mM to about 100 mM. The subject may have been treated previously with an antibody-based therapeutic. PNH in the subject may be resistant or unresponsive to treatment with an antibody-based therapeutic. The antibody-based therapeutic may be eculizumab.

In some embodiments, the present disclosure provides a kit that includes a pharmaceutical composition that includes R5000 and a pharmaceutically acceptable excipient, wherein the pharmaceutically acceptable excipient includes sodium chloride at a concentration of from about 25 mM to about 100 mM and sodium phosphate at a concentration of from about 10 mM to about 100 mM.

In some embodiments, the present disclosure provides an auto-injector device that includes a pharmaceutically acceptable excipient, wherein the pharmaceutically acceptable excipient includes sodium chloride at a concentration of from about 25 mM to about 100 mM and sodium phosphate at a concentration of from about 10 mM to about 100 mM.

BRIEF DESCRIPTION OF THE FIGURES

The foregoing and other objects, features and advantages will be apparent from the following description of particular embodiments of the invention, as well as the accompanying drawings illustrating the principles of various embodiments of the invention.

FIG. 5A is a graph showing R5000 levels over time after subcutaneous administration in rat and monkey.

FIG. 11B is a graph showing plasma concentrations over time after single dose administration of R5000.

DETAILED DESCRIPTION

I. Compounds and Compositions

Figure 1:
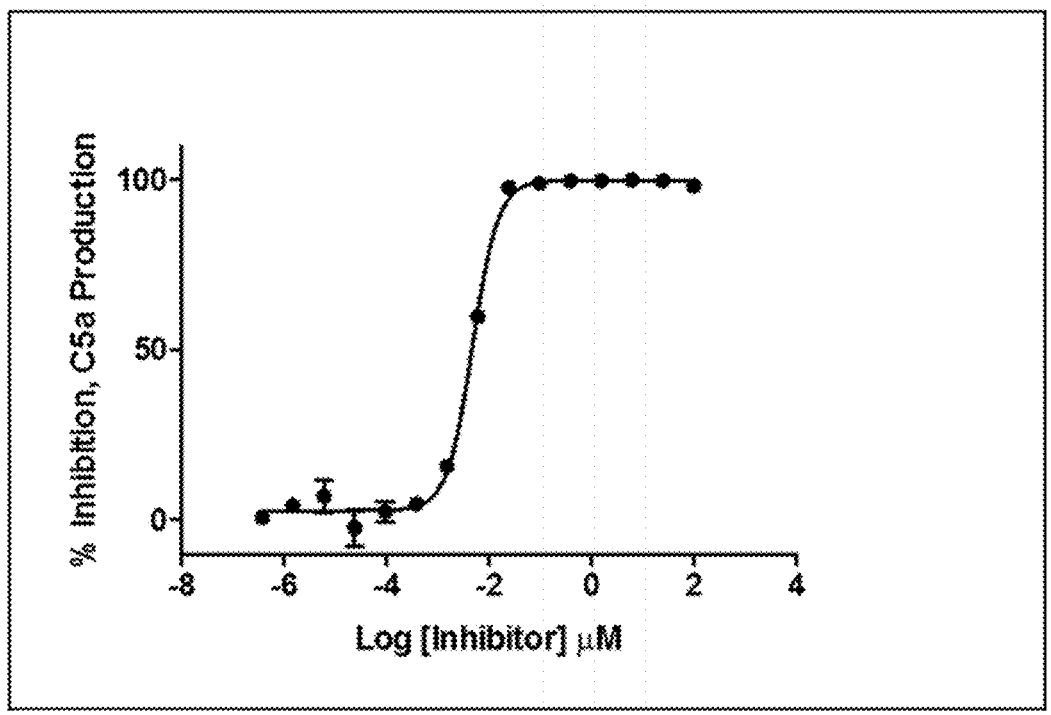
FIG. 1 is a scatter plot showing R5000 inhibition of C5a production.

According to the present invention, compounds and compositions are provided which function to modulate complement activity. Such compounds and compositions of the invention may include inhibitors that block complement activation. As used herein, "complement activity" includes the activation of the complement cascade, the formation of cleavage products from a complement component such as C3 or C5, the assembly of downstream complexes following a cleavage event, or any process or event attendant to, or resulting from, the cleavage of a complement component, e.g., C3 or C5. Complement inhibitors may include C5 inhibitors that block complement activation at the level of complement component C5. C5 inhibitors may bind C5 and prevent its cleavage, by C5 convertase, into the cleavage products C5a and C5b. As used herein, "Complement component C5" or "C5" is defined as a complex which is cleaved by C5 convertase into at least the cleavage products, C5a and C5b. "C5 inhibitors," according to the invention, comprise any compound or composition that inhibits the processing or cleavage of the pre-cleaved complement component C5 complex or the cleavage products of the complement component C5.

It is understood that inhibition of C5 cleavage prevents the assembly and activity of the cytolytic membrane attack complex (MAC) on glycosylphosphatidylinositol (GPI) adherent protein-deficient erythrocytes. As such, in some cases, C5 inhibitors of the invention may also bind C5b, preventing C6 binding and subsequent assembly of the C5b-9 MAC.

Peptide-Based Compounds

In some embodiments, C5 inhibitors of the invention are polypeptides. According to the present invention, any amino acid-based molecule (natural or unnatural) may be termed a "polypeptide" and this term embraces "peptides," "peptidomimetics," and "proteins." "Peptides" are traditionally considered to range in size from about 4 to about 50 amino acids. Polypeptides larger than about 50 amino acids are generally termed "proteins."

C5 inhibitor polypeptides may be linear or cyclic. Cyclic polypeptides include any polypeptides that have as part of their structure one or more cyclic features such as a loop and/or an internal linkage. In some embodiments, cyclic polypeptides are formed when a molecule acts as a bridging moiety to link two or more regions of the polypeptide. As used herein, the term "bridging moiety" refers to one or more components of abridge formed between two adjacent or non-adjacent amino acids, unnatural amino acids or non-amino acids in a polypeptide. Bridging moieties may be of any size or composition. In some embodiments, bridging moieties may comprise one or more chemical bonds between two adjacent or non-adjacent amino acids, unnatural amino acids, non-amino acid residues or combinations thereof. In some embodiments, such chemical bonds may be between one or more functional groups on adjacent or non-adjacent amino acids, unnatural amino acids, non-amino acid residues or combinations thereof. Bridging moieties may include one or more of an amide bond (lactam), disulfide bond, thioether bond, aromatic ring, triazole ring, and hydrocarbon chain. In some embodiments, bridging moieties include an amide bond between an amine functionality and a carboxylate functionality, each present in an amino acid, unnatural amino acid or non-amino acid residue side chain. In some embodiments, the amine or carboxylate functionalities are part of a non-amino acid residue or unnatural amino acid residue.

C5 inhibitor polypeptides may be cyclized through the carboxy terminus, the amino terminus, or through any other convenient point of attachment, such as, for example, through the sulfur of a cysteine (e.g., through the formation of disulfide bonds between two cysteine residues in a sequence) or any side-chain of an amino acid residue. Further linkages forming cyclic loops may include, but are not limited to, maleimide linkages, amide linkages, ester linkages, ether linkages, thiol ether linkages, hydrazone linkages, or acetamide linkages.

In some embodiments, cyclic C5 inhibitor polypeptides of the invention are formed using a lactam moiety. Such cyclic polypeptides may be formed, for example, by synthesis on a solid support Wang resin using standard Fmoc chemistry. In some cases, Fmoc-ASP(allyl)-OH and Fmoc-LYS(alloc)-OH are incorporated into polypeptides to serve as precursor monomers for lactam bridge formation.

C5 inhibitor polypeptides of the invention may be peptidomimetics. A "peptidomimetic" or "polypeptide mimetic" is a polypeptide in which the molecule contains structural elements that are not found in natural polypeptides (i.e., polypeptides comprised of only the 20 proteinogenic amino acids). In some embodiments, peptidomimetics are capable of recapitulating or mimicking the biological action(s) of a natural peptide. A peptidomimetic may differ in many ways from natural polypeptides, for example through changes in backbone structure or through the presence of amino acids that do not occur in nature. In some cases, peptidomimetics may include amino acids with side chains that are not found among the known 20 proteinogenic amino acids; non-polypeptide-based bridging moieties used to effect cyclization between the ends or internal portions of the molecule; substitutions of the amide bond hydrogen moiety by methyl groups (N-methylation) or other alkyl groups; replacement of a peptide bond with a chemical group or bond that is resistant to chemical or enzymatic treatments; N- and C-terminal modifications; and/or conjugation with a non-peptidic extension (such as polyethylene glycol, lipids, carbohydrates, nucleosides, nucleotides, nucleoside bases, various small molecules, or phosphate or sulfate groups).

As used herein, the term "amino acid" includes the residues of the natural amino acids as well as unnatural amino acids. The 20 natural proteinogenic amino acids are identified and referred to herein by either the one-letter or three-letter designations as follows: aspartic acid (Asp:D), isoleucine (Ile:I), threonine (Thr:T), leucine (Leu:L), serine (Ser:S), tyrosine (Tyr:Y), glutamic acid (Glu:E), phenylalanine (Phe:F), proline (Pro:P), histidine (His:H), glycine (Gly:G), lysine (Lys:K), alanine (Ala:A), arginine (Arg:R), cysteine (Cys:C), tryptophan (Trp:W), valine (Val:V), glutamine (Gln:Q) methionine (Met:M), asparagine (Asn:N). Naturally occurring amino acids exist in their levorotary (L) stereoisomeric forms. Amino acids referred to herein are L-stereoisomers except where otherwise indicated. The term "amino acid" also includes amino acids bearing a conventional amino protecting group (e.g. acetyl or benzyloxycarbonyl), as well as natural and unnatural amino acids protected at the carboxy terminus (e.g., as a (C1-C6) alkyl, phenyl or benzyl ester or amide; or as an alpha-methylbenzyl amide). Other suitable amino and carboxy protecting groups are known to those skilled in the art (See for example, Greene, T. W.; Wutz, P. G. M., Protecting Groups In Organic Synthesis; second edition, 1991, New York, John Wiley & sons, Inc., and documents cited therein, the contents of each of which are herein incorporated by reference in their entirety). Polypeptides and/or polypeptide compositions of the present invention may also include modified amino acids.

"Unnatural" amino acids have side chains or other features not present in the 20 naturally-occurring amino acids listed above and include, but are not limited to: N-methyl amino acids, N-alkyl amino acids, alpha, alpha substituted amino acids, beta-amino acids, alpha-hydroxy amino acids, D-amino acids, and other unnatural amino acids known in the art (See, e.g., Josephson et al., (2005) J. Am. Chem. Soc. 127: 11727-11735; Forster, A. C. et al. (2003) Proc. Natl. Acad. Sci. USA 100: 6353-6357; Subtelny et al., (2008) J. Am. Chem. Soc. 130: 6131-6136; Hartman, M. C. T. et al. (2007) PLoS ONE 2:e972; and Hartman et al., (2006) Proc. Natl. Acad. Sci. USA 103:4356-4361). Further unnatural amino acids useful for the optimization of polypeptides and/or polypeptide compositions of the present invention include, but are not limited to 1,2,3,4-tetrahydroisoquinoline-1-carboxylic acid, 1-amino-2,3-hydro-1H-indene-1-carboxylic acid, homolysine, homoarginine, homoserine, 2-aminoadipic acid, 3-aminoadipic acid, beta-alanine, aminopropionic acid, 2-aminobutyric acid, 4-aminobutyric acid, 5-aminopentanoic acid, 5-aminohexanoic acid, 6-aminocaproic acid, 2-aminoheptanoic acid, 2-aminoisobutyric acid, 3-aminoisobutyric acid, 2-aminopimelic acid, desmosine, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylpentylglycine, naphthylalanine, ornithine, pentylglycine, thioproline, norvaline, tert-butylglycine, phenylglycine, azatryptophan, 5-azatryptophan, 7-azatryptophan, 4-fluorophenylalanine, penicillamine, sarcosine, homocysteine, 1-aminocyclopropanecarboxylic acid, 1-aminocyclobutanecarboxylic acid, 1-aminocyclopentanecarboxylic acid, 1-aminocyclohexanecarboxylic acid, 4-amino-tetrahydro-2H-pyran-4-carboxylic acid, (S)-2-amino-3-(1H-tetrazol-5-yl)propanoic acid, cyclopentylglycine, cyclohexylglycine, cyclopropylglycine, η-ω-methyl-arginine, 4-chlorophenylalanine, 3-chlorotyrosine, 3-fluorotyrosine, 5-fluorotryptophan, 5-chlorotryptophan, citrulline, 4-chloro-homophenylalanine, homophenylalanine, 4-aminomethyl-phenylalanine, 3-aminomethyl-phenylalanine, octylglycine, norleucine, tranexamic acid, 2-amino pentanoic acid, 2-amino hexanoic acid, 2-amino heptanoic acid, 2-amino octanoic acid, 2-amino nonanoic acid, 2-amino decanoic acid, 2-amino undecanoic acid, 2-amino dodecanoic acid, aminovaleric acid, and 2-(2-aminoethoxy)acetic acid, pipecolic acid, 2-carboxy azetidine, hexafluoroleucine, 3-Fluorovaline, 2-amino-4,4-difluoro-3-methylbutanoic acid, 3-fluoro-isoleucine, 4-fluoroisoleucine, 5-luoroisoleucine, 4-methylphenylglycine, 4-ethyl-phenylglycine, 4-isopropyl-phenylglycine, (S)-2-amino-5-azidopentanoic acid (also referred to herein as "X02"), (S)-2-aminohept-6-enoic acid (also referred to herein as "X30"), (S)-2-aminopent-4-ynoic acid (also referred to herein as "X31"), (S)-2-amino-pent-4-enoic acid (also referred to herein as "X12"), (S)-2-amino-5-(3-methylguanidino) pentanoic acid, (S)-2-amino-3-(4-(aminomethyl)phenyl)propanoic acid, (S)-2-amino-3-(3-(aminomethyl)phenyl)propanoic acid, (S)-2-amino-4-(2-aminobenzo[d]oxazol-5-yl)butanoic acid, (S)-leucinol, (S)-valinol, (S)-tert-leucinol, (R)-3-methylbutan-2-amine, (S)-2-methyl-1-phenylpropan-1-amine, and (S)—N,2-dimethyl-1-(pyridin-2-yl)propan-1-amine, (S)-2-amino-3-(oxazol-2-yl)propanoic acid, (S)-2-amino-3-(oxazol-5-yl)propanoic acid, (S)-2-amino-3-(1,3,4-oxadiazol-2-yl)propanoic acid, (S)-2-amino-3-(1,2,4-oxadiazol-3-yl)propanoic acid, (S)-2-amino-3-(5-fluoro-1H-indazol-3-yl)propanoic acid, and (S)-2-amino-3-(1H-indazol-3-yl)propanoic acid, (S)-2-amino-3-(oxazol-2-yl)butanoic acid, (S)-2-amino-3-(oxazol-5-yl) butanoic acid, (S)-2-amino-3-(1,3,4-oxadiazol-2-yl) butanoic acid, (S)-2-amino-3-(1,2,4-oxadiazol-3-yl) butanoic acid, (S)-2-amino-3-(5-fluoro-1H-indazol-3-yl) butanoic acid, and (S)-2-amino-3-(1H-indazol-3-yl) butanoic acid, 2-(2'MeOphenyl)-2-amino acetic acid, tetrahydro 3-isoquinolinecarboxylic acid and stereoisomers thereof (including, but not limited, to D and L isomers).

Additional unnatural amino acids that are useful in the optimization of polypeptides or polypeptide compositions of the invention include but are not limited to fluorinated amino acids wherein one or more carbon bound hydrogen atoms are replaced by fluorine. The number of fluorine atoms included can range from 1 up to and including all of the hydrogen atoms. Examples of such amino acids include but are not limited to 3-fluoroproline, 3,3-difluoroproline, 4-fluoroproline, 4,4-difluoroproline, 3,4-difluroproline, 3,3, 4,4-tetrafluoroproline, 4-fluorotryptophan, 5-flurotryptophan, 6-fluorotryptophan, 7-fluorotryptophan, and stereoisomers thereof.

Further unnatural amino acids that are useful in the optimization of polypeptides of the invention include but are not limited to those that are disubstituted at the α-carbon. These include amino acids in which the two substituents on the α-carbon are the same, for example α-amino isobutyric acid, and 2-amino-2-ethyl butanoic acid, as well as those where the substituents are different, for example α-methylphenylglycine and α-methylproline. Further the substituents on the α-carbon may be taken together to form a ring, for example 1-aminocyclopentanecarboxylic acid, 1-aminocyclobutanecarboxylic acid, 1-aminocyclohexanecarboxylic acid, 3-aminotetrahydrofuran-3-carboxylic acid, 3-aminotetrahydropyran-3-carboxylic acid, 4-aminotetrahydropyran-4-carboxylic acid, 3-aminopyrrolidine-3-carboxylic acid, 3-aminopiperidine-3-carboxylic acid, 4-aminopiperidinnne-4-carboxylix acid, and stereoisomers thereof.

Additional unnatural amino acids that are useful in the optimization of polypeptides or polypeptide compositions of the invention include but are not limited to analogs of tryptophan in which the indole ring system is replaced by another 9 or 10 membered bicyclic ring system comprising 0, 1, 2, 3 or 4 heteroatoms independently selected from N, O, or S. Each ring system may be saturated, partially unsaturated, or fully unsaturated. The ring system may be substituted by 0, 1, 2, 3, or 4 substituents at any substitutable atom. Each substituent may be independently selected from H, F, Cl, Br, CN, COOR, CONRR', oxo, OR, NRR'. Each R and R' may be independently selected from H, C1-C20 alkyl, or C1-C20 alkyl-O—C1-20 alkyl.

In some embodiments, analogs of tryptophan (also referred to herein as "tryptophan analogs") may be useful in the optimization of polypeptides or polypeptide compositions of the invention. Tryptophan analogs may include, but are not limited to 5-fluorotryptophan [(5-F)W], 5-methyl-O-tryptophan [(5-MeO)W], 1-methyltryptophan [(1-Me-W) or (1-Me)W], D-tryptophan (D-Trp), azatryptophan (including, but not limited to 4-azatryptophan, 7-azatryptophan and 5-azatryptophan,) 5-chlorotryptophan, 4-fluorotryptophan, 6-fluorotryptophan, 7-fluorotryptophan, and stereoisomers thereof. Except where indicated to the contrary, the term "azatryptophan" and its abbreviation, "azaTrp," as used herein, refer to 7-azatryptophan.

Modified amino acid residues useful for the optimization of polypeptides and/or polypeptide compositions of the present invention include, but are not limited to those which are chemically blocked (reversibly or irreversibly); chemically modified on their N-terminal amino group or their side chain groups; chemically modified in the amide backbone, as for example, N-methylated, D (unnatural amino acids) and L (natural amino acids) stereoisomers; or residues wherein the side chain functional groups are chemically modified to another functional group. In some embodiments, modified amino acids include without limitation, methionine sulfoxide; methionine sulfone; aspartic acid-(beta-methyl ester), a modified amino acid of aspartic acid; N-ethylglycine, a modified amino acid of glycine; alanine carboxamide; and/or a modified amino acid of alanine. Unnatural amino acids may be purchased from Sigma-Aldrich (St. Louis, Mo.), Bachem (Torrance, Calif.) or other suppliers. Unnatural amino acids may further include any of those listed in Table 2 of US patent publication US 2011/0172126, the contents of which are incorporated herein by reference in their entirety.

The present invention contemplates variants and derivatives of polypeptides presented herein. These include substitutional, insertional, deletional, and covalent variants and derivatives. As used herein, the term "derivative" is used synonymously with the term "variant" and refers to a molecule that has been modified or changed in any way relative to a reference molecule or starting molecule.

Polypeptides of the invention may include any of the following components, features, or moieties, for which abbreviations used herein include: "Ac" and "NH2" indicate acetyl and amidated termini, respectively; "Nvl" stands for norvaline; "Phg" stands for phenylglycine; "Tbg" stands for tert-butylglycine; "Chg" stands for cyclohexylglycine; "(N-Me)X" stands for the N-methylated form of the amino acid indicated by the letter or three letter amino acid code in place of variable "X" written as N-methyl-X [e.g. (N-Me)D or (N-Me)Asp stand for the N-methylated form of aspartic acid or N-methyl-aspartic acid]; "azaTrp" stands for azatryptophan; "(4-F)Phe" stands for 4-fluorophenylalanine; "Tyr (OMe)" stands for O-methyl tyrosine, "Aib" stands for amino isobutyric acid; "(homo)F" or "(homo)Phe" stands for homophenylalanine; "(2-OMe)Phg" refers to 2-O-methylphenylglycine; "(5-F)W" refers to 5-fluorotryptophan; "D-X" refers to the D-stereoisomer of the given amino acid "X" [e.g. (D-Chg) stands for D-cyclohexylglycine]; "(5-MeO)W" refers to 5-methyl-O-tryptophan; "homoC" refers to homocysteine; "(1-Me-W)" or "(1-Me)W" refers to 1-methyltryptophan; "Nle" refers to norleucine; "Tiq" refers to a tetrahydroisoquinoline residue; "Asp(T)" refers to (S)-2-amino-3-(1H-tetrazol-5-yl)propanoic acid; "(3-Cl-Phe)" refers to 3-chlorophenylalanine; "[(N-Me-4-F)Phe]" or "(N-Me-4-F)Phe" refers to N-methyl-4-fluorophenylalanine; "(m-Cl-homo)Phe" refers to meta-chloro homophenylalanine; "(des-amino)C" refers to 3-thiopropionic acid; "(alpha-methyl)D" refers to alpha-methyl L-aspartic acid; "2Nal" refers to 2-naphthylalanine; "(3-aminomethyl)Phe" refers to 3-aminomethyl-L-phenylalanine; "Cle" refers to cycloleucine; "Ac-Pyran" refers to 4-amino-tetrahydropyran-4-carboxylic acid; "(Lys-C16)" refers to N-ε-palmitoyl lysine; "(Lys-C12)" refers to N-ε-lauryl lysine; "(Lys-C10)" refers to N-ε-capryl lysine; "(Lys-C8)" refers to N-ε-caprylic lysine; "[xXylyl(y,z)]" refers to the xylyl bridging moiety between two thiol containing amino acids where x may be m, p or o to indicate the use of meta-, para- or ortho-dibromoxylenes (respectively) to generate bridging moieties and the numerical identifiers, y and z, place the amino acid position within the polypeptide of the amino acids participating in the cyclization; "[cyclo(y,z)]" refers to the formation of a bond between two amino acid residues where the numerical identifiers, y and z, place the position of the residues participating in the bond; "[cyclo-olefinyl(y,z)]" refers to the formation of a bond between two amino acid residues by olefin metathesis where the numerical identifiers, y and z, place the position of the residues participating in the bond; "[cyclo-thioalkyl(y,z)]" refers to the formation of a thioether bond between two amino acid residues where the numerical identifiers, y and z, place the position of the residues participating in the bond; "[cyclo-triazolyl(y,z)]" refers to the formation of a triazole ring between two amino acid residues where the numerical identifiers, y and z, place the position of the residues participating in the bond. "B20" refers to N-ε-(PEG2-γ-glutamic acid-N-α-octadecanedioic acid) lysine [also known as (1S,28S)-1-amino-7,16,25,30-tetraoxo-9,12,18,21-tetraoxa-6,15,24,29-tetraazahexatetracontane-1,28,46-tricarboxylic acid.]

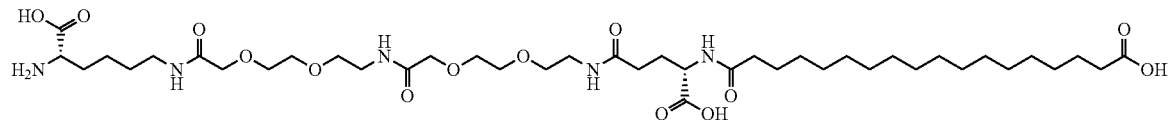

B20

"B28" refers to N-ε-(PEG24-γ-glutamic acid-N-α-hexadecanoyl)lysine.

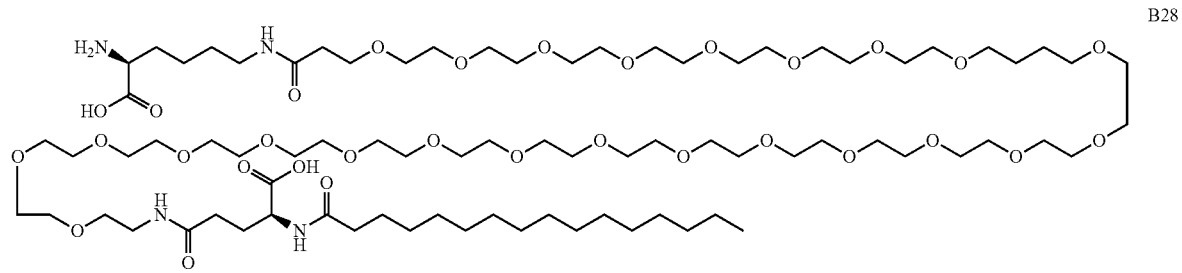 [SMILES: CCCCCCCCCCCCCCCC(=O)N[C@@H](CCC(=O)NCCOCCOCCOCCOCCOCCOCCOCCOCCOCCOCCOCCOCCOCCOCCOCCOCCCCOCCOCCOCCOCCOCCOCCOCCOCCC(=O)NCCCC[C@H](N)C(=O)O)C(=O)O]

B28

"K14" refers to N-ε-1-(4,4-dimethyl-2,6-dioxocyclohex-1-ylidene)-3-methylbutyl-L-lysine. All other symbols refer to the standard one-letter amino acid code.

Some C5 inhibitor polypeptides comprise from about 5 amino acids to about 10 amino acids, from about 6 amino acids to about 12 amino acids, from about 7 amino acids to about 14 amino acids, from about 8 amino acids to about 16 amino acids, from about 10 amino acids to about 18 amino acids, from about 12 amino acids to about 24 amino acids, or from about 15 amino acids to about 30 amino acids. In some cases, C5 inhibitor polypeptides comprise at least 30 amino acids.

Some C5 inhibitors of the invention include a C-terminal lipid moiety. Such lipid moieties may include fatty acyl groups (e.g., saturated or unsaturated fatty acyl groups). In some cases, the fatty acyl group may be a palmitoyl group.

C5 inhibitors having fatty acyl groups may include one or more molecular linkers joining the fatty acids to the peptide. Such molecular linkers may include amino acid residues. In some cases, L-γ glutamic acid residues may be used as molecular linkers. In some cases, molecular linkers may include one or more polyethylene glycol (PEG) linkers. PEG linkers of the invention may include from about 1 to about 5, from about 2 to about 10, from about 4 to about 20, from about 6 to about 24, from about 8 to about 32, or at least 32 PEG units.

C5 inhibitors of the invention may have molecular weights of from about 200 g/mol to about 600 g/mol, from about 500 g/mol to about 2000 g/mol, from about 1000 g/mol to about 5000 g/mol, from about 3000 g/mol to about 4000 g/mol, from about 2500 g/mol to about 7500 g/mol, from about 5000 g/mol to about 10000 g/mol, or at least 10000 g/mol.

In some embodiments, C5 inhibitor polypeptides of the invention include R5000. The core amino acid sequence of R5000 (SEQ ID NO: 1) comprises 15 amino acids (all L-amino acids), including 4 unnatural amino acids (N-methyl-aspartic acid, tert-butylglycine, 7-azatryptophan, and cyclohexylglycine); a lactam bridge between K1 and D6 of the polypeptide sequence; and a C-terminal lysine reside with a modified side chain, forming a N-ε-(PEG24-γ-glutamic acid-N-α-hexadecanoyl)lysine residue (also referred to herein as "B28"). The C-terminal lysine side chain modification includes a polyethyleneglycol (PEG) spacer (PEG24), with the PEG24 being attached to an L-γ glutamic acid residue that is derivatized with a palmitoyl group.

In some embodiments, the present invention includes variants of R5000. In some R5000 variants, the C-terminal lysine side chain moiety may be altered. In some cases, the PEG24 spacer (having 24 PEG subunits) of the C-terminal lysine side chain moiety may include fewer or additional PEG subunits. In other cases, the palmitoyl group of the C-terminal lysine side chain moiety may be substituted with another saturated or unsaturated fatty acid. In further cases, the L-γ glutamic acid linker of the C-terminal lysine side chain moiety (between PEG and acyl groups) may be substituted with an alternative amino acid or non-amino acid linker.

In some embodiments, R5000 variants may include modifications to the core polypeptide sequence in R5000 that may be used in combination with one or more of the cyclic or C-terminal lysine side chain moiety features of R5000. Such variants may have at least 50%, at least 55%, at least 65%, at least 70%, at least 80%, at least 85%, at least 90%, or at least 95% sequence identity to the core polypeptide sequence of SEQ ID NO: 1. In some cases, R5000 variants may be cyclized by forming lactam bridges between amino acids other than those used in R5000.

C5 inhibitors of the invention may be developed or modified to achieve specific binding characteristics. Inhibitor binding may be assessed by determining rates of association and/or dissociation with a particular target. In some cases, compounds demonstrate strong and rapid association with a target combined with a slow rate of dissociation. In some embodiments, C5 inhibitors of the invention demonstrate strong and rapid association with C5. Such inhibitors may further demonstrate slow rates of dissociation with C5.

C5 inhibitors of the invention that bind to C5 complement protein, may bind to C5 complement protein with an equilibrium dissociation constant ($K_D$) of from about 0.001 nM to about 0.01 nM, from about 0.005 nM to about 0.05 nM, from about 0.01 nM to about 0.1 nM, from about 0.05 nM to about 0.5 nM, from about 0.1 nM to about 1.0 nM, from about 0.5 nM to about 5.0 nM, from about 2 nM to about 10 nM, from about 8 nM to about 20 nM, from about 15 nM to about 45 nM, from about 30 nM to about 60 nM, from about 40 nM to about 80 nM, from about 50 nM to about 100 nM, from about 75 nM to about 150 nM, from about 100 nM to about 500 nM, from about 200 nM to about 800 nM, from about 400 nM to about 1,000 nM or at least 1,000 nM.

In some embodiments, C5 inhibitors of the invention block the formation or generation of C5a from C5. In some case, formation or generation of C5a is blocked following activation of the alternative pathway of complement activation. In some cases, C5 inhibitors of the invention block the formation of the membrane attack complex (MAC). Such MAC formation inhibition may be due to C5 inhibitor binding to C5b subunits. C5 inhibitor binding to C5b subunits may prevent C6 binding, resulting in blockage of MAC formation. In some embodiments, this MAC formation inhibition occurs after activation of the classical, alternative, or lectin pathways.

C5 inhibitors of the invention may be synthesized using chemical processes. In some cases, such synthesis eliminates risks associated with the manufacture of biological products in mammalian cell lines. In some cases, chemical synthesis may be simpler and more cost-effective than biological production processes.

Isotopic Variations

Polypeptides of the present invention may comprise one or more atoms that are isotopes. As used herein, the term "isotope" refers to a chemical element that has one or more additional neutrons. In one embodiment, polypeptides of the present invention may be deuterated. As used herein, the term "deuterated" refers to a substance that has had one or more hydrogen atoms replaced by deuterium isotopes. Deuterium isotopes are isotopes of hydrogen. The nucleus of hydrogen contains one proton while deuterium nuclei contain both a proton and a neutron. Compounds and pharmaceutical compositions of the present invention may be deuterated in order to change a physical property, such as stability, or to allow them to be used in diagnostic and experimental applications.

II. Methods of Use

Provided herein are methods of modulating complement activity using compounds and/or compositions of the invention.

Therapeutic Indications

An important component of all immune activity (innate and adaptive) is the ability of the immune system to distinguish between self and non-self cells. Pathology arises when the immune system is unable to make this distinction. In the case of the complement system, vertebrate cells express inhibitory proteins that protect them from the effects of the complement cascade and this ensures that the complement system is directed against microbial pathogens. Many complement-related disorders and diseases are associated with abnormal destruction of self-cells by the complement cascade.

Methods of the invention include methods of treating complement-related disorders with compounds and compositions of the invention. A "complement-related disorder," as referred to herein, may include any condition related to dysfunction of the complement system, e.g., cleavage or processing of a complement component such as C5.

In some embodiments, methods of the invention include methods of inhibiting complement activity in a subject. In some cases, the percentage of complement activity inhibited in a subject may be at least 10%, at least 20%, at least 30%, at least 40%, at least 50%, at least 60%, at least 70%, at least 80%, at least, 85%, at least 90%, at least 95%, at least 96%, at least 97%, at least 98%, at least 99%, at least 99.5%, or at least 99.9%. In some cases, this level of inhibition and/or maximum inhibition of complement activity may be achieved by from about 1 hour after an administration to about 3 hours after an administration, from about 2 hours after an administration to about 4 hours after an administration, from about 3 hours after an administration to about 10 hours after an administration, from about 5 hours after an administration to about 20 hour after an administration, or from about 12 hours after an administration to about 24 hours after an administration. Inhibition of complement activity may continue throughout a period of at least 1 day, of at least 2 days, of at least 3 days, of at least 4 days, of at least 5 days, of at least 6 days, of at least 7 days, of at least 2 weeks, of at least 3 weeks, or at least 4 weeks. In some cases, this level of inhibition may be achieved through daily administration. Such daily administration may include administration for at least 2 days, for at least 3 days, for at least 4 days, for at least 5 days, for at least 6 days, for at least 7 days, for at least 2 weeks, for at least 3 weeks, for at least 4 weeks, for at least 2 months, for at least 4 months, for at least 6 months, for at least 1 year, or for at least 5 years. In some cases, subjects may be administered compounds or compositions of the present disclosure for the life of such subjects.

In some embodiments, methods of the invention include methods of inhibiting C5 activity in a subject. "C5-dependent complement activity" or "C5 activity," as used herein refers to activation of the complement cascade through cleavage of C5, the assembly of downstream cleavage products of C5, or any other process or event attendant to, or resulting from, the cleavage of C5. In some cases, the percentage of C5 activity inhibited in a subject may be at least 10%, at least 20%, at least 30%, at least 40%, at least 50%, at least 60%, at least 70%, at least 80%, at least, 85%, at least 90%, at least 95%, at least 96%, at least 97%, at least 98%, at least 99%, at least 99.5%, or at least 99.9%.

In some embodiments, methods of the invention may include methods of inhibiting hemolysis by administering one or more compounds or compositions of the invention to a subject or patient in need thereof. According to some such methods, hemolysis may be reduced by from about 25% to about 99%. In other embodiments, hemolysis is reduced by from about 10% to about 40%, from about 25% to about 75%, from about 30% to about 60%, from about 50% to about 90%, from about 75% to about 95%, from about 90% to about 99%, or from about 97% to about 99.5%. In some cases, hemolysis is reduced by at least 50%, 60%, 70%, 80%, 90% or 95%.

According to some methods, the percent inhibition of hemolysis is from about ≥90% to about ≥99% (e.g., ≥91%, ≥92%, ≥93%, ≥94%, 95%, ≥96%, ≥97%, ≥98%). In some cases, this level of inhibition and/or maximum inhibition of hemolysis may be achieved by from about 1 hour after an administration to about 3 hours after an administration, from about 2 hours after an administration to about 4 hours after an administration, from about 3 hours after an administration to about 10 hours after an administration, from about 5 hours after an administration to about 20 hour after an administration or from about 12 hours after an administration to about 24 hours after an administration. Inhibition of hemolysis activity levels may continue throughout a period of at least 1 day, of at least 2 days, of at least 3 days, of at least 4 days, of at least 5 days, of at least 6 days, of at least 7 days, of at least 2 weeks, of at least 3 weeks, or at least 4 weeks. In some cases, this level of inhibition may be achieved through daily administration. Such daily administration may include administration for at least 2 days, for at least 3 days, for at least 4 days, for at least 5 days, for at least 6 days, for at least 7 days, for at least 2 weeks, for at least 3 weeks, for at least 4 weeks, for at least 2 months, for at least 4 months, for at least 6 months, for at least 1 year, or for at least 5 years. In some cases, subjects may be administered compounds or compositions of the present disclosure for the life of such subjects.

C5 inhibitors of the invention may be used to treat one or more indications, wherein few or no adverse effects occur as a result of the C5 inhibitor treatment. In some cases, no adverse cardiovascular, respiratory, and/or central nervous system (CNS) effects occur. In some cases, no changes in heart rate and/or arterial blood pressure occur. In some cases, no changes to respiratory rate, tidal volume, and/or minute volume occur.

By "lower" or "reduce" in the context of a disease marker or symptom is meant a significant decrease in such level, often statistically significant. The decrease can be, for example, at least 10%, at least 20%, at least 30%, at least 40% or more, and is preferably down to a level accepted as within the range of normal for an individual without such disorder.

By "increase" or "raise" in the context of a disease marker or symptom is meant a significant rise in such level, often statistically significant. The increase can be, for example, at least 10%, at least 20%, at least 30%, at least 40% or more, and is preferably up to a level accepted as within the range of normal for an individual without such disorder.

A treatment or preventive effect is evident when there is a significant improvement, often statistically significant, in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given compound or composition can also be judged using an experimental animal model for the given disease as known in the art. When using an experimental animal model, efficacy of treatment is evidenced when a statistically significant modulation in a marker or symptom is observed.

Paroxysmal Nocturnal Hemoglobinuria

In some embodiments, provided herein are methods of treating paroxysmal nocturnal hemoglobinuria (PNH) with compounds or compositions, e.g., pharmaceutical compositions, of the invention. PNH is a rare complement-related disorder caused by an acquired mutation in the phosphatidylinositol glycan anchor biosynthesis, class A (PIG-A) gene that originates from a multipotent hematopoietic stem cell (Pu, J. J. et al., Clin Transl Sci. 2011 June; 4(3):219-24). PNH is characterized by bone marrow disorder, hemolytic anemia and thrombosis. The PIG-A gene product is necessary for the production of a glycolipid anchor, glycosylphosphatidylinositol (GPI), utilized to tether proteins to the plasma membrane. Two complement-regulatory proteins responsible for protecting cells from lytic activity of the terminal complement complex, CD55 (decay accelerating factor) and CD59 (membrane inhibitor of reactive lysis), become nonfunctional in the absence of GPI. This leads to C5 activation and accumulation of specific complement proteins on the surface of red blood cells (RBCs) leading to complement-mediated destruction of these cells.

Patient with PNH initially present with hemoglobinuria, abdominal pain, smooth muscle dystonias, and fatigue, e.g., PNH-related symptoms or disorders. PNH is also characterized by intravascular hemolysis (the primary clinical manifestation of the disease) and venous thrombosis. Venous thrombosis may occur in unusual sites, including, but not limited to hepatic, mesenteric, cerebral, and dermal veins. (Parker, C. et al., 2005. Blood. 106: 3699-709 and Parker, C. J., 2007. Exp Hematol. 35: 523-33). Currently, eculizumab (SOLIRIS®, Alexion Pharmaceuticals, Cheshire, Conn.), a C5 inhibitor monoclonal antibody, is the only approved treatment for PNH.

Treatment with eculizumab results in an adequate control of intravascular hemolysis in most PNH patients (Schrezenmeier, H. et al., 2014. Haematologica. 99: 922-9). However, Nishimura and colleagues have described 11 patients in Japan (3.2% of patients with PNH) who have mutations in the C5 gene that prevent binding of eculizumab to C5 and do not respond to treatment with the antibody (Nishimura, J-I. et al., 2014. N Engl J Med. 370: 632-9). Further, eculizumab is administered every 2 weeks as an IV infusion under the supervision of a healthcare professional, which is inconvenient and poses a burden to patients.

Long-term IV administration has the potential to lead to serious complications such as infections, local thrombosis, hematomas, and progressively reduced venous access. Additionally, eculizumab is a large protein, and is associated with risk of immunogenicity and hypersensitivity. Finally, while eculizumab binds C5 and prevents C5b generation, any C5b generated through incomplete inhibition can initiate MAC formation and cause hemolysis.

The peripheral blood of patients with PNH can vary in the proportions of normal and abnormal cells. The disease is sub-classified according to the International PNH Interest Group based on clinical features, bone marrow characteristics, and the percentage of GPI-AP-deficient polymorphonuclear leukocytes (PMNs). As GPI-AP-deficient red blood cells are more sensitive to destruction in PNH patients, the flow cytometry analysis of PMNs is considered more informative (Parker, C. J., 2012. Curr Opin Hematol. 19: 141-8). Flow cytometry analysis in classic PNH shows 50 to 100% GPI-AP-deficient PMNs.

The hemolytic anemia of PNH is independent of autoantibodies (Coombs negative) and results from uncontrolled activation of the Alternative Pathway (AP) of complement.

In some embodiments, compounds and composition, e.g., pharmaceutical compositions, of the present invention are particularly useful in the treatment of PNH. Such compounds and compositions may include C5 inhibitors (e.g., R5000). C5 inhibitors of the invention, useful for treatment of PNH may, in some cases, block the cleavage of C5 into C5a and C5b. In some cases, C5 inhibitors of the invention may be used as an alternative to eculizumab therapy for PNH. Unlike eculizumab, C5 inhibitors of the invention may bind C5b, preventing C6 binding and subsequent assembly of the C5b-9 MAC.

In some cases, R5000 and compositions thereof may be used to treat PNH in subjects. Such subjects may include subjects that have had adverse effects with, been unresponsive to, demonstrated reduced responsiveness with, or demonstrated resistance to other treatments (e.g., with eculizumab). In some embodiments, treatment with compounds and compositions of the present disclosure may inhibit hemolysis of PNH erythrocytes in a dose dependent manner.

In some embodiments, R5000 is administered in combination with eculizumab in a regimen which may involve parallel or serial treatment.

Based on sequence and structural data, R5000 may be particularly useful for the treatment of PNH in the limited number of patients with mutations in the C5 gene that prevent binding of eculizumab to C5. An example of such patients are those with a single missense C5 heterozygous mutation, c.2654G->A, which predicts the polymorphism p.Arg885His (for a description of this polymorphism, see Nishimura, J. et al., N Engl J Med. 2014. 370(7):632-9, the contents of which are herein incorporated by reference in their entirety). Like eculizumab, R5000 blocks the proteolytic cleavage of C5 into C5a and C5b. Unlike eculizumab, R5000 can also bind to C5b and block association with C6, preventing the subsequent assembly of the MAC. Therefore, advantageously any C5b that arises from incomplete inhibition by R5000 is prevented from binding C6 and completing assembly of the MAC.

In some cases, R5000 is used as a therapeutic alternative to eculizumab for patients with PNH that may offer added efficacy without the inconvenience and liabilities of IV administration and known risks of immunogenicity and hypersensitivity associated with monoclonal antibodies. Further, the serious complications of long-term IV administration, such as infections, loss of venous access, local thrombosis, and hematomas, may be overcome by R5000 given by subcutaneous (SC) injection.

Inflammatory Indications

In some embodiments, compounds and compositions, e.g., pharmaceutical compositions, of the invention may be used to treat subjects with diseases, disorders and/or conditions related to inflammation. Inflammation may be upregulated during the proteolytic cascade of the complement system. Although inflammation may have beneficial effects, excess inflammation may lead to a variety of pathologies (Markiewski et al. 2007. Am J Pathol. 17: 715-27). Accordingly, compounds and compositions of the present invention may be used to reduce or eliminate inflammation associated with complement activation.

Sterile Inflammation

In some embodiments, compounds and compositions, e.g., pharmaceutical compositions, of the present invention may be used to treat, prevent or delay development of sterile inflammation. Sterile inflammation is inflammation that occurs in response to stimuli other than infection. Sterile inflammation may be a common response to stress such as genomic stress, hypoxic stress, nutrient stress or endoplasmic reticulum stress caused by a physical, chemical, or metabolic noxious stimuli. Sterile inflammation may contribute to pathogenesis of many diseases such as, but not limited to, ischemia-induced injuries, rheumatoid arthritis, acute lung injuries, drug-induced liver injuries, inflammatory bowel diseases and/or other diseases, disorders or conditions. Mechanism of sterile inflammation and methods and compositions for treatment, prevention and/or delaying of symptoms of sterile inflammation may include any of those taught by Rubartelli et al. in Frontiers in Immunology, 2013, 4:398-99, Rock et al. in Annu Rev Immunol. 2010, 28:321-342 or in U.S. Pat. No. 8,101,586, the contents of each of which are herein incorporated by reference in their entirety.

Systemic Inflammatory Response (SIRS) and Sepsis

In some embodiments, compounds and compositions, e.g., pharmaceutical compositions, of the invention may be used to treat and/or prevent systemic inflammatory response syndrome (SIRS). SIRS is inflammation affecting the whole body. Where SIRS is caused by an infection, it is referred to as sepsis. SIRS may also be caused by non-infectious events such as trauma, injury, burns, ischemia, hemorrhage and/or other conditions. Among negative outcomes associated with SIRS and/or sepsis is multi-organ failure (MOF). Complement inhibition at the C3 level in Gram-negative sepsis significantly protects the organs against *E. coli*-induced progressive MOF, but also hinders bacterial clearance. Compounds and compositions described herein include C5 complement component inhibitors that may be administered to subjects with sepsis to provide the benefits of organ protection without detrimentally altering bacterial clearance.

In some embodiments, the present disclosure provides methods of treating sepsis. Sepsis may be induced by microbial infection. The microbial infection may include at least one Gram-negative infectious agent. As used herein, the term "infectious agent" refers to any entity that invades or otherwise infects a cell, tissue, organ, compartment, or fluid of a sample or subject. In some cases, infectious agents may be bacteria, viruses, or other pathogens. Gram negative infectious agents are Gram-negative bacteria. Gram-negative infectious agents may include, but are not limited to *E. coli*.

Methods of treating sepsis may include the administration of one or more C5 inhibitors to a subject. The C5 inhibitor may be R5000. According to some methods, complement activation may be reduced or prevented. Reduction or prevention of complement activity may be determined by detecting one or more products of complement activity in a subject sample. Such products may include C5 cleavage products (e.g., C5a and C5b) or downstream complexes formed as a result of C5 cleavage (e.g., C5b-9). In some embodiments, the present disclosure provides methods of treating sepsis with R5000, wherein levels of C5a and/or C5b-9 are reduced or eliminated in the subject and/or in at least one sample obtained from the subject. For example, C5a and/or C5b-9 levels may be reduced in subjects administered R5000 (or in samples obtained from such subjects) by from about 0% to about 0.05%, from about 0.01% to about 1%, from about 0.05% to about 2%, from about 0.1% to about 5%, from about 0.5% to about 10%, from about 1% to about 15%, from about 5% to about 25%, from about 10% to about 50%, from about 20% to about 60%, from about 25% to about 75%, from about 50% to about 100% when compared to subjects (or subject samples) not treated with R5000 (including subjects treated with other complement inhibitors) or when compared to the same subject (or subject samples) during a pre-treatment period or an earlier period of treatment.

In some embodiments, C5b-9 levels reduced by R5000 treatment are C5b-9 levels associated with one or more of the classical pathway of complement activation, the alternative pathway of complement activation, and the lectin pathway of complement activation.

In some embodiments, the presence, absence, and/or levels of one or more factors associated with sepsis may be modulated by administering R5000 to a subject with sepsis. The presence or absence of such factors may be determined using assays for their detection. Changes in factor levels may be determined by determining the level of such factors in a subject with sepsis after R5000 treatment and comparing those levels to earlier levels in the same subject (either before R5000 treatment or during one or more earlier periods of treatment) or to levels in subjects that are not treated with R5000 (including subjects with sepsis that receive no treatment or subjects that receive some other form of treatment). Comparisons may be presented by percentage differences in factor levels between R5000 treated subjects and subjects not treated with R5000.

C5 cleavage product may include any proteins or complexes that may result from C5 cleavage. In some cases, C5 cleavage products may include, but are not limited to, C5a and C5b. C5b cleavage product may go on to form a complex with complement proteins C6, C7, C8, and C9 (referred to herein as "C5b-9"). Accordingly, C5 cleavage products that include C5b-9 may be detected and/or quantitated to determine whether complement activity has been reduced or prevented. Detection of C5b-9 deposition may be carried out, for example, through the use of the WIESLAB® ELISA (Euro Diagnostica, Malmo, Sweden) kit. Quantitation of cleavage products may be measured in "complement arbitrary units" (CAU) as described by others (e.g., see Bergseth G et al., 2013. Mol Immunol. 56:232-9, the contents of which are herein incorporated by reference in their entirety).

In some embodiments, treating sepsis with a C5 inhibitor (e.g., R5000) may reduce or prevent C5b-9 production.

According to the present invention, administration of R5000 to a subject may result in modulation of bacterial clearance in the subject and/or in at least one sample obtained from the subject. Bacterial clearance, as referred to herein, is the partial or complete removal/reduction of bacteria from a subject or sample. Clearance may occur by way of killing or otherwise rendering bacteria incapable of growth and/or reproduction. In some cases, bacterial clearance may occur through bacterial lysis and/or immune destruction (e.g., through phagocytosis, bacterial cell lysis, opsonization, etc.). According to some methods, bacterial clearance in subjects treated with C5 inhibitors (e.g., R5000) may have no effect or a beneficial effect on bacterial clearance. This may occur due to the absence of or a decreased effect on C3b levels with C5 inhibition. In some embodiments, methods of treating sepsis with R5000 may avoid interference with C3b-dependent opsonization or enhance C3b-dependent opsonization.

In some cases, bacterial clearance with R5000 treatment may be enhanced in comparison to bacterial clearance in an untreated subject or in a subject treated with another form of complement inhibitor, for example, a C3 inhibitor. In some embodiments, subjects with sepsis that are treated with R5000 may experience 0% to at least 100% enhanced bacterial clearance when compared to bacterial clearance in subjects not treated with R5000 (including subjects treated with other complement inhibitors) or when compared to earlier bacterial clearance levels in the same subject before treatment with R5000 or during an earlier treatment period with R5000. For example, bacterial clearance in subjects treated with R5000 and/or in at least one sample obtained from such subjects may be enhanced by from about 0% to about 0.05%, from about 0.01% to about 1%, from about 0.05% to about 2%, from about 0.1% to about 5%, from about 0.5% to about 10%, from about 1% to about 15%, from about 5% to about 25%, from about 10% to about 50%, from about 20% to about 60%, from about 25% to about 75%, from about 50% to about 100% when compared to subjects not treated with R5000 (including subjects treated with other complement inhibitors) and/or when compared to samples obtained from such subjects or when compared to the same subject during a pre-treatment period or an earlier period of treatment and/or when compared to samples obtained from the same subject during a pre-treatment period or an earlier period of treatment.

Bacterial clearance may be measured in a subject by directly measuring bacterial levels in the subject and/or a subject sample or by measuring one or more indicators of bacterial clearance (e.g., levels of bacterial components released after bacterial lysis). Bacterial clearance levels may then be determined by comparison to a previous measurement of bacterial/indicator levels or to bacterial/indicator levels in a subject receiving no treatment or a different treatment. In some cases, colony forming units (cfu) from collected blood (e.g., to generate cfu/ml of blood) are examined to determine bacterial levels.

In some embodiments, sepsis treatment with R5000 may be carried out with no effect on phagocytosis or without substantial impairment of phagocytosis. This may include neutrophil-dependent and/or monocyte-dependent phagocytosis. Unimpaired or substantially unimpaired phagocytosis with R5000 treatment may be due to limited or non-existent changes to C3b levels with R5000 treatment.

Oxidative burst is a C5a-dependent process, characterized by the production of peroxide by certain cells, particularly macrophages and neutrophils, following challenge by a pathogen (see Mollnes T. E. et al., 2002. Blood 100, 1869-1877, the contents of which are herein incorporated by reference in their entirety).

In some embodiments, oxidative burst may be reduced or prevented in subjects with sepsis after treatment with R5000. This may be due to a decrease in C5a levels with R5000-dependent C5 inhibition. Oxidative burst may be reduced in subjects administered R5000 by from about 0% to about 0.05%, from about 0.01% to about 1%, from about 0.05% to about 2%, from about 0.1% to about 5%, from about 0.5% to about 10%, from about 1% to about 15%, from about 5% to about 25%, from about 10% to about 50%, from about 20% to about 60%, from about 25% to about 75%, from about 50% to about 100% when compared to subjects not treated with R5000 (including subjects treated with other complement inhibitors) or when compared to the same subject during a pre-treatment period or an earlier period of treatment.

Lipopolysaccharide (LPS) is a component of bacterial cell coats that is a known immune stimulator. Complement-dependent bacteriolysis can lead to release of LPS, contributing to inflammatory responses, such as those characteristic of sepsis. In some embodiments, treatment of sepsis with R5000 may reduce LPS levels. This may be due to a decrease in complement-mediated bacteriolysis with inhibition of C5-dependent complement activity. In some embodiments, LPS levels may be reduced or eliminated in subjects administered R5000 (or in samples obtained from such subjects) by from about 0% to about 0.05%, from about 0.01% to about 1%, from about 0.05% to about 2%, from about 0.1% to about 5%, from about 0.5% to about 10%, from about 1% to about 15%, from about 5% to about 25%, from about 10% to about 50%, from about 20% to about 60%, from about 25% to about 75%, from about 50% to about 100% when compared to subjects (or subject samples) not treated with R5000 (including subjects treated with other complement inhibitors) or when compared to the same subject (or subject samples) during a pre-treatment period or an earlier period of treatment.

In some embodiments, LPS levels may be reduced by 100% in subjects (or subject samples) with sepsis that are treated with R5000 as compared to subjects (or subject samples) with sepsis that are not treated with R5000 (including subjects receiving one or more other forms of treatment) or when compared to the same subject (or subject sample) during a pre-treatment period or an earlier period of treatment.

In some embodiments of the present disclosure, sepsis-induced levels of one or more cytokine may be reduced with R5000 treatment. Cytokines include a number of cell signaling molecules that stimulate immune responses to infection. "Cytokine storm" is a dramatic upregulation of at least four cytokines, interleukin (IL)-6, IL-8, monocyte chemoattractant protein-1 (MCP-1), and tumor necrosis factor alpha (TNFα), that may result from bacterial infection and contribute to sepsis. C5a is known to induce the synthesis and activity of these cytokines. Inhibitors of C5, may therefore reduce cytokine levels by reducing levels of C5a. Cytokine levels may be evaluated in subjects or subject samples to evaluate the ability of C5 inhibitors to reduce the levels of one or more inflammatory cytokines upregulated during sepsis. IL-6, IL-8, MCP-1 and/or TNFα levels may be decreased in subjects administered R5000 by from about 0% to about 0.05%, from about 0.01% to about 1%, from about 0.05% to about 2%, from about 0.1% to about 5%, from about 0.5% to about 10%, from about 1% to about 15%, from about 5% to about 25%, from about 10% to about 50%, from about 20% to about 60%, from about 25% to about 75%, from about 50% to about 100% when compared to subjects not treated with R5000 (including subjects treated with other complement inhibitors) or when compared to the same subject during a pre-treatment period or an earlier period of treatment. In some embodiments, IL-6, IL-8, MCP-1, and/or TNFα levels may be reduced by 100% in subjects with sepsis that are treated with R5000 as compared to subjects with sepsis that are not treated with R5000 (including subjects receiving one or more other forms of treatment) or when compared to the same subject during a pre-treatment period or an earlier period of treatment.

One complication associated with sepsis is dysregulation of coagulation and/or fibrinolysis pathways (Levi M., et al., 2013. Seminars in thrombosis and hemostasis 39, 559-66; Rittirsch D., et al., 2008. Nature Reviews Immunology 8, 776-87; and Dempfle C., 2004. A Thromb Haemost. 91(2): 213-24, the contents of each of which are herein incorporated by reference in their entirety). While controlled local activation of these pathways is important for defending against pathogens, systemic, uncontrolled activation may be harmful. Complement activity associated with bacterial infection may promote coagulation and/or fibrinolysis dysregulation due to increased host cell and tissue damage associated with MAC formation. In some embodiments, treatment of sepsis with R5000 may normalize coagulation and/or fibrinolysis pathways.

Dysregulation of coagulation and/or fibrinolysis associated with sepsis may include disseminated intravascular coagulation (DIC). DIC is a condition that results in tissue and organ damage due to activation of coagulation and blood clot formation in small blood vessels. This activity reduces blood flow to tissues and organs and consumes blood factors necessary for coagulation in the rest of the body. The absence of these blood factors in the blood stream may lead to uncontrolled bleeding in other parts of the body. In some embodiments, treatment of sepsis with R5000 may reduce or eliminate DIC.

Coagulation dysfunction associated with sepsis may be detected by measuring the activated partial thromboplastin time (APTT) and/or prothrombin time (PT). These are tests performed on plasma samples to determine whether coagulation factor levels are low. In subjects with DIC, APTT and/or PT are prolonged due to reduced levels of coagulation factors. In some embodiments, subject treatment of sepsis with R5000 may lower and/or normalize APTT and/or PT in samples obtained from treated subjects.

Coagulation dysfunction associated with sepsis may further be evaluated through analysis of thrombin-antithrombin (TAT) complex levels and/or leukocyte expression of Tissue Factor (TF) mRNA. Increased levels of TAT complex and leukocyte expression of TF mRNA are associated with coagulation dysfunction and are consistent with DIC. In some embodiments, treatment of sepsis with R5000 may result in a reduction in TAT levels and/or leukocyte TF mRNA levels of from about 0.005% to about 0.05%, from about 0.01% to about 1%, from about 0.05% to about 2%, from about 0.1% to about 5%, from about 0.5% to about 10%, from about 1% to about 15%, from about 5% to about 25%, from about 10% to about 50%, from about 20% to about 60%, from about 25% to about 75%, from about 50% to about 100% when compared to subjects not treated with R5000 (including subjects treated with other complement inhibitors) or when compared to the same subject during a pre-treatment period or an earlier period of treatment. In some embodiments, TAT levels and/or leukocyte TF mRNA levels may be reduced by 100% in subjects with sepsis that are treated with R5000 as compared to subjects with sepsis that are not treated with R5000 (including subjects receiving one or more other forms of treatment) or when compared to the same subject during a pre-treatment period or an earlier period of treatment.

Factor XII is a factor important for normal coagulation in plasma. Factor XII levels may be decreased in plasma samples taken from subjects with coagulation dysfunction (e.g., DIC) due to consumption of Factor XII associated with coagulation in small blood vessels. In some embodiments, sepsis treatment with R5000 may reduce Factor XII consumption. Accordingly, Factor XII levels may be increased in plasma samples taken from subjects with sepsis after R5000 treatment. Factor XII levels may be increased in plasma samples by from about 0.005% to about 0.05%, from about 0.01% to about 1%, from about 0.05% to about 2%, from about 0.1% to about 5%, from about 0.5% to about 10%, from about 1% to about 15%, from about 5% to about 25%, from about 10% to about 50%, from about 20% to about 60%, from about 25% to about 75%, from about 50% to about 100% when compared to subjects not treated with R5000 (including subjects treated with other complement inhibitors) or when compared to plasma samples taken from the same subject during a pre-treatment period or an earlier period of treatment. In some embodiments, Factor XII levels may be increased by 100% in plasma samples from subjects with sepsis that are treated with R5000 as compared to plasma samples from subjects with sepsis that are not treated with R5000 (including subjects receiving one or more other forms of treatment) or when compared to plasma samples taken from the same subject during a pre-treatment period or an earlier period of treatment.

Fibrinolysis is the breakdown of fibrin due to enzymatic activity, a process critical for clot formation. Fibrinolysis dysregulation may occur in severe sepsis and is reported to affect normal clotting in baboons challenged with E. coli (P. de Boer J. P., et al., 1993. Circulatory shock. 39, 59-67, the contents of which are herein incorporated by reference in their entirety). Plasma indicators of sepsis-dependent fibrinolysis dysfunction (including, but not limited to fibrinolysis dysfunction associated with DIC) may include, but are not limited to decreased fibrinogen levels (indicating a reduced ability to form fibrin clots), increased tissue plasminogen activator (tPA) levels, increased plasminogen activator inhibitor type 1 (PAI-1) levels, increased plasmin-antiplasmin (PAP) levels, increased fibrinogen/fibrin degradation products, and increased D-dimer levels. In some embodiments, treatment of sepsis with R5000 may result in a decrease in plasma fibrinogen levels and/or an increase in plasma levels of tPA, PAI-1, PAP, fibrinogen/fibrin degradation product, and/or D-dimer of from about 0.005% to about 0.05%, from about 0.01% to about 1%, from about 0.05% to about 2%, from about 0.1% to about 5%, from about 0.5% to about 10%, from about 1% to about 15%, from about 5% to about 25%, from about 10% to about 50%, from about 20% to about 60%, from about 25% to about 75%, from about 50% to about 100% when compared to levels in plasma samples from subjects not treated with R5000 (including subjects treated with other complement inhibitors) or when compared to levels in plasma samples taken from the same subject during a pre-treatment period or an earlier period of treatment. In some embodiments, sepsis-associated decrease in plasma fibrinogen levels and/or a sepsis-associated increase in plasma levels of tPA, PAI-1, PAP, fibrinogen/fibrin degradation product, and/or D-dimer may differ by at least 10,000% when compared to levels in plasma samples from subjects with sepsis that are treated with R5000.

Another consequence of overactive complement activity associated with sepsis is a reduction in red blood cells due to complement-dependent hemolysis and/or C3b-dependent opsonization. Methods of treating sepsis with R5000 according to the present disclosure may include reducing complement-dependent hemolysis. One method of evaluating complement-dependent hemolysis associated with sepsis involves obtaining a complete blood cell count. Complete blood cell counts may be obtained through automated processes that count the cell types present in blood samples. Results from complete blood cell count analysis typically include levels of hematocrit, red blood cell (RBC) counts, white blood cell (WBC) counts, and platelets. Hematocrit levels are used to determine the percentage of blood (by volume) that is made up of red blood cells. Hematocrit levels, platelet levels, RBC levels, and WBC levels may be reduced in sepsis due to hemolysis. In some embodiments, treatment of sepsis with R5000 increases hematocrit levels, platelet levels, RBC levels, and/or WBC levels. Increases may be immediate or may occur over time with treatment (e.g., single or multiple dose treatments).

In some embodiments, subject treatment with R5000 may decrease leukocyte (e.g., neutrophils and macrophages) activation associated with sepsis. "Activation," as used herein in the context of leukocytes refers to mobilization and/or maturation of these cells to carryout associated immune functions. Decreased leukocyte activation with R5000 treatment may be determined by assessing the subject treated or a sample obtained from the subject treated.

In some embodiments, treatment of sepsis with R5000 may improve one or more vital signs in subjects being treated. Such vital signs may include, but are not limited to, heart rate, mean systemic arterial pressure (MSAP), respiration rate, oxygen saturation, and body temperature.

In some embodiments, treatment of sepsis with R5000 may stabilize or reduce capillary leak and/or endothelial barrier dysfunction associated with sepsis (i.e., to maintain or improve capillary leak and/or endothelial barrier dysfunction). Stabilization or reduction of capillary leak and/or endothelial barrier dysfunction may be determined by measuring total plasma protein levels and/or plasma albumin levels. An increase in either level in comparison to plasma levels associated with sepsis may indicate reduced capillary leak. Accordingly, treatment of sepsis with R5000 may increase levels of total plasma protein and/or plasma albumin.

Methods of the present disclosure may include methods of treating sepsis with R5000, wherein levels of one or more acute phase proteins are reduced. Acute phase proteins are proteins produced by the liver under inflammatory condition. R5000 treatment may reduce inflammation associated with sepsis and lead to decreased production of acute phase proteins by the liver.

According to some methods of the invention, sepsis-induced organ damage and/or organ dysfunction may be reduced, reversed, or prevented by treatment with R5000. Indicators that may be reduced with improved organ function may include, but are not limited to plasma lactate (demonstrating improved vascular perfusion and clearance), creatinine, blood urea nitrogen (both indicating improved kidney function), and liver transaminases (indicating improved liver function). In some embodiments, febrile response, risk of secondary infection and/or risk of sepsis reoccurrence is reduced in subjects treated for sepsis with R5000.

Methods of the present disclosure may include preventing sepsis-related death and/or improving survival time of subjects afflicted with sepsis through treatment with R5000. Improved survival time may be determined through comparison of survival time in R5000-treated subjects to survival time in un-treated subjects (including subjects treated with one or more other forms of treatment). In some embodiments, survival times are increased by at least 1 day, at least 2 days, at least 3 days, at least 4 days, at least 5 days, at least 6 days, at least 7 days, at least 2 weeks, at least 1 month, at least 2 months, at least 4 months, at least 6 months, at least 1 year, at least 2 years, at least 5 years, or at least 10 years.

In some embodiments, administration of R5000 is carried out in a single dose. In some embodiments, administration of R5000 is carried out in multiple doses. For example, R5000 administration may include administration of an initial dose, followed by one or more repeat doses. Repeat doses may be administered from about 1 hour to about 24 hours, from about 2 hours to about 48 hours, from about 4 hours to about 72 hours, from about 8 hours to about 96 hours, from about 12 hours to about 36 hours, or from about 18 hours to about 60 hours after a previous dose. In some cases, repeat doses may be administered 1 day, 2 days, 3 days, 4 days, 5 days, 6 days, 7 days, 2 weeks, 4 weeks, 2 months, 4 months, 6 months, or more than 6 months after a previous dose. In some cases, repeat doses may be administered as needed to stabilize or reduce sepsis or to stabilize or reduce one or more effects associated with sepsis in a subject. Repeat doses may include the same amount of R5000 or may include a different amount.

Compounds and compositions of the invention may be used to control and/or balance complement activation for prevention and treatment of SIRS, sepsis and/or MOF. The methods of applying complement inhibitors to treat SIRS and sepsis may include those in U.S. publication No. US2013/0053302 or in U.S. Pat. No. 8,329,169, the contents of each of which are herein incorporated by reference in their entirety.

Acute Respiratory Distress Syndrome (ARDS)

In some embodiments, compounds and compositions, e.g., pharmaceutical compositions, of the invention may be used to treat and/or prevent development of acute respiratory distress syndrome (ARDS). ARDS is a widespread inflammation of the lungs and may be caused by trauma, infection (e.g., sepsis), severe pneumonia and/or inhalation of harmful substances. ARDS is typically a severe, life-threatening complication. Studies suggest that neutrophils may contribute to development of ARDS by affecting the accumulation of polymorphonuclear cells in the injured pulmonary alveoli and interstitial tissue of the lungs. Accordingly, compounds and compositions of the invention may be administered to reduce and/or prevent tissue factor production in alveolar neutrophils. Compounds and compositions of the invention may further be used for treatment, prevention and/or delaying of ARDS, in some cases according to any of the methods taught in International publication No. WO2009/014633, the contents of which are herein incorporated by reference in their entirety.

Periodontitis

In some embodiments, compounds and compositions, e.g., pharmaceutical compositions, of the invention may be used to treat or prevent development of periodontitis and/or associated conditions. Periodontitis is a widespread, chronic inflammation leading to the destruction of periodontal tissue which is the tissue supporting and surrounding the teeth. The condition also involves alveolar bone loss (bone that holds the teeth). Periodontitis may be caused by a lack of oral hygiene leading to accumulation of bacteria at the gum line, also known as dental plaque. Certain health conditions such as diabetes or malnutrition and/or habits such as smoking may increase the risk of periodontitis. Periodontitis may increase the risk of stroke, myocardial infarction, atherosclerosis, diabetes, osteoporosis, pre-term labor, as well as other health issues. Studies demonstrate a correlation between periodontitis and local complement activity. Periodontal bacteria may either inhibit or activate certain components of the complement cascade. Accordingly, compounds and compositions of the invention may be used to prevent and/or treat periodontitis and associated diseases and conditions. Complement activation inhibitors and treatment methods may include any of those taught by Hajishengallis in Biochem Pharmacol. 2010, 15; 80(12): 1 and Lambris or in US publication No. US2013/0344082, the contents of each of which are herein incorporated by reference in their entirety.

Dermatomyositis

In some embodiments, compounds, compositions, e.g., pharmaceutical compositions, and/or methods of the invention may be used to treat dermatomyositis. Dermatomyositis is an inflammatory myopathy characterized by muscle weakness and chronic muscle inflammation. Dermatomyositis often begins with a skin rash that is associated concurrently or precedes muscle weakness. Compounds, compositions, and/or methods of the invention may be used to reduce or prevent dermatomyositis.

Wounds and Injuries

Compounds and compositions, e.g., pharmaceutical compositions, of the invention may be used to treat and/or promote healing of different types of wounds and/or injuries. As used herein, the term "injury" typically refers to physical trauma, but may include localized infection or disease processes. Injuries may be characterized by harm, damage or destruction caused by external events affecting body parts and/or organs. Wounds are associated with cuts, blows, burns and/or other impacts to the skin, leaving the skin broken or damaged. Wounds and injuries are often acute but if not healed properly they may lead to chronic complications and/or inflammation.

Wounds and Burn Wounds

In some embodiments, compounds and compositions, e.g., pharmaceutical compositions, of the invention may be used to treat and/or to promote healing of wounds. Healthy skin provides a waterproof, protective barrier against pathogens and other environmental effectors. The skin also controls body temperature and fluid evaporation. When skin is wounded these functions are disrupted making skin healing challenging. Wounding initiates a set of physiological processes related to the immune system that repair and regenerate tissue. Complement activation is one of these processes. Complement activation studies have identified several complement components involved with wound healing as taught by van de Goot et al. in J Burn Care Res 2009, 30:274-280 and Cazander et al. Clin Dev Immunol, 2012, 2012:534291, the contents of each of which are herein incorporated by reference in their entirety. In some cases, complement activation may be excessive, causing cell death and enhanced inflammation (leading to impaired wound healing and chronic wounds). In some cases, compounds and compositions of the present invention may be used to reduce or eliminate such complement activation to promote wound healing. Treatment with compounds and compositions of the invention may be carried out according to any of the methods for treating wounds disclosed in International publication number WO2012/174055, the contents of which are herein incorporated by reference in their entirety.

Head Trauma

In some embodiments, compounds and compositions, e.g., pharmaceutical compositions, of the invention may be used to treat and/or promote healing of head trauma. Head traumas include injuries to the scalp, the skull or the brain. Examples of head trauma include, but are not limited to concussions, contusions, skull fracture, traumatic brain injuries and/or other injuries. Head traumas may be minor or severe. In some cases, head trauma may lead to long term physical and/or mental complications or death. Studies indicate that head traumas may induce improper intracranial complement cascade activation, which may lead to local inflammatory responses contributing to secondary brain damage by development of brain edema and/or neuronal death (Stahel et al. in Brain Research Reviews, 1998, 27: 243-56, the contents of which are herein incorporated by reference in their entirety). Compounds and compositions of the invention may be used to treat head trauma and/or to reduce or prevent related secondary complications. Methods of using compounds and compositions of the invention to control complement cascade activation in head trauma may include any of those taught by Holers et al. in U.S. Pat. No. 8,911,733, the contents of which are herein incorporated by reference in their entirety.

Crush Injury

In some embodiments, compounds and compositions, e.g., pharmaceutical compositions, of the invention may be used to treat and/or promote healing of crush injuries. Crush injuries are injuries caused by a force or a pressure put on the body causing bleeding, bruising, fractures, nerve injuries, wounds and/or other damages to the body. Compounds and compositions of the invention may be used to reduce complement activation following crush injuries, thereby promoting healing after crush injuries (e.g. by promoting nerve regeneration, promoting fracture healing, preventing or treating inflammation, and/or other related complications). Compounds and compositions of the invention may be used to promote healing according to any of the methods taught in U.S. Pat. No. 8,703,136; International Publication Nos. WO2012/162215; WO2012/174055; or US publication No. US2006/0270590, the contents of each of which are herein incorporated by reference in their entirety.

Ischemia/Reperfusion Injury

In some embodiments, compounds, compositions, e.g., pharmaceutical compositions, and/or methods of the present disclosure may be used to treat injuries associated with ischemia and/or reperfusion. Such injuries may be associated with surgical intervention (e.g., transplantation). Accordingly, compounds, compositions, and/or methods of the present disclosure may be used to reduce or prevent ischemia and/or reperfusion injuries.

Autoimmune Disease

The compounds and compositions, e.g., pharmaceutical compositions, of the invention may be used to treat subjects with autoimmune diseases and/or disorders. The immune system may be divided into innate and adaptive systems, referring to nonspecific immediate defense mechanisms and more complex antigen-specific systems, respectively. The complement system is part of the innate immune system, recognizing and eliminating pathogens. Additionally, complement proteins may modulate adaptive immunity, connecting innate and adaptive responses. Autoimmune diseases and disorders are immune abnormalities causing the system to target self tissues and substances. Autoimmune disease may involve certain tissues or organs of the body. Compounds and compositions of the invention may be used to modulate complement in the treatment and/or prevention of autoimmune diseases. In some cases, such compounds and compositions may be used according to the methods presented in Ballanti et al. Immunol Res (2013) 56:477-491, the contents of which are herein incorporated by reference in their entirety.

Anti-Phospholipid Syndrome (APS) and Catastrophic Anti-Phospholipid Syndrome (CAPS)

In some embodiments, compounds and compositions, e.g., pharmaceutical compositions, of the invention may be used to prevent and/or treat anti-phospholipid syndrome (APS) by complement activation control. APS is an autoimmune condition caused by anti-phospholipid antibodies that cause the blood to clot. APS may lead to recurrent venous or arterial thrombosis in organs, and complications in placental circulations causing pregnancy-related complications such as miscarriage, still birth, preeclampsia, premature birth and/or other complications. Catastrophic anti-phospholipid syndrome (CAPS) is an extreme and acute version of a similar condition leading to occlusion of veins in several organs simultaneously. Studies suggest that complement activation may contribute to APS-related complications including pregnancy-related complications, thrombotic (clotting) complications, and vascular complications. Compound and compositions of the invention may be used to treat APS-related conditions by reducing or eliminating complement activation. In some cases, compounds and compositions of the invention may be used to treat APS and/or APS-related complications according to the methods taught by Salmon et al. Ann Rheum Dis 2002; 61 (Suppl II):ii46-ii50 and Mackworth-Young in Clin Exp Immunol 2004, 136:393-401, the contents of which are herein incorporated by reference in their entirety.

Cold Agglutinin Disease

In some embodiments, compounds and compositions, e.g., pharmaceutical compositions, of the invention may be used to treat cold agglutinin disease (CAD), also referred to as cold agglutinin-mediated hemolysis. CAD is an autoimmune disease resulting from a high concentration of IgM antibodies interacting with red blood cells at low range body temperatures [Engelhardt et al. Blood, 2002, 100(5):1922-23]. CAD may lead to conditions such as anemia, fatigue, dyspnea, hemoglobinuria and/or acrocyanosis. CAD is related to robust complement activation and studies have shown that CAD may be treated with complement inhibitor therapies. Accordingly, the present invention provides methods of treating CAD using compounds and compositions of the invention. In some cases, compounds and compositions of the invention may be used to treat CAD according to the methods taught by Roth et al in Blood, 2009, 113:3885-86 or in International publication No. WO2012/139081, the contents of each of which are herein incorporated by reference in their entirety.

Myasthenia Gravis

In some embodiments, compounds, compositions, e.g., pharmaceutical compositions, and/or methods of the invention may be used to treat myasthenia gravis. Myasthenia gravis is a neuromuscular disease caused by autoimmunity. Compounds, compositions, and/or methods of the invention may be used to reduce or prevent neuromuscular issues associated with Myasthenia gravis.

Guillain-Barre Syndrome

In some embodiments, compounds, compositions, e.g., pharmaceutical compositions, and methods of the invention may be used to treat Guillain-Barre syndrome (GBS). GBS is an autoimmune disease involving autoimmune attack of the peripheral nervous system. Compounds, compositions, and/or methods of the invention may be used to reduce or prevent peripheral nervous issues associated with GBS.

Vascular Indications

In some embodiments, compounds and compositions, e.g., pharmaceutical compositions, of the invention may be used to treat vascular indications affecting blood vessels (e.g., arteries, veins, and capillaries). Such indications may affect blood circulation, blood pressure, blood flow, organ function and/or other bodily functions.

Thrombotic Microangiopathy (TMA)

In some embodiments, compounds and compositions, e.g., pharmaceutical compositions, of the invention may be used to treat and/or prevent thrombotic microangiopathy (TMA) and associated diseases. Microangiopathies affect small blood vessels (capillaries) of the body causing capillary walls to become thick, weak, and prone to bleeding and slow blood circulation. TMAs tend to lead to the development of vascular thrombi, endothelial cell damage, thrombocytopenia, and hemolysis. Organs such as the brain, kidney, muscles, gastrointestinal system, skin, and lungs may be affected. TMAs may arise from medical operations and/or conditions that include, but are not limited to, hematopoietic stem cell transplantation (HSCT), renal disorders, diabetes and/or other conditions. TMAs may be caused by underlying complement system dysfunction, as described by Meri et al. in European Journal of Internal Medicine, 2013, 24: 496-502, the contents of which are herein incorporated by reference in their entirety. Generally, TMAs may result from increased levels of certain complement components leading to thrombosis. In some cases, this may be caused by mutations in complement proteins or related enzymes. Resulting complement dysfunction may lead to complement targeting of endothelial cells and platelets leading to increased thrombosis. In some embodiments, TMAs may be prevented and/or treated with compounds and compositions of the invention. In some cases, methods of treating TMAs with compounds and compositions of the invention may be carried out according to those described in US publication Nos. US2012/0225056 or US2013/0246083, the contents of each of which are herein incorporated by reference in their entirety.

Disseminated Intravascular Coagulation (DIC)

In some embodiments, compounds and compositions, e.g., pharmaceutical compositions, of the invention may be used to prevent and/or treat disseminated intravascular coagulation (DIC) by controlling complement activation. DIC is a pathological condition where the clotting cascade in blood is widely activated and results in formation of blood clots especially in the capillaries. DIC may lead to an obstructed blood flow of tissues and may eventually damage organs. Additionally, DIC affects the normal process of blood clotting that may lead to severe bleeding. Compounds and compositions of the invention may be used to treat, prevent or reduce the severity of DIC by modulating complement activity. In some cases compounds and compositions of the invention may be used according to any of the methods of DIC treatment taught in U.S. Pat. No. 8,652,477, the contents of which are herein incorporated by reference in their entirety.

Vasculitis

In some embodiments, compounds and compositions, e.g., pharmaceutical compositions, of the invention may be used to prevent and/or treat vasculitis. Generally, vasculitis is a disorder related to inflammation of blood vessels, including veins and arteries, characterized by white blood cells attacking tissues and causing swelling of the blood vessels. Vasculitis may be associated with an infection, such as in Rocky Mountain spotted fever, or autoimmunity. An example of autoimmunity associated vasculitis is Anti-Neutrophil Cytoplasmic Autoantibody (ANCA) vasculitis. ANCA vasculitis is caused by abnormal antibodies attacking the body's own cells and tissues. ANCAs attack the cytoplasm of certain white blood cells and neutrophils, causing them to attack the walls of the vessels in certain organs and tissues of the body. ANCA vasculitis may affect skin, lungs, eyes and/or kidney. Studies suggest that ANCA disease activates an alternative complement pathway and generates certain complement components that create an inflammation amplification loop resulting in a vascular injury (Jennette et al. 2013, Semin Nephrol. 33(6): 557-64, the contents of which are herein incorporated by reference in their entirety). In some cases, compounds and compositions of the invention may be used to prevent and/or treat ANCA vasculitis by inhibiting complement activation.

Atypical Hemolytic Uremic Syndrome

In some embodiments, compounds, compositions, e.g., pharmaceutical compositions, and/or methods of the present disclosure may be useful for treatment of atypical hemolytic uremic syndrome (aHUS). aHUS is a rare disease caused by unchecked complement activation characterized by blood clot formation in small blood vessels. Compositions and methods of the invention may be useful for reducing or preventing complement activation associated with aHUS.

Neurological Indications

The compounds and compositions, e.g., pharmaceutical compositions, of the invention may be used to prevent, treat and/or ease the symptoms of neurological indications, including, but not limited to neurodegenerative diseases and related disorders. Neurodegeneration generally relates to a loss of structure or function of neurons, including death of neurons. These disorders may be treated by inhibiting the effect of complement on neuronal cells using compounds and compositions of the invention. Neurodegenerative related disorders include, but are not limited to, Amyelotrophic Lateral Sclerosis (ALS), Multiple Sclerosis (MS), Parkinson's disease and Alzheimer's disease.

Amyotrophic Lateral Sclerosis (ALS)

In some embodiments, compounds and compositions, e.g., pharmaceutical compositions, of the invention may be used to prevent, treat and/or ease the symptoms of ALS. ALS is a fatal motor neuron disease characterized by the degeneration of spinal cord neurons, brainstems and motor cortex. ALS causes loss of muscle strength leading eventually to a respiratory failure. Complement dysfunction may contribute to ALS, and therefore ALS may be prevented, treated and/or the symptoms may be reduced by therapy with compounds and compositions of the invention targeting complement activity. In some cases, compounds and compositions of the invention may be used to promote nerve regeneration. In some cases, compounds and compositions of the invention may be used as complement inhibitors according to any of the methods taught in US publication No. US2014/0234275 or US2010/0143344, the contents of each of which are herein incorporated by reference in their entirety.

Alzheimer's Disease

In some embodiments, compounds and compositions, e.g., pharmaceutical compositions, of the invention may be used to prevent and/or treat Alzheimer's disease by controlling complement activity. Alzheimer's disease is a chronic neurodegenerative disease with symptoms that may include disorientation, memory loss, mood swings, behavioral problems and eventually loss of bodily functions. Alzheimer's disease is thought to be caused by extracellular brain deposits of amyloid that are associated with inflammation-related proteins such as complement proteins (Sjoberg et al. 2009. Trends in Immunology. 30(2): 83-90, the contents of which are herein incorporated by reference in their entirety). In some cases, compounds and compositions of the invention may be used as complement inhibitors according to any of the Alzheimer's treatment methods taught in US publication No. US2014/0234275, the contents of which are herein incorporated by reference in their entirety.

Kidney-Related Indications

The compounds and compositions, e.g., pharmaceutical compositions, of the invention may be used to treat certain diseases, disorders and/or conditions related to kidneys, in some cases by inhibiting complement activity. Kidneys are organs responsible for removing metabolic waste products from the blood stream. Kidneys regulate blood pressure, the urinary system, and homeostatic functions and are therefore essential for a variety of bodily functions. Kidneys may be more seriously affected by inflammation (as compared to other organs) due to unique structural features and exposure to blood. Kidneys also produce their own complement proteins which may be activated upon infection, kidney disease, and renal transplantations. In some cases, compounds and compositions of the invention may be used as complement inhibitors in the treatment of certain diseases, conditions, and/or disorders of the kidney according to the methods taught by Quigg, J Immunol 2003; 171:3319-24, the contents of which are herein incorporated by reference in their entirety.

Lupus Nephritis

In some embodiments, compounds and compositions, e.g., pharmaceutical compositions, of the invention may be used to prevent and/or treat lupus nephritis by inhibiting complement activity. Lupus nephritis is a kidney inflammation caused by an autoimmune disease called systemic lupus erythematosus (SLE). Symptoms of lupus nephritis include high blood pressure; foamy urine; swelling of the legs, the feet, the hands, or the face; joint pain; muscle pain; fever; and rash. Lupus nephritis may be treated by inhibitors that control complement activity, including compounds and compositions of the present invention. Methods and compositions for preventing and/or treating Lupus nephritis by complement inhibition may include any of those taught in US publication No. US2013/0345257 or U.S. Pat. No. 8,377,437, the contents of each of which are herein incorporated by reference in their entirety.

Membranous Glomerulonephritis (MGN)

In some embodiments, compounds and composition, e.g., pharmaceutical compositions, of the invention may be used to prevent and/or treat membranous glomerulonephritis (MGN) disorder by inhibiting the activation of certain complement components. MGN is a disorder of the kidney that may lead to inflammation and structural changes. MGN is caused by antibodies binding to a soluble antigen in kidney capillaries (glomerulus). MGN may affect kidney functions, such as filtering fluids and may lead to kidney failure. Compounds and compositions of the invention may be used according to methods of preventing and/or treating MGN by complement inhibition taught in U.S. publication No. US2010/0015139 or in International publication No. WO2000/021559, the contents of each of which are herein incorporated by reference in their entirety.

Hemodialysis Complications

In some embodiments, compounds and compositions, e.g., pharmaceutical compositions, of the invention may be used to prevent and/or treat complications associated with hemodialysis by inhibiting complement activation. Hemodialysis is a medical procedure used to maintain kidney function in subjects with kidney failure. In hemodialysis, the removal of waste products such as creatinine, urea, and free water from blood is performed externally. A common complication of hemodialysis treatment is chronic inflammation caused by contact between blood and the dialysis membrane. Another common complication is thrombosis referring to a formation of blood clots that obstructs the blood circulation. Studies have suggested that these complications are related to complement activation. Hemodialysis may be combined with complement inhibitor therapy to provide means of controlling inflammatory responses and pathologies and/or preventing or treating thrombosis in subjects going through hemodialysis due to kidney failure. Methods of using compounds and compositions of the invention for treatment of hemodialysis complications may be carried out according to any of the methods taught by DeAngelis et al in Immunobiology, 2012, 217(11): 1097-1105 or by Kourtzelis et al. Blood, 2010, 116(4):631-639, the contents of each of which are herein incorporated by reference in their entirety.

Ocular Diseases

In some embodiments, compounds and compositions, e.g., pharmaceutical compositions, of the invention may be used to prevent and/or treat certain ocular related diseases, disorders and/or conditions. In a healthy eye the complement system is activated at a low level and is continuously regulated by membrane-bound and soluble intraocular proteins that protect against pathogens. Therefore the activation of complement plays an important role in several complications related to the eye and controlling complement activation may be used to treat such diseases. Compounds and compositions of the invention may be used as complement inhibitors in the treatment of ocular disease according to any of the methods taught by Jha et al. in Mol Immunol. 2007; 44(16): 3901-3908 or in U.S. Pat. No. 8,753,625, the contents of each of which are herein incorporated by reference in their entirety.

Age-Related Macular Degeneration (AMD)

In some embodiments, compounds and compositions, e.g., pharmaceutical compositions, of the invention may be used to prevent and/or treat age-related macular degeneration (AMD) by inhibiting ocular complement activation. AMD is a chronic ocular disease causing blurred central vision, blind spots in central vision, and/or eventual loss of central vision. Central vision affects ability to read, drive a vehicle and/or recognize faces. AMD is generally divided into two types, non-exudative (dry) and exudative (wet). Dry AMD refers to the deterioration of the macula which is the tissue in the center of the retina. Wet AMD refers to the failure of blood vessels under the retina leading to leaking of blood and fluid. Several human and animal studies have identified complement proteins that are related to AMD and novel therapeutic strategies included controlling complement activation pathways, as discussed by Jha et al. in Mol Immunol. 2007; 44(16): 3901-8. Methods of the invention involving the use of compounds and compositions of the invention for prevention and/or treatment of AMD may include any of those taught in US publication Nos. US2011/0269807 or US2008/0269318, the contents of each of which are herein incorporated by reference in their entirety.

Corneal Disease

In some embodiments, compounds and compositions, e.g., pharmaceutical compositions, of the invention may be used to prevent and/or treat corneal diseases by inhibiting ocular complement activation. The complement system plays an important role in protection of the cornea from pathogenic particles and/or inflammatory antigens. The cornea is the outermost front part of the eye covering and protecting the iris, pupil and anterior chamber and is therefore exposed to external factors. Corneal diseases include, but are not limited to, keratoconus, keratitis, ocular herpes and/or other diseases. Corneal complications may cause pain, blurred vision, tearing, redness, light sensitivity and/or corneal scarring. The complement system is critical for corneal protection, but complement activation may cause damage to the corneal tissue after an infection is cleared as certain complement compounds are heavily expressed. Methods of the present invention for modulating complement activity in the treatment of corneal disease may include any of those taught by Jha et al. in Mol Immunol. 2007; 44(16): 3901-8, the contents of which are herein incorporated by reference in their entirety.

Autoimmune Uveitis

In some embodiments, compounds and compositions, e.g., pharmaceutical compositions, of the invention may be used to prevent and/or treat uveitis, which is an inflammation of the uveal layer of the eye. Uvea is the pigmented area of the eye comprising the choroids, iris and ciliary body of the eye. Uveitis causes redness, blurred vision, pain, synechia and may eventually cause blindness. Studies have indicated that complement activation products are present in the eyes of patients with autoimmune uveitis and complement plays an important role in disease development. In some cases, compounds and compositions of the invention may be used to treat and/or prevent uveitis according to any of the methods identified in Jha et al. in Mol Immunol. 2007. 44(16): 3901-8, the contents of which are herein incorporated by reference in their entirety.

Diabetic Retinopathy

In some embodiments, compounds and compositions, e.g., pharmaceutical compositions, of the invention may be used to prevent and/or treat diabetic retinopathy which is a disease caused by changes in retinal blood vessels in diabetic patients. Retinopathy may cause blood vessel swelling and fluid leaking and/or growth of abnormal blood vessels. Diabetic retinopathy affects vision and may eventually lead to blindness. Studies have suggested that activation of complement has an important role in the development of diabetic retinopathy. In some cases, compounds and compositions of the invention may be used according to methods of diabetic retinopathy treatment described in Jha et al. Mol Immunol. 2007; 44(16): 3901-8, the contents of which are herein incorporated by reference in their entirety.

Neuromyelitis Optica (NMO)

In some embodiments, compounds, compositions, e.g., pharmaceutical compositions, and/or methods of the invention may be used to treat neuromyelitis optica (NMO). NMO is an autoimmune disease that leads to destruction of the optic nerve. Compounds and/or methods of the invention may be used to prevent nerve destruction in subjects with NMO.

Sjogren's Syndrome

In some embodiments, compounds, compositions, e.g., pharmaceutical compositions, and/or methods of the invention may be used to treat Sjorgren's syndrome. Sjorgren's syndrome is an ocular disease characterized by dry eyes that may burn and/or itch. It is an autoimmune disorder where the immune system targets glands in the eyes and mouth responsible for moisturizing those regions. Compounds, compositions, and/or methods of the present disclosure may be used to treat and/or reduce the symptoms of Sjorgren's syndrome.

Pre-Eclampsia and HELLP-Syndrome

In some embodiments, compounds and compositions, e.g., pharmaceutical compositions, of the invention may be used to prevent and/or treat pre-eclampsia and/or HELLP (abbreviation standing for syndrome features of 1) hemolysis, 2) elevated liver enzymes and 3) low platelet count) syndrome by complement inhibitor therapy. Pre-eclampsia is a disorder of pregnancy with symptoms including elevated blood pressure, swelling, shortness of breath, kidney dysfunction, impaired liver function and/or low blood platelet count. Pre-eclampsia is typically diagnosed by a high urine protein level and high blood pressure. HELLP syndrome is a combination of hemolysis, elevated liver enzymes and low platelet conditions. Hemolysis is a disease involving rupturing of red blood cells leading to the release of hemoglobin from red blood cells. Elevated liver enzymes may indicate a pregnancy-induced liver condition. Low platelet levels lead to reduced clotting capability, causing danger of excessive bleeding. HELLP is associated with a pre-eclampsia and liver disorder. HELLP syndrome typically occurs during the later stages of pregnancy or after childbirth. It is typically diagnosed by blood tests indicating the presence of the three conditions it involves. Typically HELLP is treated by inducing delivery.

Studies suggest that complement activation occurs during HELLP syndrome and pre-eclampsia and that certain complement components are present at increased levels during HELLP and pre-eclampsia. Complement inhibitors may be used as therapeutic agents to prevent and/or treat these conditions. Compounds and compositions of the invention may be used according to methods of preventing and/or treating HELLP and pre-eclampsia taught by Heager et al. in Obstetrics & Gynecology, 1992, 79(1):19-26 or in International publication No. WO201/078622, the contents of each of which are herein incorporated by reference in their entirety.

Formulations

In some embodiments, compounds or compositions, e.g., pharmaceutical compositions, of the invention are formulated in aqueous solutions. In some cases, aqueous solutions further include one or more salt and/or one or more buffering agent. Salts may include sodium chloride which may be included at concentrations of from about 0.05 mM to about 50 mM, from about 1 mM to about 100 mM, from about 20 mM to about 200 mM, or from about 50 mM to about 500 mM. Further solutions may comprise at least 500 mM sodium chloride. In some cases, aqueous solutions include sodium phosphate. Sodium phosphate may be included in aqueous solutions at a concentration of from about 0.005 mM to about 5 mM, from about 0.01 mM to about 10 mM, from about 0.1 mM to about 50 mM, from about 1 mM to about 100 mM, from about 5 mM to about 150 mM, or from about 10 mM to about 250 mM. In some cases, at least 250 mM sodium phosphate concentrations are used.

Compositions of the invention may include C5 inhibitors at a concentration of from about 0.001 mg/mL to about 0.2 mg/mL, from about 0.01 mg/mL to about 2 mg/mL, from about 0.1 mg/mL to about 10 mg/mL, from about 0.5 mg/mL to about 5 mg/mL, from about 1 mg/mL to about 20 mg/mL, from about 15 mg/mL to about 40 mg/mL, from about 25 mg/mL to about 75 mg/mL, from about 50 mg/mL to about 200 mg/mL, or from about 100 mg/mL to about 400 mg/mL. In some cases, compositions of the invention include C5 inhibitors at a concentration of at least 400 mg/mL.

Compositions of the invention may comprise C5 inhibitors at a concentration of approximately, about or exactly any of the following values: 0.001 mg/mL, 0.2 mg/mL, 0.01 mg/mL, 2 mg/mL, 0.1 mg/mL, 10 mg/mL, 0.5 mg/mL, 5 mg/mL, 1 mg/mL, 20 mg/mL, 15 mg/mL, 40 mg/mL, 25 mg/mL, 75 mg/mL, 50 mg/mL, 200 mg/mL, 100 mg/mL, or 400 mg/mL. In some cases, compositions of the invention include C5 inhibitors at a concentration of at least 40 mg/mL.

In some embodiments, compositions of the invention include aqueous compositions including at least water and a C5 inhibitor (e.g., a cyclic C5 inhibitor polypeptide). Aqueous C5 inhibitor compositions of the invention may further include one or more salt and/or one or more buffering agent. In some cases, aqueous compositions of the invention include water, a cyclic C5 inhibitor polypeptide, a salt, and a buffering agent.

Aqueous C5 inhibitor formulations of the invention may have pH levels of from about 2.0 to about 3.0, from about 2.5 to about 3.5, from about 3.0 to about 4.0, from about 3.5 to about 4.5, from about 4.0 to about 5.0, from about 4.5 to about 5.5, from about 5.0 to about 6.0, from about 5.5 to about 6.5, from about 6.0 to about 7.0, from about 6.5 to about 7.5, from about 7.0 to about 8.0, from about 7.5 to about 8.5, from about 8.0 to about 9.0, from about 8.5 to about 9.5, or from about 9.0 to about 10.0.

In some cases, compounds and compositions of the invention are prepared according to good manufacturing practice (GMP) and/or current GMP (cGMP). Guidelines used for implementing GMP and/or cGMP may be obtained from one or more of the US Food and Drug Administration (FDA), the World Health Organization (WHO), and the International Conference on Harmonization (ICH).

Dosage and Administration

For treatment of human subjects, C5 inhibitors may be formulated as pharmaceutical compositions. Depending on the subject to be treated, the mode of administration, and the type of treatment desired (e.g., prevention, prophylaxis, or therapy) C5 inhibitors may be formulated in ways consonant with these parameters. A summary of such techniques is found in Remington: The Science and Practice of Pharmacy, 21st Edition, Lippincott Williams & Wilkins, (2005); and Encyclopedia of Pharmaceutical Technology, eds. J. Swarbrick and J. C. Boylan, 1988-1999, Marcel Dekker, New York, each of which is incorporated herein by reference.

C5 inhibitors of the present invention may be provided in a therapeutically effective amount. In some cases, a therapeutically effective amount a C5 inhibitor of the invention may be achieved by administration of a dose of from about 0.1 mg to about 1 mg, from about 0.5 mg to about 5 mg, from about 1 mg to about 20 mg, from about 5 mg to about 50 mg, from about 10 mg to about 100 mg, from about 20 mg to about 200 mg, or at least 200 mg of one or more C5 inhibitors.

In some embodiments, subjects may be administered a therapeutic amount of a C5 inhibitor based on the weight of such subjects. In some cases, C5 inhibitors are administered at a dose of from about 0.001 mg/kg to about 1.0 mg/kg, from about 0.01 mg/kg to about 2.0 mg/kg, from about 0.05 mg/kg to about 5.0 mg/kg, from about 0.03 mg/kg to about 3.0 mg/kg, from about 0.01 mg/kg to about 10 mg/kg, from about 0.1 mg/kg to about 2.0 mg/kg, from about 0.2 mg/kg to about 3.0 mg/kg, from about 0.4 mg/kg to about 4.0 mg/kg, from about 1.0 mg/kg to about 5.0 mg/kg, from about 2.0 mg/kg to about 4.0 mg/kg, from about 1.5 mg/kg to about 7.5 mg/kg, from about 5.0 mg/kg to about 15 mg/kg, from about 7.5 mg/kg to about 12.5 mg/kg, from about 10 mg/kg to about 20 mg/kg, from about 15 mg/kg to about 30 mg/kg, from about 20 mg/kg to about 40 mg/kg, from about 30 mg/kg to about 60 mg/kg, from about 40 mg/kg to about 80 mg/kg, from about 50 mg/kg to about 100 mg/kg, or at least 100 mg/kg. Such ranges may include ranges suitable for administration to human subjects. Dosage levels may be highly dependent on the nature of the condition; drug efficacy; the condition of the patient; the judgment of the practitioner; and the frequency and mode of administration.

In some cases, C5 inhibitors of the invention are provided at concentrations adjusted to achieve a desired level the C5 inhibitor in a sample, biological system, or subject (e.g., plasma level in a subject). In some cases, desired concentrations of C5 inhibitors in a sample, biological system, or subject may include concentrations of from about 0.001 µM to about 0.01 µM, from about 0.005 µM to about 0.05 µM, from about 0.02 µM to about 0.2 µM, from about 0.03 µM to about 0.3 µM, from about 0.05 µM to about 0.5 µM, from about 0.01 µM to about 2.0 µM, from about 0.1 µM to about 50 µM, from about 0.1 µM to about 10 µM, from about 0.1 µM to about 5 µM, or from about 0.2 µM to about 20 µM. In some cases, desired concentrations of C5 inhibitors in subject plasma may be from about 0.1 µg/mL to about 1000 µg/mL. In other cases, desired concentrations of C5 inhibitors in subject plasma may be from about 0.01 µg/mL to about 2 µg/mL, from about 0.02 µg/mL to about 4 µg/mL, from about 0.05 µg/mL to about 5 µg/mL, from about 0.1 µg/mL to about 1.0 µg/mL, from about 0.2 µg/mL to about 2.0 µg/mL, from about 0.5 µg/mL to about 5 µg/mL, from about 1 µg/mL to about 5 µg/mL, from about 2 µg/mL to about 10 µg/mL, from about 3 µg/mL to about 9 µg/mL, from about 5 µg/mL to about 20 µg/mL, from about 10 µg/mL to about 40 µg/mL, from about 30 µg/mL to about 60 µg/mL, from about 40 µg/mL to about 80 µg/mL, from about 50 µg/mL to about 100 µg/mL, from about 75 µg/mL to about 150 µg/mL, or at least 150 µg/mL. In other embodiments, C5 inhibitors are administered at a dose sufficient to achieve a maximum serum concentration ($C_{max}$) of at least 0.1 µg/mL, at least 0.5 µg/mL, at least 1 µg/mL, at least 5 µg/mL, at least 10 µg/mL, at least 50 µg/mL, at least 100 µg/mL, or at least 1000 µg/mL.

In some embodiments, doses sufficient to sustain C5 inhibitor levels of from about 0.1 µg/mL to about 20 µg/mL are provided to reduce hemolysis in a subject by from about 25% to about 99%.

In some embodiments, C5 inhibitors are administered daily at a dose sufficient to deliver from about 0.1 mg/day to about 60 mg/day per kg weight of a subject. In some cases, the $C_{max}$ achieved with each dose is from about 0.1 µg/mL to about 1000 µg/mL. In such cases, the area under the curve (AUC) between doses may be from about 200 µg*hr/mL to about 10,000 µg*hr/mL.

According to some methods of the invention, C5 inhibitors of the invention are provided at concentrations needed to achieve a desired effect. In some cases, compounds and compositions of the invention are provided at an amount necessary to reduce a given reaction or process by half. The concentration needed to achieve such a reduction is referred to herein as the half maximal inhibitory concentration, or "$IC_{50}$." Alternatively, compounds and compositions of the invention may be provided at an amount necessary to increase a given reaction, activity or process by half. The concentration needed for such an increase is referred to herein as the half maximal effective concentration or "$EC_{50}$."

The C5 inhibitors of the invention may be present in amounts totaling 0.1-95% by weight of the total weight of the composition. In some cases C5 inhibitors are provided by intravenous (IV) administration. In some cases, C5 inhibitors are provided by subcutaneous (SC) administration.

SC administration of C5 inhibitors of the invention may, in some cases, provide advantages over IV administration. SC administration may allow patients to provide self-treatment. Such treatment may be advantageous in that patients could provide treatment to themselves in their own home, avoiding the need to travel to a provider or medical facility. Further, SC treatment may allow patients to avoid long-term complications associated with IV administration, such as infections, loss of venous access, local thrombosis, and hematomas. In some embodiments, SC treatment may increase patient compliance, patient satisfaction, quality of life, reduce treatment costs and/or drug requirements.

In some cases, daily SC administration provides steady-state C5 inhibitor concentrations that are reached within 1-3 doses, 2-3 doses, 3-5 doses, or 5-10 doses. In some cases, daily SC doses of 0.1 mg/kg may achieve sustained C5 inhibitor levels greater than or equal to 2.5 µg/mL and/or inhibition of complement activity of greater than 90%.

C5 inhibitors of the invention may exhibit slow absorption kinetics (time to maximum observed concentration of greater than 4-8 hours) and high bioavailability (from about 75% to about 100%) after SC administration.

In some embodiments, dosage and/or administration are altered to modulate the half-life ($t_{1/2}$) of C5 inhibitor levels in a subject or in subject fluids (e.g., plasma). In some cases, $t_{1/2}$ is at least 1 hour, at least 2 hrs, at least 4 hrs, at least 6 hrs, at least 8 hrs, at least 10 hrs, at least 12 hrs, at least 16 hrs, at least 20 hrs, at least 24 hrs, at least 36 hrs, at least 48 hrs, at least 60 hrs, at least 72 hrs, at least 96 hrs, at least 5 days, at least 6 days, at least 7 days, at least 8 days, at least 9 days, at least 10 days, at least 11 days, at least 12 days, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, or at least 16 weeks.

In some embodiments, C5 inhibitors of the invention may exhibit long terminal $t_{1/2}$. Extended terminal $t_{1/2}$ may be due to extensive target binding and/or additional plasma protein binding. In some cases, C5 inhibitors of the invention exhibit $t_{1/2}$ values greater than 24 hours in both plasma and whole blood. In some cases, C5 inhibitors do not lose functional activity after incubation in human whole blood at 37° C. for 16 hours.

In some embodiments, dosage and/or administration are altered to modulate the steady state volume of distribution of C5 inhibitors. In some cases, the steady state volume of distribution of C5 inhibitors is from about 0.1 mL/kg to about 1 mL/kg, from about 0.5 mL/kg to about 5 mL/kg, from about 1 mL/kg to about 10 mL/kg, from about 5 mL/kg to about 20 mL/kg, from about 15 mL/kg to about 30 mL/kg, from about 10 mL/kg to about 200 mL/kg, from about 20 mL/kg to about 60 mL/kg, from about 30 mL/kg to about 70 mL/kg, from about 50 mL/kg to about 200 mL/kg, from about 100 mL/kg to about 500 mL/kg, or at least 500 mL/kg. In some cases, the dosage and/or administration of C5 inhibitors is adjusted to ensure that the steady state volume of distribution is equal to at least 50% of total blood volume. In some embodiments, C5 inhibitor distribution may be restricted to the plasma compartment.

In some embodiments, C5 inhibitors of the invention exhibit a total clearance rate of from about 0.001 mL/hr/kg to about 0.01 mL/hr/kg, from about 0.005 mL/hr/kg to about 0.05 mL/hr/kg, from about 0.01 mL/hr/kg to about 0.1 mL/hr/kg, from about 0.05 mL/hr/kg to about 0.5 mL/hr/kg, from about 0.1 mL/hr/kg to about 1 mL/hr/kg, from about 0.5 mL/hr/kg to about 5 mL/hr/kg, from about 0.04 mL/hr/kg to about 4 mL/hr/kg, from about 1 mL/hr/kg to about 10 mL/hr/kg, from about 5 mL/hr/kg to about 20 mL/hr/kg, from about 15 mL/hr/kg to about 30 mL/hr/kg, or at least 30 mL/hr/kg.

Time periods for which maximum concentration of C5 inhibitors in subjects (e.g., in subject serum) are maintained ($T_{max}$ values) may be adjusted by altering dosage and/or administration (e.g., subcutaneous administration). In some cases, C5 inhibitors have $T_{max}$ values of from about 1 min to about 10 min, from about 5 min to about 20 min, from about 15 min to about 45 min, from about 30 min to about 60 min, from about 45 min to about 90 min, from about 1 hour to about 48 hrs, from about 2 hrs to about 10 hrs, from about 5 hrs to about 20 hrs, from about 10 hrs to about 60 hrs, from about 1 day to about 4 days, from about 2 days to about 10 days, or at least 10 days.

In some embodiments, C5 inhibitors of the invention may be administered without off-target effects. In some cases, C5 inhibitors of the invention do not inhibit hERG (human ether-a-go-go related gene), even with concentrations less than or equal to 300 μM. SC injection of C5 inhibitors of the invention with dose levels up to 10 mg/kg may be well tolerated and not result in any adverse effects of the cardiovascular system (e.g., elevated risk of prolonged ventricular repolarization) and/or respiratory system.

C5 inhibitor doses may be determined using the no observed adverse effect level (NOAEL) observed in another species. Such species may include, but are not limited to monkeys, rats, rabbits, and mice. In some cases, human equivalent doses (HEDs) may be determined by allometric scaling from NOAELs observed in other species. In some cases, HEDs result in therapeutic margins of from about 2 fold to about 5 fold, from about 4 fold to about 12 fold, from about 5 fold to about 15 fold, from about 10 fold to about 30 fold, or at least 30 fold. In some cases, therapeutic margins are determined by using exposure in primates and estimated human $C_{max}$ levels in humans.

In some embodiments, C5 inhibitors of the invention allow for a rapid washout period in cases of infection where prolonged inhibition of the complement system prove detrimental.

C5 inhibitor administration according to the invention may be modified to reduce potential clinical risks to subjects. Infection with *Neisseria meningitidis* is a known risk of C5 inhibitors, including eculizumab. In some cases, risk of infection with *Neisseria meningitides* is minimized by instituting one or more prophylactic steps. Such steps may include the exclusion of subjects who may already be colonized by these bacteria. In some cases, prophylactic steps may include coadministration with one or more antibiotics. In some cases, ciprofloxacin may be coadministered.

In some cases, ciprofloxacin may be coadministered orally at a dose of from about 100 mg to about 1000 mg (e.g., 500 mg).

In some embodiments, C5 inhibitor administration may be carried out using an auto-injector device. Such devices may allow for self-administration (e.g., daily administration).

Dosage Frequency

In some embodiments, C5 inhibitors of the invention are administered at a frequency of every hour, every 2 hrs, every 4 hrs, every 6 hrs, every 12 hrs, every 18 hrs, every 24 hrs, every 36 hrs, every 72 hrs, every 84 hrs, every 96 hrs, every 5 days, every 7 days, every 10 days, every 14 days, every week, every two weeks, every 3 weeks, every 4 weeks, every month, every 2 months, every 3 months, every 4 months, every 5 months, every 6 months, every year, or at least every year. In some cases, C5 inhibitors are administered once daily or administered as two, three, or more sub-doses at appropriate intervals throughout the day.

In some embodiments, C5 inhibitors are administered in multiple daily doses. In some cases, C5 inhibitors are administered daily for 7 days. In some cases, C5 inhibitors are administered daily for 7 to 100 days. In some cases, C5 inhibitors are administered daily for at least 100 days. In some cases, C5 inhibitors are administered daily for an indefinite period.

C5 inhibitors delivered intravenously may be delivered by infusion over a period of time, such as over a 5 minute, 10 minute, 15 minute, 20 minute, or 25 minute period. The administration may be repeated, for example, on a regular basis, such as hourly, daily, weekly, biweekly (i.e., every two weeks), for one month, two months, three months, four months, or more than four months. After an initial treatment regimen, treatments may be administered on a less frequent basis. For example, after biweekly administration for three months, administration may be repeated once per month, for six months or a year or longer. Administration C5 inhibitor may reduce, lower, increase or alter binding or any physiologically deleterious process (e.g., in a cell, tissue, blood, urine or other compartment of a patient) by at least 10%, at least 15%, at least 20%, at least 25%, at least 30%, at least 40%, at least 50%, at least 60%, at least 70%, at least 80% or at least 90% or more.

Before administration of a full dose of the C5 inhibitor and/or C5 inhibitor composition, patients can be administered a smaller dose, such as 5% of a full dose, and monitored for adverse effects, such as an allergic reaction or infusion reaction, or for elevated lipid levels or blood pressure. In another example, the patient can be monitored for unwanted immunostimulatory effects, such as increased cytokine (e.g., TNF-alpha, Il-1, Il-6, or Il-10) levels.

Genetic predisposition plays a role in the development of some diseases or disorders. Therefore, a patient in need of a C5 inhibitor may be identified by taking a family history, or, for example, screening for one or more genetic markers or variants. A healthcare provider, such as a doctor, nurse, or family member, may analyze family history before prescribing or administering a therapeutic composition of the present invention.

III. Kits

Any of the C5 inhibitors described herein may be provided as part of a kit. In a non-limiting example, C5 inhibitors may be included in a kit for treating a disease. The kit may include a vial of sterile, dry C5 inhibitor powder, sterile solution for dissolving the dried powder, and a syringe for infusion set for administering the C5 inhibitor.

When C5 inhibitors are provided as a dried powder it is contemplated that between 10 micrograms and 1000 milligrams of C5 inhibitor, or at least or at most those amounts are provided in kits of the invention Typical kits may include at least one vial, test tube, flask, bottle, syringe and/or other container or device, into which the C5 inhibitor formulations are placed, preferably, suitably allocated. Kits may also include one or more secondary containers with sterile, pharmaceutically acceptable buffer and/or other diluent.

In some embodiments, compounds or compositions of the invention are provided in borosilicate vials. Such vials may include a cap (e.g., a rubber stopper). In some cases, caps include FLUROTEC® coated rubber stoppers. Caps may be secured in place with an overseal, including, but not limited to an aluminum flip-off overseal.

Kits may further include instructions for employing the kit components as well the use of any other reagent not included in the kit. Instructions may include variations that can be implemented.

IV. Definitions

Bioavailability: As used herein, the term "bioavailability" refers to the systemic availability of a given amount of a compound (e.g., C5 inhibitor) administered to a subject. Bioavailability can be assessed by measuring the area under the curve (AUC) or the maximum serum or plasma concentration ($C_{max}$) of the unchanged form of a compound following administration of the compound to a subject. AUC is a determination of the area under the curve when plotting the serum or plasma concentration of a compound along the ordinate (Y-axis) against time along the abscissa (X-axis). Generally, the AUC for a particular compound can be calculated using methods known to those of ordinary skill in the art and/or as described in G. S. Banker, Modern Pharmaceutics, Drugs and the Pharmaceutical Sciences, v. 72, Marcel Dekker, New York, Inc., 1996, the contents of which are herein incorporated by reference in their entirety.

Biological system: As used herein, the term "biological system" refers to a cell, a group of cells, a tissue, an organ, a group of organs, an organelle, a biological fluid, a biological signaling pathway (e.g., a receptor-activated signaling pathway, a charge-activated signaling pathway, a metabolic pathway, a cellular signaling pathway, etc.), a group of proteins, a group of nucleic acids, or a group of molecules (including, but not limited to biomolecules) that carry out at least one biological function or biological task within cellular membranes, cellular compartments, cells, cell cultures, tissues, organs, organ systems, organisms, multicellular organisms, biological fluids, or any biological entities. In some embodiments, biological systems are cell signaling pathways comprising intracellular and/or extracellular signaling biomolecules. In some embodiments, biological systems include proteolytic cascades (e.g., the complement cascade).

Buffering agent: As used herein, the term "buffering agent" refers to a compound used in a solution for the purposes of resisting changes in pH. Such compounds may include, but are not limited to acetic acid, adipic acid, sodium acetate, benzoic acid, citric acid, sodium benzoate, maleic acid, sodium phosphate, tartaric acid, lactic acid, potassium metaphosphate, glycine, sodium bicarbonate, potassium phosphate, sodium citrate, and sodium tartrate.

Clearance rate: As used herein, the term "clearance rate" refers to the velocity at which a particular compound is cleared from a biological system or fluid.

Compound: As used herein, the term "compound," refers to a distinct chemical entity. In some embodiments, a particular compound may exist in one or more isomeric or isotopic forms (including, but not limited to stereoisomers, geometric isomers and isotopes). In some embodiments, a compound is provided or utilized in only a single such form. In some embodiments, a compound is provided or utilized as a mixture of two or more such forms (including, but not limited to a racemic mixture of stereoisomers). Those of skill in the art will appreciate that some compounds exist in different forms, show different properties and/or activities (including, but not limited to biological activities). In such cases it is within the ordinary skill of those in the art to select or avoid particular forms of a compound for use in accordance with the present invention. For example, compounds that contain asymmetrically substituted carbon atoms can be isolated in optically active or racemic forms.

Cyclic or Cyclized: As used herein, the term "cyclic" refers to the presence of a continuous loop. Cyclic molecules need not be circular, only joined to form an unbroken chain of subunits. Cyclic polypeptides may include a "cyclic loop," formed when two amino acids are connected by a bridging moiety. The cyclic loop comprises the amino acids along the polypeptide present between the bridged amino acids. Cyclic loops may comprise 2, 3, 4, 5, 6, 7, 8, 9, 10 or more amino acids.

Downstream event: As used herein, the term "downstream" or "downstream event," refers to any event occurring after and/or as a result of another event. In some cases, downstream events are events occurring after and as a result of C5 cleavage and/or complement activation. Such events may include, but are not limited to generation of C5 cleavage products, activation of MAC, hemolysis, and hemolysis-related disease (e.g., PNH).

Equilibrium dissociation constant: As used herein, the term "equilibrium dissociation constant" or "$K_D$" refers to a value representing the tendency of two or more agents (e.g., two proteins) to reversibly separate. In some cases, $K_D$ indicates a concentration of a primary agent at which half of the total levels of a secondary agent are associated with the primary agent.

Half-life: As used herein, the term "half-life" or "$t_{1/2}$" refers to the time it takes for a given process or compound concentration to reach half of a final value. The "terminal half-life" or "terminal $t_{1/2}$" refers to the time needed for the plasma concentration of a factor to be reduced by half after the concentration of the factor has reached a pseudo-equilibrium.

Hemolysis: As used herein, the term "hemolysis" refers to the destruction of red blood cells.

Identity: As used herein, the term "identity," when referring to polypeptides or nucleic acids, refers to a comparative relationship between sequences. The term is used to describe the degree of sequence relatedness between polymeric sequences, and may include the percentage of matching monomeric components with gap alignments (if any) addressed by a particular mathematical model or computer program (i.e., "algorithms"). Identity of related polypeptides can be readily calculated by known methods. Such methods include, but are not limited to, those described previously by others (Lesk, A. M., ed., Computational Molecular Biology, Oxford University Press, New York, 1988; Smith, D. W., ed., Biocomputing: Informatics and Genome Projects, Academic Press, New York, 1993; Griffin, A. M. et al., ed., Computer Analysis of Sequence Data, Part 1, Humana Press, New Jersey, 1994; von Heinje, G., Sequence Analysis in Molecular Biology, Academic Press, 1987; Gribskov, M. et al., ed., Sequence Analysis Primer, M. Stockton Press, New York, 1991; and Carillo et al., Applied Math, SIAM J, 1988, 48, 1073).

Inhibitor: As used herein, the term "inhibitor" refers to any agent that blocks or causes a reduction in the occurrence of a specific event; cellular signal; chemical pathway; enzymatic reaction; cellular process; interaction between two or more entities; biological event; disease; disorder; or condition.

Intravenous: As used herein, the term "intravenous" refers to the area within a blood vessel. Intravenous administration typically refers to delivery of a compound into the blood through injection in a blood vessel (e.g., vein).

In vitro: As used herein, the term "in vitro" refers to events that occur in an artificial environment (e.g., in a test tube or reaction vessel, in cell culture, in a Petri dish, etc.), rather than within an organism (e.g., animal, plant, or microbe).

In vivo: As used herein, the term "in vivo" refers to events that occur within an organism (e.g., animal, plant, or microbe or cell or tissue thereof).

Lactam bridge: As used herein, the term "lactam bridge" refers to an amide bond that forms a bridge between chemical groups in a molecule. In some cases, lactam bridges are formed between amino acids in a polypeptide.

Linker: The term "linker" as used herein refers to a group of atoms (e.g., 10-1,000 atoms), molecule(s), or other compounds used to join two or more entities. Linkers may join such entities through covalent or non-covalent (e.g., ionic or hydrophobic) interactions. Linkers may include chains of two or more polyethylene glycol (PEG) units. In some cases, linkers may be cleavable.

Minute volume: As used herein, the term "minute volume" refers to the volume of air inhaled or exhaled from a subject's lungs per minute.

Non-proteinogenic: As used herein, the term "non-proteinogenic" refers to any unnatural proteins, such as those with unnatural components, such as unnatural amino acids.

Patient: As used herein, "patient" refers to a subject who may seek or be in need of treatment, requires treatment, is receiving treatment, will receive treatment, or a subject who is under the care of a trained professional for a particular disease or condition.

Pharmaceutical composition: As used herein, the term "pharmaceutical composition" refers to a composition comprising at least one active ingredient (e.g., a C5 inhibitor) in a form and amount that permits the active ingredient to be therapeutically effective.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than active agents (e.g., R5000 or variants thereof) present in a pharmaceutical composition and having the properties of being substantially nontoxic and non-inflammatory in a patient. In some embodiments, a pharmaceutically acceptable excipient is a vehicle capable of suspending or dissolving the active agent. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Plasma compartment: As used herein, the term "plasma compartment" refers to intravascular space occupied by blood plasma.

Salt: As used herein, the term "salt" refers to a compound made up of a cation with a bound anion. Such compounds may include sodium chloride (NaCl) or other classes of salts including, but not limited to acetates, chlorides, carbonates, cyanides, nitrites, nitrates, sulfates, and phosphates.

Sample: As used herein, the term "sample" refers to an aliquot or portion taken from a source and/or provided for analysis or processing. In some embodiments, a sample is from a biological source such as a tissue, cell or component part (e.g., a body fluid, including but not limited to blood, mucus, lymphatic fluid, synovial fluid, cerebrospinal fluid, saliva, amniotic fluid, amniotic cord blood, urine, vaginal fluid and semen). In some embodiments, a sample may be or comprise a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, or organs. In some embodiments, a sample is or comprises a medium, such as a nutrient broth or gel, which may contain cellular components, such as proteins. In some embodiments, a "primary" sample is an aliquot of the source. In some embodiments, a primary sample is subjected to one or more processing (e.g., separation, purification, etc.) steps to prepare a sample for analysis or other use.

Subcutaneous: As used herein, the term "subcutaneous" refers to the space underneath the skin. Subcutaneous administration is delivery of a compound beneath the skin.

Subject: As used herein, the term "subject" refers to any organism to which a compound in accordance with the invention may be administered, e.g., for experimental, diagnostic, prophylactic, and/or therapeutic purposes. Typical subjects include animals (e.g., mammals such as mice, rats, rabbits, porcine subjects, non-human primates, and humans).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially"

is therefore used herein to capture the potential lack of completeness inherent in many biological and chemical phenomena.

Therapeutically effective amount: As used herein, the term "therapeutically effective amount" means an amount of an agent to be delivered (e.g., C5 inhibitor) that is sufficient, when administered to a subject suffering from or susceptible to a disease, disorder, and/or condition, to treat, improve symptoms of, diagnose, prevent, and/or delay the onset of the disease, disorder, and/or condition.

Tidal volume: As used herein, the term "tidal volume" refers to the normal lung volume of air displaced between breaths (in the absence of any extra effort).

$T_{max}$: As used herein, the term "$T_{max}$" refers to the time period for which maximum concentration of a compound in a subject or fluid is maintained.

Treating: As used herein, the term "treating" refers to partially or completely alleviating, ameliorating, improving, relieving, delaying onset of, inhibiting progression of, reducing severity of, and/or reducing incidence of one or more symptoms or features of a particular disease, disorder, and/or condition. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Volume of distribution: As used herein, the term "volume of distribution" or "$V_{dist}$" refers to a fluid volume required to contain the total amount of a compound in the body at the same concentration as in the blood or plasma. The volume of distribution may reflect the extent to which a compound is present in the extravascular tissue. A large volume of distribution reflects the tendency of a compound to bind to tissue components compared with plasma protein components. In a clinical setting, $V_{dist}$ can be used to determine a loading dose of a compound to achieve a steady state concentration of that compound.

V. Equivalents and Scope

While various embodiments of the invention have been particularly shown and described, it will be understood by those skilled in the art that various changes in form and details may be made therein without departing from the spirit and scope of the invention as defined by the appended claims.

Those skilled in the art will recognize, or be able to ascertain using no more than routine experimentation, many equivalents to the specific embodiments in accordance with the invention described herein. The scope of the present invention is not intended to be limited to the above description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the terms "consisting of" and "or including" are thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1. Preparation of R5000 Aqueous Solution

Polypeptides were synthesized using standard solid-phase Fmoc/tBu methods. The synthesis was performed on a Liberty automated microwave peptide synthesizer (CEM, Matthews N.C.) using standard protocols with Rink amide resin, although other automated synthesizers without microwave capability may also be used. All amino acids were obtained from commercial sources. The coupling reagent used was 2-(6-chloro-1-H-benzotriazole-1yl)-1,1,3,3,-tetramethylaminium hexafluorophosphate (HCTU) and the base was diisopropylethylamine (DIEA). Polypeptides were cleaved from resin with 95% TFA, 2.5% TIS and 2.5% water for 3 hours and isolated by precipitation with ether. The crude polypeptides were purified on a reverse phase preparative HPLC using a C18 column, with an acetonitrile/water 0.1% TFA gradient from 20%-50% over 30 min. Fractions containing pure polypeptides were collected and lyophilized and all polypeptides were analyzed by LC-MS.

R5000 (SEQ ID NO: 1) was prepared as a cyclic peptide containing 15 amino acids (4 of which are unnatural amino acids), an acetylated N-terminus, and a C-terminal carboxylic acid. The C-terminal lysine of the core peptide has a modified side chain, forming a N-ε-(PEG24-γ-glutamic acid-N-α-hexadecanoyl) lysine reside. This modified side chain includes a polyethyleneglycol spacer (PEG24) attached to an L-γ glutamic acid residue that is derivatized with a palmitoyl group. The cyclization of R5000 is via a lactam bridge between the side-chains of L-Lys1 and L-Asp6. All of the amino acids in R5000 are L-amino acids. R5000 has a molecular weight of 3562.23 g/mol and a chemical formula of $C_{172}H_{278}N_{24}O_{55}$.

Like eculizumab, R5000 blocks the proteolytic cleavage of C5 into C5a and C5b. Unlike eculizumab, R5000 can also bind to C5b and block C6 binding which prevents the subsequent assembly of the MAC.

R5000 was prepared as an aqueous solution for injection containing 40 mg/mL of R5000 in a formulation of 50 mM sodium phosphate and 75.7 mM sodium chloride at a pH of 7.0±0.3.

Example 2. R5000 Administration and Storage

R5000 is administered by subcutaneous (SC) or intravenous (IV) injection and the dose administered (dose volume) is adjusted based on subject weight on a mg/kg basis. This is achieved using a set of fixed doses aligned to a set of weight brackets. In total, human dosing supports a broad weight range of 43 to 109 kg. Subjects who present with a higher body weight (>109 kg) are accommodated on a case-by-case basis, in consultation with a medical monitor.

R5000 is stored at 2° C. to 8° C. [36 to 46° F.]. Once dispensed to subjects, R5000 is stored at controlled room temperature (20° C. to 25° C. [68° F. to 77° F.]) for up to 30 days, and is protected from sources of excessive temperature fluctuations such as high heat or exposure to light. Storage of R5000 outside of room temperatures is preferably avoided. R5000 may be stored for up to 30 days under these conditions.

Example 3. Stability Testing

Stability testing is carried out according to the International Conference on Harmonisation (ICH) Q1A "Stability of New Drug Substances and Products." Samples from the aqueous solution of Example 1 are held at 3 temperatures: −20° C., 5° C., and 25° C. Testing intervals are at 1, 2, and 3 months, and thereafter every 3 months up to 24 months. Samples are tested for appearance (e.g., clarity, color, presence of precipitate), pH, osmolality, concentration, purity, target activity (e.g., by RBC lysis assay), particulate levels, endotoxin levels, and sterility. Samples are considered stable if, at each of the temperature conditions tested, the samples have a clear, colorless appearance with no visible particles; a pH of 7±0.3; an osmolality of 260 to 340 mOsm/kg; a purity of ≥95% (and no single impurity >3%); target activity that is comparable to a reference standard; particulate levels of ≤6,000 particulates per vial for ≥10 μm particles and levels of ≤600 particulates per vial for ≥25 μm particles; endotoxin levels of ≤100 EU/mL; and no microorganism growth.

Example 4. Freeze-Thaw Stability

A study was conducted to test stability of the aqueous solution of Example 1 when exposed to multiple freezing and thawing cycles. R5000 showed no degradation or other changes after 5 cycles of freezing and thawing.

Example 5. Surface Plasmon Resonance (SPR)-Based Binding Evaluation

The binding interaction between R5000 and C5 was measured using surface plasmon resonance. R5000 bound C5 with an equilibrium dissociation constant ($K_D$) of 0.42 nM at 25° C. (n=3) and a $K_D$ of 0.78 nM at 37° C. (n=3). Overall surface plasmon resonance data, when combined with analysis of a high-resolution co-crystal structure, indicate that R5000 exhibits specific, strong and rapid association with C5 as well as a slow dissociation rate.

Example 6. Evaluation of C5 Cleavage Inhibition

Figure 2:
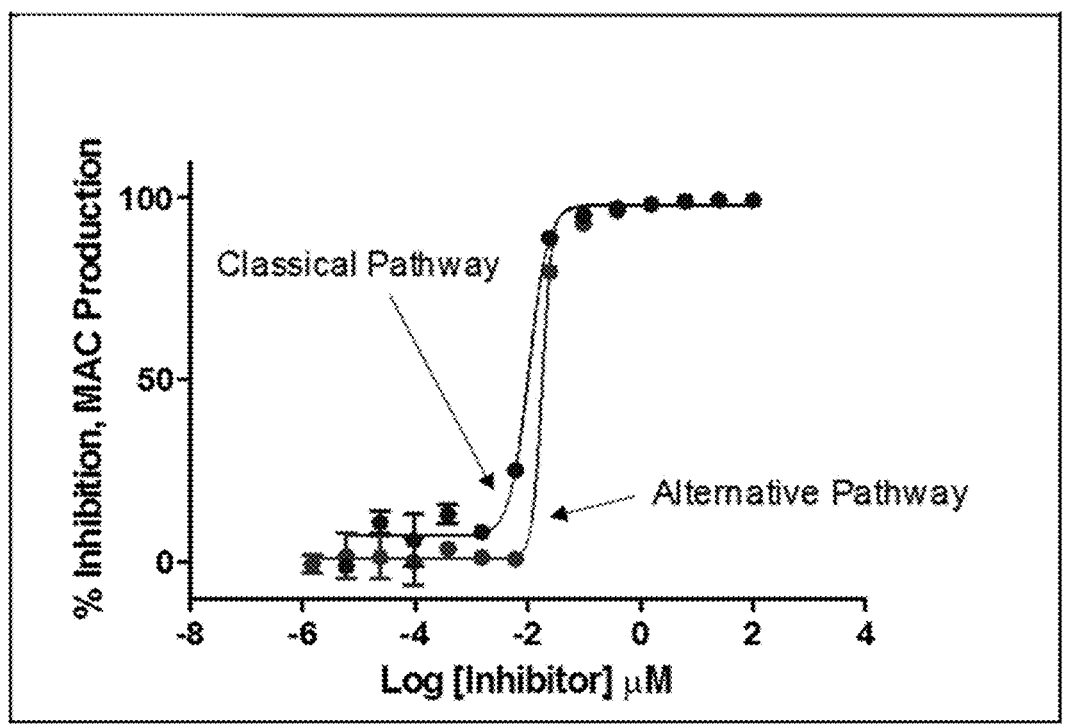
FIG. 2 is a scatter plot showing R5000 inhibition of membrane attack complex formation.

R5000 was assessed for inhibition of C5 cleavage to C5a and C5b. The inhibitory activity of R5000 with host C5 is an important factor in choosing appropriate animal models for drug safety. The inhibition of C5 cleavage is the basis for the clinical efficacy for eculizumab, currently the only approved therapy for the treatment of PNH. R5000 demonstrated a dose-dependent inhibition of C5a formation following activation of the Classical Pathway ($IC_{50}$=4.8 nM; FIG. 1) and a dose dependent inhibition of C5b (as measured by C5b-9 or MAC formation) upon activation of the Classical and Alternative complement pathways ($IC_{50}$=5.1 nM; FIG. 2).

Example 7. Inhibition of Complement-Induced Red Blood Cell (RBC) Hemolysis

The RBC lysis assay is a reliable method to screen complement inhibitors in sera/plasma from various species and compare relative activities of the test article. An in vitro functional assay was used in order to assess the inhibitory activity of peptides, including R5000, against complement function in several species. This assay tests the functional capability of complement components of the classical pathway to lyse sheep RBCs pre-coated with rabbit anti-sheep RBC antibodies. When antibody-coated RBCs are incubated with test serum, the classical pathway of complement is activated and hemolysis results and is monitored by release of hemoglobin. Antibody-sensitized sheep red blood cells were used as the vehicle for lysis in this assay and the sera and/or plasma from various species were used at their predetermined 50% hemolytic complement activity ($CH_{50}$).

R5000 demonstrated potent inhibition of complement-induced RBC hemolysis in the serum and/or plasma of human, non-human primates, and pigs (see the following Table).

TABLE 1

Inhibition of red blood cell hemolysis by R5000 in multiple species

| Species | $IC_{50}$ (nM) |
| --- | --- |
| Human | 6.6 |
| Non-human primate (4 species) | 3.5 to 17.6 |
| Dog | >4700 |
| Rabbit | >67000 |
| Porcine (2 species) | 51.9 to 118.6 |
| Rodents (3 species) | 591 to >100000 |

Weak activity was observed in rat plasma (>100 times lower than *Cynomolgus* monkey) and little to no activity was seen in other rodents, dog, or rabbit. Structural data obtained from a co-crystallization of human C5 with a molecule closely related to R5000 provided an explanation for this species selectivity through a careful analysis of the primary amino acid sequence at the drug-binding site of the target protein. While primate sequences are 100% conserved within residues responsible for R5000 interactions, there were significant differences in these residues in rodents and particularly in dog where identical portions of the protein do not exist. These amino acid differences were sufficient to explain the activity profiles of R5000 in different species.

The ability of R5000 to inhibit complement-mediated lysis of erythrocytes via the classical and alternative complement activation pathways was also tested. The classical pathway was evaluated using two different assays utilizing antibody-sensitized sheep erythrocytes. In one method, hemolysis was evaluated using 1% normal human serum, while the second assay utilized 1.5% C5-depleted human sera containing 0.5 nM human C5. The inhibition of the alternative complement activation pathway was evaluated using rabbit erythrocytes in 6% normal human serum in the absence of calcium (see the following Table).

TABLE 2

Inhibition of hemolysis by R5000 in complement activation pathways

| Pathway | $IC_{50}$ |
|---|---|
| Classical pathway | 4.9 |
| C5-depleted sera-classical pathway | 2.4 |
| Alternative pathway | 59.2 |

R5000 demonstrated complement mediated lysis in both, the classical pathway assays and the alternative pathway assay.

Example 8. Pharmacodynamics in Cynomolgus Monkeys

Figure 3:
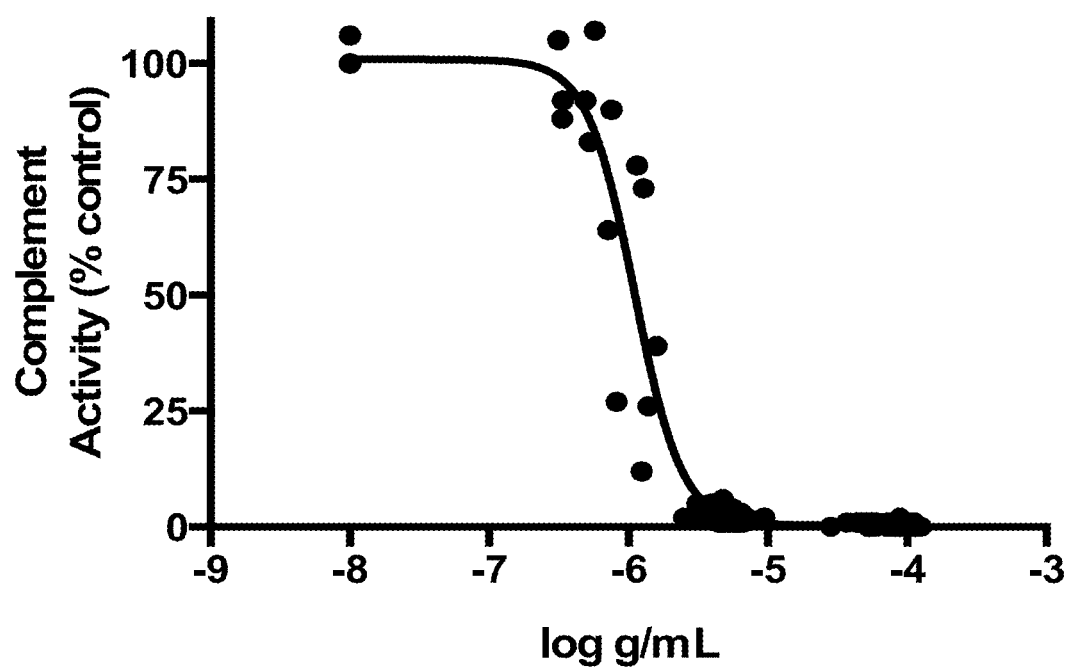
FIG. 3 is a scatter plot showing R5000 inhibitor activity in a *Cynomolgus* monkey model.

R5000 is a potent inhibitor of complement in primates, thus *Cynomolgus* monkeys were selected for multi-dose studies to evaluate the inhibitory activity of R5000 in an animal model. Plasma drug concentrations were determined by LC-MS and complement activity was assayed using the RBC lysis assay described in the previous Example. Overall results from these studies indicated that plasma drug levels should be at or greater than 2.5 μg/mL in monkeys to achieve >90% inhibition of complement activity (see FIG. 3).

Figure 4A:
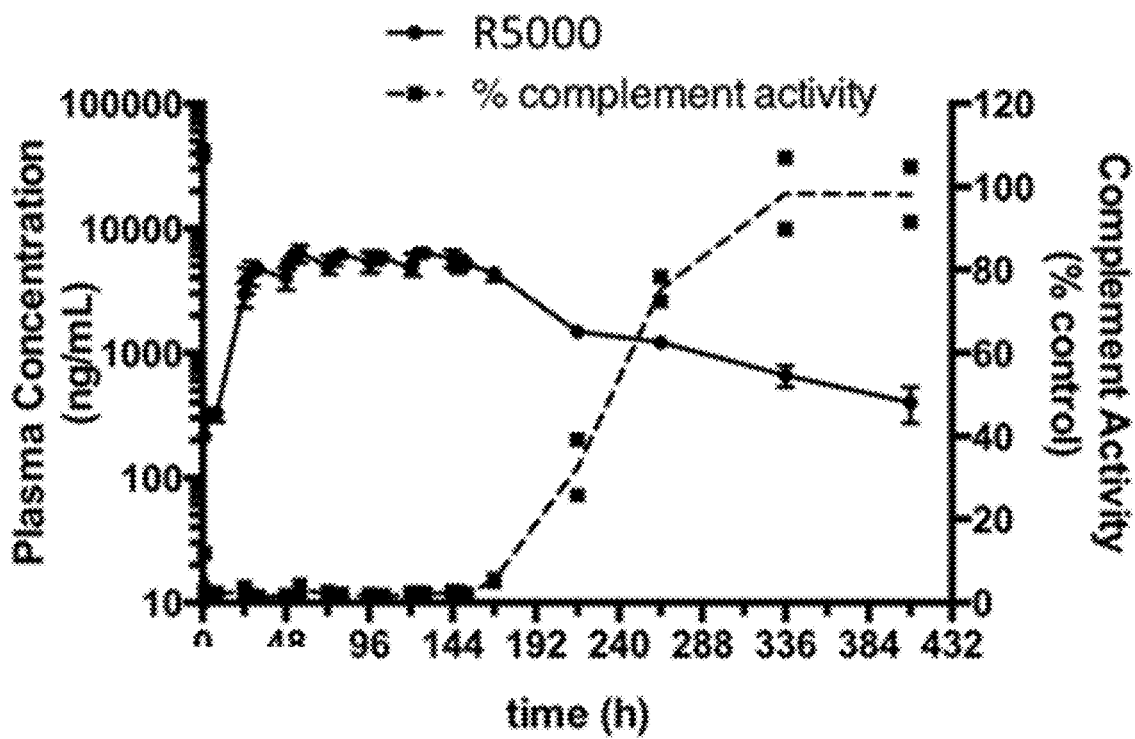
FIG. 4A is a scatter plot showing pharmacokinetic and pharmacodynamic correlation of R5000 in male *Cynomolgus* monkeys following multiple subcutaneous administrations at 0.21 mg/kg.
Figure 4B:
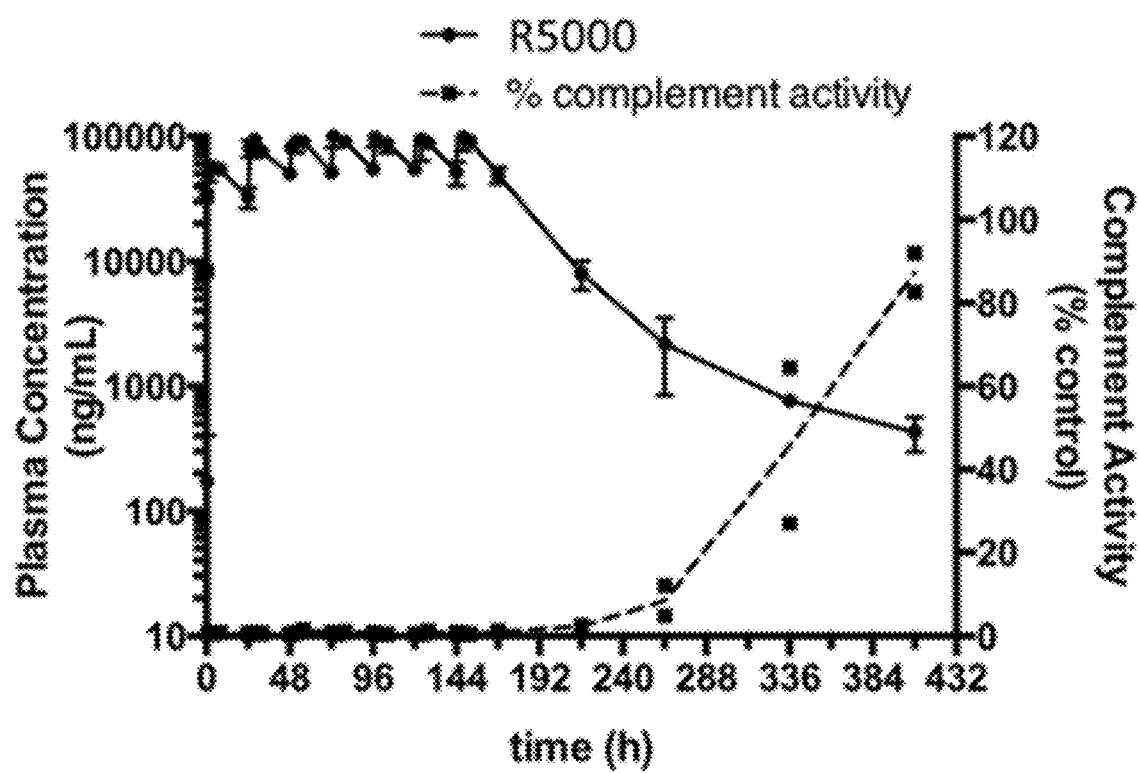
FIG. 4B is a scatter plot showing pharmacokinetic and pharmacodynamic correlation of R5000 in male *Cynomolgus* monkeys following multiple subcutaneous administrations at 4.2 mg/kg.

R5000 was administered to *Cynomolgus* monkeys at multiple daily doses through subcutaneous injections (SC) in a 7-day study. Blood samples were analyzed for hemolysis as an indicator of complement activity at the indicated time points (for days 1, 4, and 7, data are reported as days after first dose, but prior to dosing on the respective day) using an ex vivo sheep RBC lysis assay with 1% plasma in the assay. Drug levels were determined from the same sample using an LC-MS method specific for R5000. As shown in the following Table and in FIGS. 4A and 4B, when R5000 was administered daily for 7 days at either 0.21 or 4.2 mg/kg, minimal (<3% of pre-dose) complement activity was seen throughout the dosing period.

>75% of baseline. This correlates well with the measured plasma levels for the compound during and after dosing (dotted line in FIG. 4A). The second group of animals in the multi-dose study was administered daily 4.2 mg/kg doses of R5000. In this group, hemolysis was essentially completely inhibited (at <1%) throughout dosing and remained below 3% at 48 hours after the last dose (Day 9; 216 hours in FIG. 4B). Four days after the final dose (264 hours in FIG. 4B), hemolysis reached approximately 10% of baseline. This result again demonstrated suppression of complement activity throughout the dosing period (as compared to pre-dose results) correlating with plasma drug concentrations and demonstrated an excellent correlation between pharmacokinetic and pharmacodynamic values.

Figure 7:
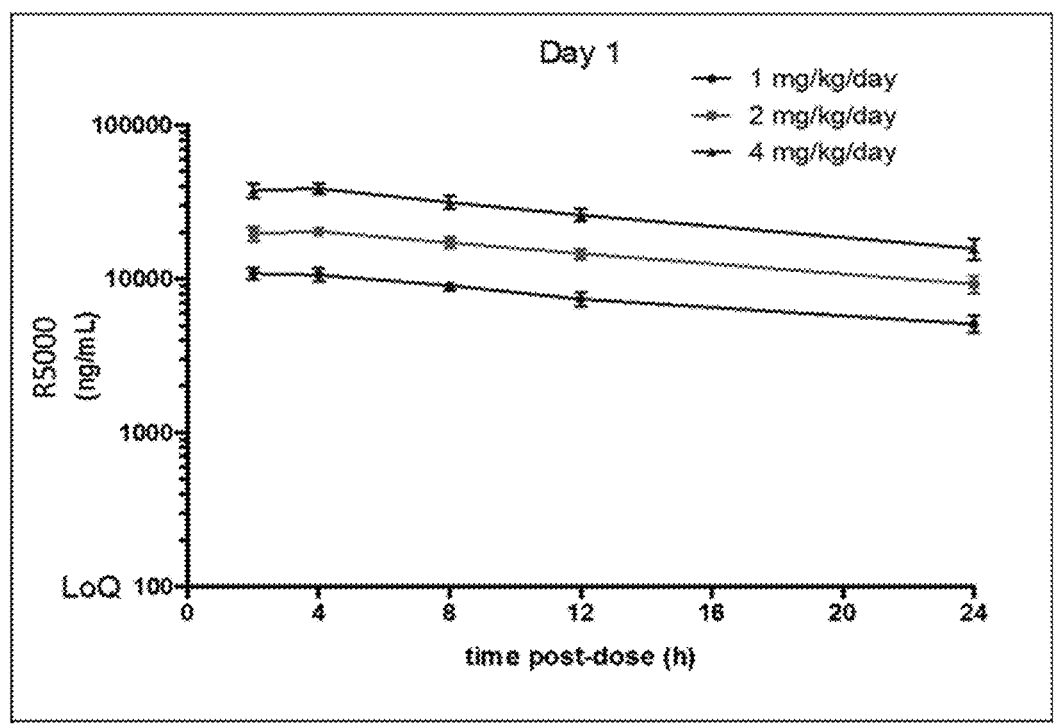
FIG. 7 is a line graph showing concentrations of R5000 in *Cynomolgus* monkey after a first dose in a repeat-dose toxicology study.
Figure 8:
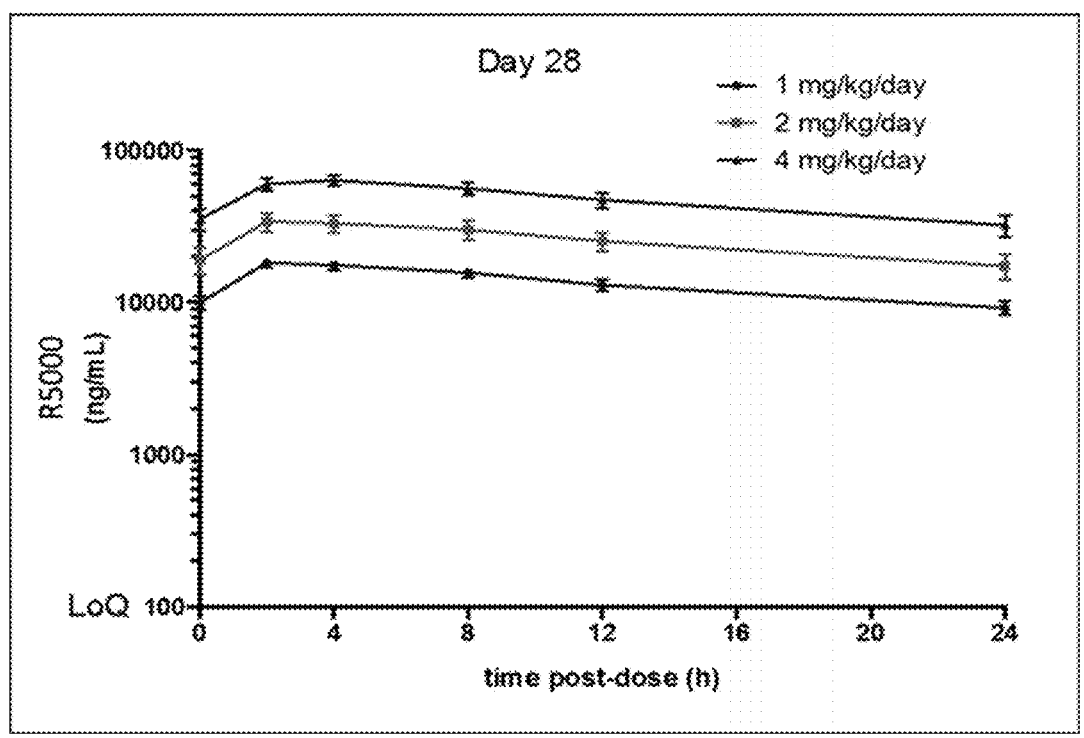
FIG. 8 is a line graph showing concentrations of R5000 in *Cynomolgus* monkey after the last dose in a repeat-dose toxicology study.

The complement inhibitory activity of R5000 was assessed in a 28 day-repeated-dose study in *Cynomolgus* monkey using the ex vivo RBC hemolysis assay. R5000 was administered daily via subcutaneous injection for 28 days at either 0, 1, 2, or 4 mg/kg/day (Day 1: FIG. 7 and Day 28: FIG. 8). Results demonstrated complete inhibition of hemolysis from 2 hours after administration of the first dose through 28 days of dosing, with hemolysis percentages of <5% in 1, 2, and 4 mg/kg/day groups, compared to >90% in the control group. After a 28-day recovery period, sample values returned to nearly baseline hemolysis levels and little to no inhibition of the complement system was observed. The absence of complement inhibition activity at the end of the recovery period indicated clearance of the drug from the animals.

Complement inhibition was also tested as part of a 13 week-repeated-dose study in the *Cynomolgus* monkey. Monkey samples were analyzed using the ex vivo RBC hemolysis assay. R5000 was administered daily via subcutaneous injection for 13 weeks at either 0, 0.25, 1, 2, or 10 mg/kg/day doses. Similar to the 28-day study, results from the 13-week study demonstrated complete inhibition of hemolysis ex vivo from 2 hours after administration of the first dose through 13 weeks of dosing, with hemolysis percentages of <5% in 0.25, 1, 2, and 10 mg/kg/day groups, compared to >90% in the control group. After a 28-day recovery period, sample values returned to nearly baseline hemolysis levels and little to no inhibition of the complement system was observed. The absence of complement inhibition activity at the end of the recovery period indicated clearance of the drug from the animals.

TABLE 3

Mean pharmacodynamic values

| | | | | % Hemolysis | | | | | | |
|---|---|---|---|---|---|---|---|---|---|---|
| # of Animals dosed | Daily Dose (mg/kg) | Route | Last point collected (days) | Day 1 | Day 4 | Day 7 | Day 8 | Day 12 | Day 14 | Day 18 |
| 2 | 0.21 | SC | 18 | 2.9 | 1.9 | 2.4 | 5.4 | 75.4 | >95 | >95 |
| 2 | 4.2 | SC | 18 | <1 | <1 | <1 | 1.1 | 8.7 | 45.7 | 87.3 |

Hemolysis in the ex vivo assay was maintained below 90% of baseline after the first dose in the 0.21 mg/kg group, throughout the dosing period, and up to 24 hours after the last dose. Increasing levels of hemolysis were seen after treatment was discontinued. By Day 4 (264 hours in FIG. 4A) after the last dose was administered, hemolysis was Example 9. Safety Pharmacology No adverse effects on cardiovascular, respiratory, or central nervous system parameters were observed when R5000 was administered to *Cynomolgus* monkeys. Safety pharmacology parameters were evaluated in vitro using the human ether-a-go-go related gene (hERG) assay and in vivo using monkeys for cardiovascular, respiratory, and CNS parameters. The CNS safety pharmacology assessment was conducted as part of a 28-day non-human primate toxicology study. A summary of the safety pharmacology studies with R5000 is presented in the following Table.

TABLE 4

Results from safety pharmacology studies

| Type of Study | Safety Parameter | Model | Highest Concentration Tested |
|---|---|---|---|
| Safety Pharmacology | Cardiovascular hERG assay | HEK293 cells | 300 μM (1.07 mg/mL) |
| | Cardiovascular | Monkey | 79.1 μg/mL |
| | Respiratory | | |
| | CNS | Monkey | 64.2 μg/mL |

The in vitro effect of R5000 on cloned hERG potassium channel current (a surrogate for $I_{Kr}$, the rapidly activating, delayed rectifier cardiac potassium current) expressed in human embryonic kidney 293 cells was evaluated using a parallel patch-clamp system. The highest tested concentration (300 μM) did not result in hERG inhibition greater than 50%, and the $IC_{50}$ for R5000 was therefore estimated to be greater than 300 μM (1.07 mg/mL).

The in vivo cardiovascular and respiratory safety pharmacology study was conducted in conscious male *Cynomolgus* monkeys. There were no deaths and no significant clinical events following administration of R5000. No R5000-related effects on the morphology and complete heartbeat intervals were seen at any of the R5000 doses (2 or 10 mg/kg on day 1 and day 8). Only normal, circadian variations were observed in electrocardiograms and body temperatures (comparable to vehicle-treated readings). In addition, there were no changes in heart rate and arterial blood pressure that could be attributed to R5000 at doses up to 10 mg/kg and at plasma drug levels of up to 79.1 μg/mL.

There were no changes in any of the respiratory parameters (respiratory rate, tidal volume and minute volume) following treatment with R5000 at 2 or 10 mg/kg compared to pre-dose or to values obtained subsequent to the administration of vehicle.

R5000 was administered via daily subcutaneous injection to *Cynomolgus* monkeys at 1, 2, or 4 mg/kg/day and its effects on the central nervous system (CNS) were studied. Parameters for evaluation included general attitude, behavior, motor functions, cranial nerves, proprioception, postural reactions and spinal nerves. There were no neurological alterations observed following treatment with R5000.

In conclusion, the subcutaneous (SC) injection of R5000 at dose levels up to 10 mg/kg which resulted in a $C_{max}$ of 79.1 μg/mL was well tolerated and did not result in any adverse effects on the cardiovascular (with no elevated risk of QT prolongation, a measure of delayed ventricular repolarization), respiratory, or central nervous systems of conscious *Cynomolgus* monkeys.

Example 10. Pharmacokinetics and Drug Metabolism in Animals

Studies evaluating the in vitro and in vivo absorption, distribution, metabolism, and excretion of R5000 are listed in the following Table. In the following Table, CYP refers to the cytochrome P450 enzyme and UGT refers to the UDP-glucuronosyltransferase enzyme.

TABLE 5

R5000 nonclinical drug metabolism and pharmacokinetic (DMPK) studies

| Type of Study | Test System | Substrate/Method of Administration |
|---|---|---|
| Absorption | Sprague-Dawley rat | SC; 1 and 10 mg/kg |
| | Cynomolgus monkey | IV, SC; 0.5 mg/kg |
| Distribution | Rat, monkey, and human protein binding; human blood to plasma partitioning | In vitro, plasma; in vitro, whole blood |
| Metabolism | Metabolic stability whole blood/plasma; Metabolic profiles: plasma | Rat, monkey, human Cynomolgus monkey |
| Excretion | Bile duct-cannulated Cynomolgus monkey | Cynomolgus monkey |
| Pharmacokinetic drug interactions | CYP and UGT inhibition | Human liver microsomes (CYP) and recombinant human enzyme (UGT) |

Figure 5B:
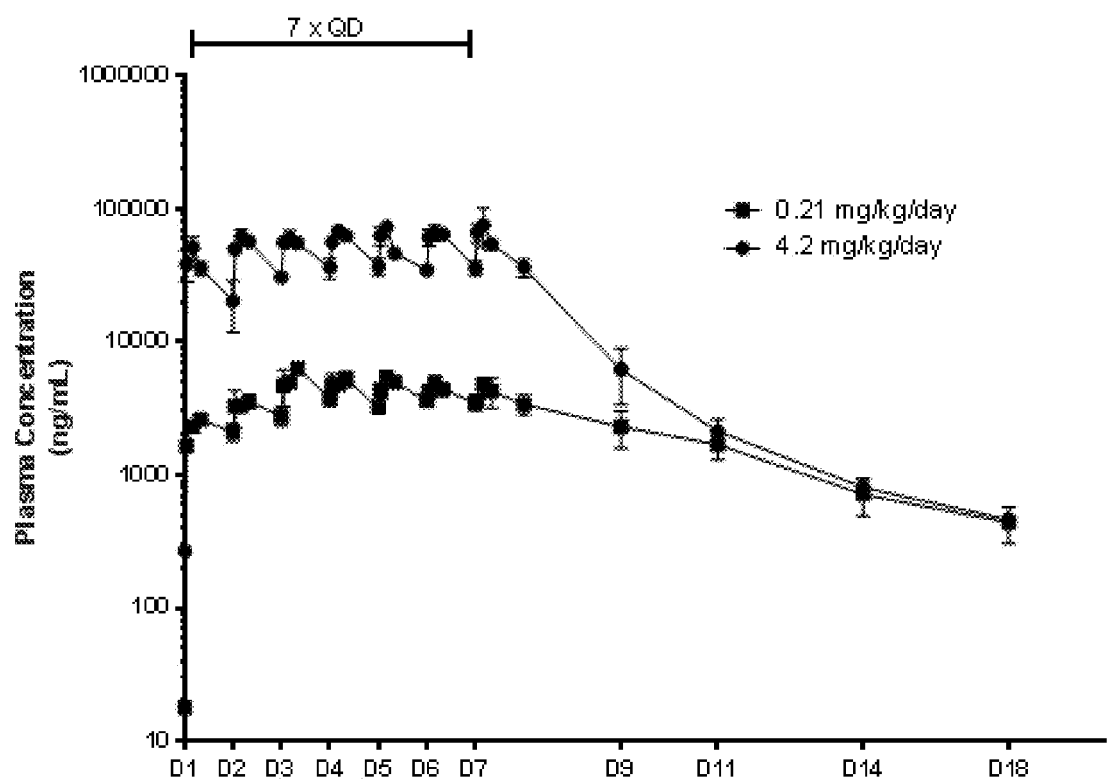
FIG. 5B is a graph showing plasma concentrations over time after subcutaneous multi dose administration at 0.21 and 4.2 mg/kg in monkeys.

Although R5000 is highly stable in vitro, in rat, monkey, and human plasma, the pharmacokinetic profile following intravenous (IV) and SC administration was different in monkey as compared to rat (FIG. 5A). The slow elimination kinetics seen in monkey was largely driven by high affinity interaction with the target protein C5 and other plasma proteins (e.g., albumin). The lack of specific target binding in the rat led to a faster elimination of R5000, which was reflected in a terminal $t_1$ of 4-5 hours as compared to >3 days in the monkey.

Overall, the preclinical data demonstrated high bioavailability (>75%) of R5000 following subcutaneous administration. In monkeys, maximum blood concentrations ($t_{max}$) are achieved between 8 and 16 hours post SC administration, indicating relatively slow absorption from the subcutaneous space. The aggregate data including volume of distribution, high degree of plasma protein binding, and partitioning into plasma compartment in whole blood indicate that R5000 is predominantly restricted to the plasma space, with little distribution into tissues.

Absorption

Pharmacokinetic (PK) studies were performed in rats (single dose) and *Cynomolgus* monkeys (single and multiple dose) using R5000 in phosphate buffered saline formulations (pH 7.0).

For rat studies, a single dose of R5000 was injected subcutaneously into male Sprague Dawley rats (n=3) at 1 mg/kg, or 10 mg/kg. The pharmacokinetic (PK) parameters measured included $C_{max}$ (maximum plasma drug concentration), $T_{max}$ (time taken to reach maximum plasma concentration following drug administration), $t_{1/2}$ (half-life), $AUC_{0-last}$ (Area under the plasma concentration-time curve between the first and last dose), and $AUC_{0-\infty}$ (Area under the plasma concentration-time curve from time zero to infinity). The results are summarized in the following Table.

TABLE 6

Pharmacokinetic parameters

| PK parameters (Mean) | Dose | |
|---|---|---|
|  | 1 mg/kg | 10 mg/kg |
| $C_{max}$ (ng/mL) | 5,303 | 45,567 |
| $T_{max}$ (hr) | 4.67 | 5.33 |
| $t_{1/2}$ (hr) | 9.54 | 9.27 |
| $AUC_{0\text{-}last}$ (ng * hr/mL) | 98,949 | 987,288 |
| $AUC_{0\text{-}\infty}$ (ng * hr/mL) | 99,217 | 988,530 |

The mean $AUC_{0\text{-}last}$ value at both 1 mg/kg and 10 mg/kg suggest a dose proportional exposure.

For primate studies, pharmacokinetic analysis was conducted in *Cynomolgus* monkeys after either single intravenous or subcutaneous dose of 0.4 or 0.5 mg/kg. The pharmacokinetic (PK) parameters measured included clearance (CL), $V_z$ (volume of distribution), $V_{ss}$ (apparent volume of distribution at steady state), $C_{max}$ (maximum plasma drug concentration), $T_{max}$ (time taken to reach maximum plasma concentration following drug administration), $t_{1/2}$ (half-life), $AUC_{0\text{-}last}$ (Area under the drug concentration versus time curve between the first and last dose), $AUC_{0\text{-}\infty}$ (Area under the drug concentration versus time curve from time zero to infinity), and % F (fractions). Results are presented in the following Table; NA indicates not applicable.

TABLE 7

Pharmacokinetic parameters in the Cynomolgus monkey

| PK parameter (Mean) | Dose (0.4 mg/kg) | |
|---|---|---|
|  | IV | SC |
| CL (mL/min/kg) | 0.011 | NA |
| $V_z$ (L/kg) | 175.5 | NA |
| $V_{ss}$ (mL/kg) | 163.5 | NA |
| $C_{max}$ (ng/mL) | 4,745.5 | 2,490 |
| $T_{max}$ (hr) | 0.25 | 8.0 |
| $t_{1/2}$ (hr) | 182.5 | 177.5 |
| $AUC_{0\text{-}last}$ (ng * hr/mL) | 429,638 | 325,317.5 |
| $AUC_{0\text{-}\infty}$ (ng * hr/mL) | 601,392.5 | 439,187 |
| % F | NA | 75.7 |

Single SC doses of 0.4 mg/kg resulted in plasma exposure ($AUC_{last}$) of R5000 following iv and sc doses was 429,638 and 325,317 ng*h/mL, respectively. Maximum plasma concentration ($C_{max}$) of R5000 following IV and SC dosing was 4,745.5 and 2,490 ng/mL, respectively, and the $T_{max}$ following SC dosing was 8 hours. Subcutaneous bioavailability at 0.4 mg/kg was determined to be 75.7%. Mean $t_{1/2}$ was 182.5 and 177.5 hours for IV and SC doses, respectively. Mean volume of distribution associated with terminal phase ($V_z$) and clearance (CL) for the IV dose was determined to be 175.5 mL/kg and 0.011 mL/min/kg, respectively. This profile contrasts with rat in which no appreciable binding was expected based on the in vitro activity studies and therefore the $t_{1/2}$ of R5000 was 4-5 hours (see FIG. 5A).

Repeated-dose pharmacokinetic studies in monkeys included two subcutaneous dose levels of 0.21 and 4.2 mg/kg administered every day over 7 days, with PK evaluated on each day and for 14 days following the last dose. In multiple-dose studies conducted in monkeys, $C_m$ax increased with subsequent doses until a steady-state peak and trough drug level was reached (after 2 to 3 doses; see FIGS. 4A, 4B, and 5B). Plasma concentrations in the 0.2 and 4 mg/kg dose groups reached an average $C_{max}$ after the first dose of 2,615 and 51,700 ng/mL, respectively. $C_{max}$ increased in both groups with each successive dose owing to the long half-life of the molecule. By the fourth dose, the mean $C_{max}$ for the 0.21 and 4.2 mg/kg dose groups was 5,305 and 68,750 ng/mL, or 2.0 and 1.3 times the first dose, respectively Overall, the absorption could be characterized as slow from the SC space, with high bioavailability of the SC dose.

Distribution

The in vitro plasma protein binding was >99.9% in human, rat, and monkey plasma, as determined by equilibrium dialysis at a drug concentration of 10 and 100 µM. The high protein binding and limited volume of distribution indicate that R5000 may be primarily restricted to the plasma compartment and does not readily distribute into the perivascular space.

Blood Partitioning

The ratio of drug partitioned between plasma and red blood cells was calculated, since it is a critical parameter required to evaluate the pharmacokinetic properties of a drug (see the following Table). In the following Table, RBC indicates red blood cells, P denotes plasma, and WB denotes whole blood.

TABLE 8

Blood Partitioning of R5000

| Species | Test Article Dosing Concentration (µM) | RBC to Plasma Partitioning ($K_{RBC/P}$) | Whole Blood to Plasma Partitioning ($K_{WB/P}$) |
|---|---|---|---|
| Human | 2 | 0.25 | 0.72 |
| Human | 20 | 0.20 | 0.70 |
| Human | 200 | 0.37 | 0.76 |

In whole blood partitioning assays R5000 was found to be predominantly present in the plasma fraction and did not show significant distribution into the erythrocyte fraction.

Pharmacokinetic Drug Interaction

A commonly administered medication in paroxysmal nocturnal hemoglobinuria (PNH) patients is cyclosporine (CsA). The potential for a drug-drug interaction between R5000 and CsA was evaluated in *Cynomolgus* monkeys since it is likely that R5000 will be coadministered with CsA in the PNH patients enrolled in the planned clinical trials.

R5000 (2 mg/kg, sc, single dose) and cyclosporine A (CsA) (15 mg/kg, sc, single dose) were administered independently or together in two male monkeys and plasma levels were evaluated using LC-MS/MS methods. No significant changes in the plasma exposure of either drug were observed, indicating low potential for a drug-drug interaction (see the following Table). In the following Table, $C_{max}$ indicates maximum plasma drug concentration and AUC indicates area under the plasma concentration-time curve, "a" adjacent difference in exposure indicates the ratio of exposures for R5000+cyclosporine/R5000. "b" adjacent the difference in exposure refers to the ratio of exposures for cyclosporine+R5000/cyclosporine.

TABLE 9

Effects of co-administration

| Parameter | R5000 alone | R5000 + Cyclosporine | Cyclosporine alone | R5000 + Cyclosporine |
|---|---|---|---|---|
| AUC (ng * h/mL) | | | | |
| Mean | 654,317 | 773,030 | 6,317 | 8,469 |
| Difference in Exposure[a] (%) | — | 118 | — | 134 |
| $C_{max}$ (ng * h/mL) | | | | |
| Mean | 15,150 | 12,550 | 248 | 306 |
| Difference in Exposure[b] (%) | — | 83 | — | 124 |

No changes were observed in the serum chemistry parameters including bilirubin (an endogenous substrate of OATP1 and OATP1B3), indicating that there was no additive effect of CsA and R5000 on these transporters. In summary, the co-administration of CsA with R5000 had low potential for drug-drug interaction, and was well tolerated with no effect on serum chemistry parameters at plasma levels near or above that expected in clinical use.

Figure 6:
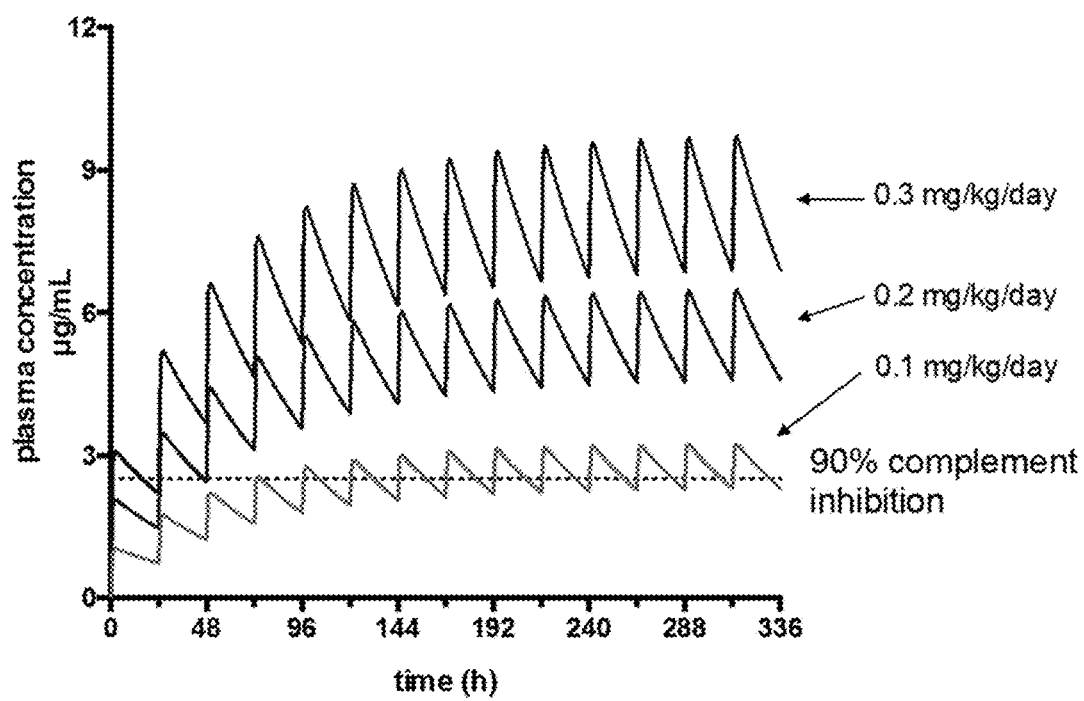
FIG. 6 is a graph showing predicted R5000 plasma concentrations in man with daily dosing of R5000.

Example 11. Pharmacokinetic/Pharmacodynamic Modeling and Simulation of Human Pharmacokinetics A PK/PD model was constructed in silico using in vivo data obtained in *Cynomolgus* monkeys. The model fit and accuracy were estimated by comparing simulated results to newly generated experimental data. Once validated in monkeys, the final model was used to predict human pharmacokinetics by applying allometric scaling to its parameters. The resulting simulations support a projected dosing interval of once daily or less frequently in humans, with daily doses of 0.1 mg/kg maintaining nearly 90% target inhibition at steady state (see FIG. 6). Because of the long half-life of R5000, several doses are necessary to reach final peak and trough drug levels. The plasma $C_{max}$ is expected to be approximately 3-fold higher following one week of daily dosing than the first dose as drug levels reach steady state.

Example 12. Effects in Humans: Phase I Clinical Trial Study Design

A randomized, placebo-controlled, double-blind, single-ascending dose, and multiple dose study was carried out to evaluate the safety and pharmacokinetics of R5000 in healthy volunteers, ages 18-65 (excluding pediatric and elderly individuals). In the first part of the study, single ascending dose (SAD) of R5000, or placebo, was administered to separate cohorts of subjects. In the second part of the study, a multiple-dose cohort (MD) was administered 0.2 mg/kg of R5000 (n=4) or placebo (n=2) each day for 7 days. All doses of R5000 were administered by subcutaneous injection with the dose volume determined by the dose requirements of the cohort and the weight of the subject. Subjects that were pregnant or nursing as well as any subjects with systemic infection or colonization with *Neisseria meningitides* were excluded. In addition, all subjects received prophylaxis with ciprofloxacin, and subjects in the highest single-dose cohort (i.e. 0.4 mg/kg) as well as the subjects in the multiple-dose cohort were vaccinated against *Neisseria meningitides* at least 14 days prior to the study.

A total of 22 subjects were enrolled in the single-dose cohort study (n=14), of which, 2 received R5000 at 0.05 mg/kg, 4 each at 0.10, 0.20, and 0.40 mg/kg. These doses were selected using estimated safety margins in humans (see previous Example and the following Table). In the following Table, $C_{max}$ indicates maximum plasma drug concentration and $AUC_{0-last}$ indicates area under the plasma concentration-time curve between the first and last dose.

TABLE 10

Comparisons of plasma exposure following multiple-doses at the NOAEL in animals and the highest proposed single clinical dose of 0.8 mg/kg

| Parameter, from 28-day study | Mean last day (Day 28) animal exposure at NOAEL (4 mg/kg) | Predicted human exposure at 0.8 mg/kg | Approximate margin |
|---|---|---|---|
| Monkey $C_{max}$ (µg/mL) | 64.2 | 8 | 8 |
| $AUC_{0-last}$ (µg * hr/mL) | 2140 | 413 | 5 |

The initial dose of 0.05 mg/kg is well below $\frac{1}{10}^{th}$ of the human equivalent dose (HED) estimate. This dose is considered appropriate because significant inhibition of complement was not expected at this dose. Systemic exposures predicted to follow the highest proposed single SC dose in the trial, 0.8 mg/kg, are exceeded by the final (Day 28) exposures at the NOAEL in monkeys.

In the multiple-dose cohort, 6 subjects were enrolled, of which 4 received R5000 (0.2 mg/kg) and 2 received placebo.

Example 13. Treating Patients with PNH

Patients suffering from PNH are treated with R5000 at an effective dose from 0.1 mg/kg/day to 40 mg/kg/day. Greater than or equal to 90% complement inhibition is observed in these patients and a $C_{max}$ of 3.1 µg/mL is reached.

Example 14. Multiple-Dose Clinical Study of R5000

A Phase 1 multiple-dose clinical pharmacology study in healthy human volunteers designed to evaluate the safety, tolerability, pharmacokinetics and pharmacokinetics and pharmacodynamics of R5000 following once daily subcutaneous (SC) injections over 7 was carried out. The study was single-center, randomized, double-blinded, and placebo (PBO)-controlled. Subjects received daily SC doses of 0.2 mg/kg R5000 or matching PBO for 7 days while housed in a clinical pharmacology unit. Safety was assessed by intensive clinical monitoring and daily blood samples were obtained immediately prior to dosing as well as, 3 hours, and 6 hours after each day's dose for determination of R5000 concentrations by liquid chromatography/high resolution mass spectroscopy and ability to inhibit complement-mediated RBC lysis in an ex vivo antibody-sensitized sheep erythrocyte hemolysis assay.

A total of 6 subjects were enrolled into the study (4 receiving R5000 and 2 receiving PBO). Subject demographics are presented in the following Table.

TABLE 11

Subject demographics

|  | Placebo treated, n = 2 | R5000 treated, n = 4 |
|---|---|---|
| Male:Female ratio | 0:2 | 1:3 |
| Mean Age, years (min, max) | 27 (25, 29) | 24 (22, 26) |
| Mean body mass index, kg/m² | 21 | 23 |
| White:Asian | 2:0 | 3:1 |

Figure 9A:
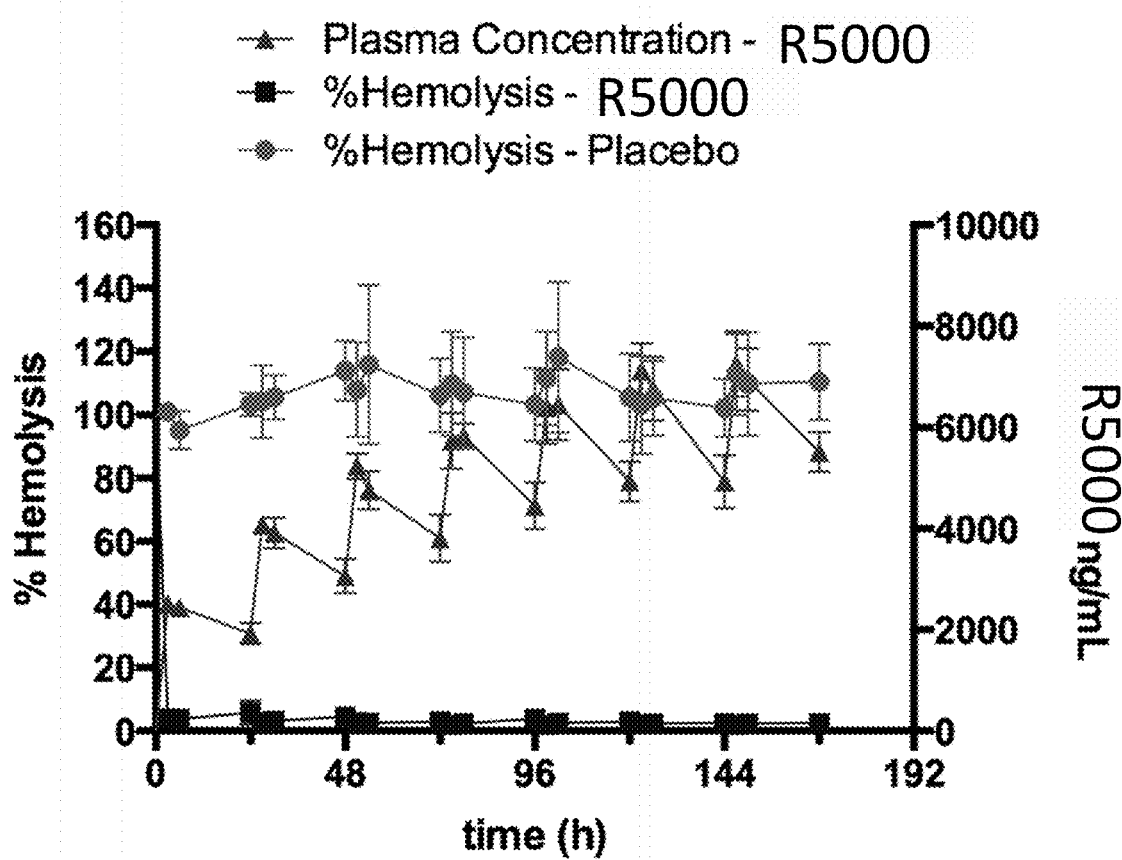
FIG. 9A is a graph showing changes in percent hemolysis in relation to R5000 concentration in a multi-dose human study.
Figure 9B:
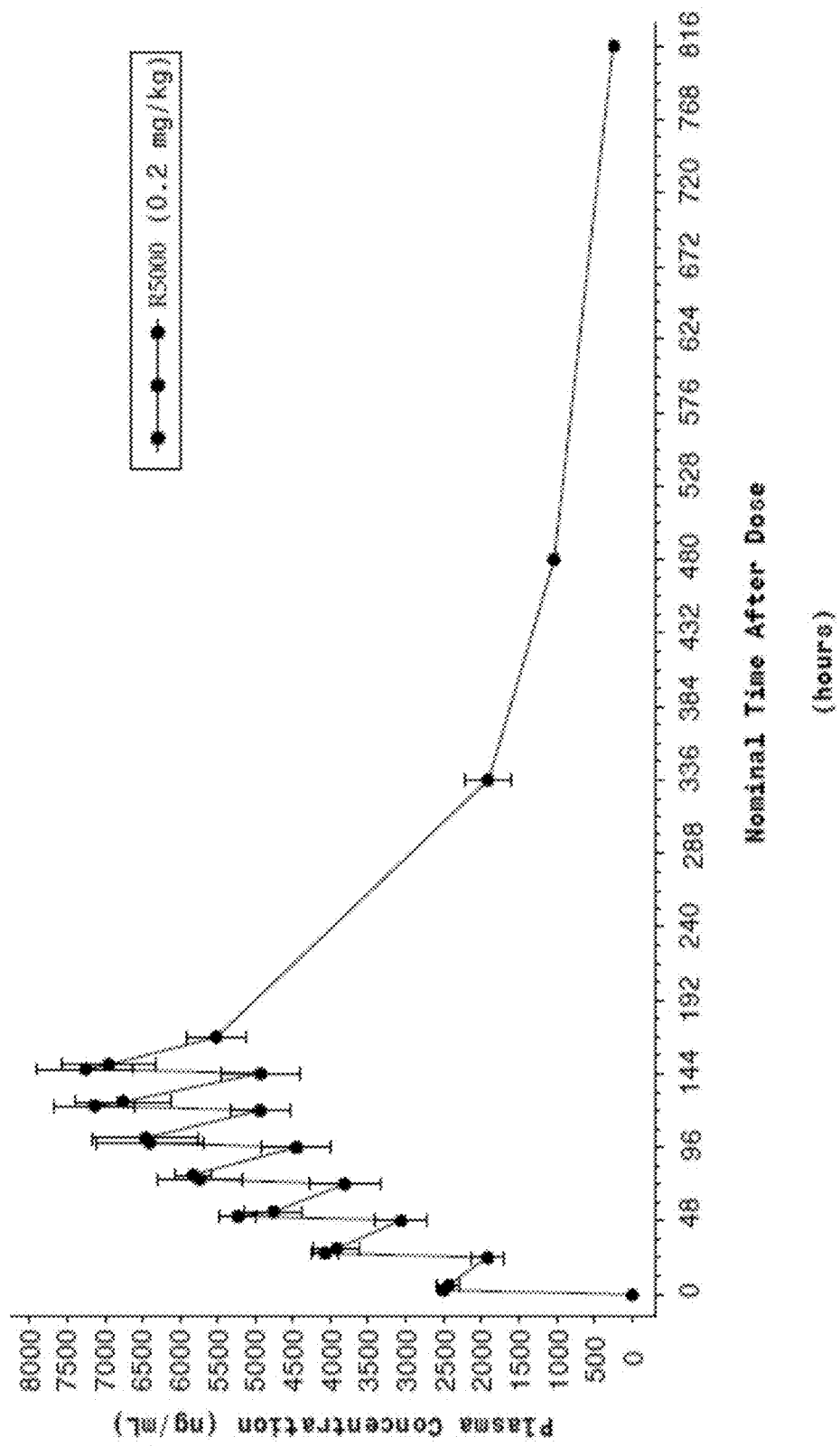
FIG. 9B is a graph showing plasma concentrations of R5000 over time in a multi-dose human study.

As seen in the following Table and related FIG. 9A (demonstrating percent hemolysis and plasma concentration over 7 days), plasma concentrations showed a steadily increasing exposure over the 7 days of dosing. From these data, the half-life of R5000 was determined to be 7 days. Plasma levels returned to around 2000 ng/ml by day 15 and around 1000 ng/ml by day 21 (FIG. 9B).

TABLE 12

Plasma concentrations of R5000

| Time Point | Concentration of R5000 (ng/ml) | | | |
|---|---|---|---|---|
| (hrs) | Subject 1 | Subject 2 | Subject 3 | Subject 4 |
| 0 | 0 | 0 | 0 | 0 |
| 3 | 2510 | 2410 | 2560 | 2520 |
| 6 | 2300 | 2390 | 2410 | 2650 |
| 24 | 1890 | 1750 | 1810 | 2220 |
| 27 | 3870 | 4050 | 4280 | 4110 |
| 30 | 3650 | 3730 | 4310 | 4000 |
| 48 | 2910 | 2650 | 3370 | 3330 |
| 51 | 5200 | 4910 | 5330 | 5500 |
| 54 | 4820 | 4220 | 5100 | 4900 |
| 72 | 3680 | 3340 | 3780 | 4460 |
| 75 | 6310 | 5240 | 5280 | 6110 |
| 78 | 5720 | 5570 | 5880 | 6140 |
| 96 | 4650 | 3790 | 4840 | 4540 |
| 99 | 6660 | 5320 | 6860 | 6770 |
| 102 | 7000 | 5440 | 6550 | 6820 |
| 120 | 4840 | 4430 | 5200 | 5280 |
| 123 | 7210 | 6410 | 7210 | 7700 |
| 126 | 7290 | 5850 | 6880 | 7020 |
| 144 | 5170 | 4210 | 4920 | 5430 |
| 147 | 7430 | 6320 | 7490 | 7780 |
| 150 | 6920 | 6130 | 7630 | 7110 |
| 168 | 5750 | 4940 | 5730 | 5670 |

The PK parameters of R5000 following multiple dose SC administration (0.2 mg/kg/day) for 7-days are presented in the following Table. The pharmacokinetic (PK) parameters measured include clearance (CL), $C_{max}$ (maximum plasma drug concentration), $T_{max}$ (time taken to reach maximum plasma concentration following drug administration), $t_{1/2}$ (half-life), $AUC_{tau}$ (area under the plasma concentration-time curve from time zero to 24 hours), $AUC_{0-inf}$ (area under the plasma concentration-time curve from time zero to infinity), $V_z/F$ (apparent volume of distribution), $K_{el}$ (elimination rate), and F (fractions).

TABLE 13

Summary of PK parameters

| PK Parameter | Statistic | R5000 (0.20 mg/kg) (N = 4) | |
|---|---|---|---|
| | | Day 1 | Day 7 |
| Cmax | Mean | 2533 | 7290 |
| (ng/mL) | (SD) | (100.1) | (662.4) |
| $T_{max}$ | Median | 3 | 3 |
| (h) | (min, max) | (3, 6) | (3, 6) |
| $AUC_{tau}$ | Mean | 50010 | 151300 |
| (ng * h/mL) | (SD) | (3334.0) | (12042) |
| AUC0-inf | Mean | NC | 1101000 |
| (ng * h/mL) | (SD) | | (108220) |
| $t_{1/2}$ | Mean | NC | 161.9 |
| (h) | (SD) | | (14.8) |
| $K_{el}$ (1/h) | Mean | NC | 0.004309 |
| | (SD) | | (0.00041325) |
| CL/F | Mean | NC | 1.330 |
| (mL/h/kg) | (SD) | | (0.114) |
| $V_z/F$ | Mean | NC | 311.6 |
| (mL/kg) | (SD) | | (51.4) |

The day 1 mean $C_{max}$ and $AUC_{tau}$ were 2533 ng/mL and 50,010 ng*h/mL respectively, consistent with results from the 0.2 mg/kg single-dose cohort over the same post-dose period. Following daily SC administration for 7 days, the $C_{max}$ and $AUC_{tau}$ increased by approximately 2.9-fold (mean day 7 $C_{max}$=7290 ng/mL) and 3.0-fold (mean day 7 $AUC_{tau}$=151,300 ng*h/mL) respectively. The median time to maximum plasma concentration ($T_{max}$) on day 7 was 3.0 hours, which was consistent with the $T_{max}$ following single dose SC administration (median day 1 $T_{max}$=3.0-4.6 hours). This indicates a consistent rate of R5000 absorption with repeat dosing. The mean day 7 apparent total body clearance of R5000 (day 7 CL/F=1.3 mL/h/kg) was slightly increased relative to the total body clearance following a single SC dose at 0.2 mg/kg [single ascending dose (SAD) 0.2 mg/kg CL/F=0.29 mL/h/kg]. However, the elimination rate constant ($K_{el}$) for R5000 was consistent following single and repeat dosing (0.2 mg/kg SAD mean $K_{el}$=0.0041 h$^{-1}$; 0.2 mg/kg MD mean day 7 $K_{el}$=0.0043 h$^{-1}$) indicating that the clearance of R5000 does not change significantly with repeat dosing. The apparent volume of distribution of R5000 ($V_z/F$) showed some increase with administration of multiple doses of R5000 (0.2 mg/kg SAD mean $V_z/F$=71.4 mL/kg; 0.2 mg/kg MD mean day 7 $V_z/F$=311.6 mL/kg). However, the day 7 $V_z/F$ for R5000 was still less than total body water suggesting that R5000 does not distribute into the extravascular space upon repeat SC administration.

TABLE 14

Hemolysis analysis

| Time Point | % Hemolysis (treated) | | | | % Hemolysis (placebo) | |
|---|---|---|---|---|---|---|
| (hrs) | Subject 1 | Subject 2 | Subject 3 | Subject 4 | Subject 5 | Subject 6 |
| 0 | 100.0 | 100.0 | 100.0 | 100.0 | 100.0 | 100.0 |
| 3 | 5.8 | 1.9 | 5.0 | 2.9 | 99.4 | 102.7 |
| 6 | 6.0 | 1.6 | 5.2 | 2.3 | 90.8 | 99.4 |
| 24 | 9.3 | 2.4 | 8.9 | 2.9 | 105.8 | 100.7 |

TABLE 14-continued

Hemolysis analysis

| Time Point | % Hemolysis (treated) | | | | % Hemolysis (placebo) | |
|---|---|---|---|---|---|---|
| (hrs) | Subject 1 | Subject 2 | Subject 3 | Subject 4 | Subject 5 | Subject 6 |
| 27 | 4.9 | 1.2 | 4.0 | 1.0 | 112.3 | 96.1 |
| 30 | 4.6 | 1.5 | 4.6 | 2.2 | 110.5 | 100.6 |
| 48 | 6.6 | 2.0 | 6.9 | 2.1 | 120.6 | 107.2 |
| 51 | 4.0 | 1.4 | 3.6 | 1.9 | 118.4 | 97.3 |
| 54 | 3.7 | 1.4 | 3.6 | 1.8 | 133.5 | 98.0 |
| 72 | 5.0 | 1.6 | 3.8 | 1.7 | 114.4 | 97.9 |
| 75 | 2.9 | 0.8 | 2.7 | 1.3 | 121.4 | 98.2 |
| 78 | 3.0 | 0.9 | 4.7 | 1.5 | 119.4 | 94.6 |
| 96 | 3.9 | 1.1 | 4.0 | 6.5 | 111.5 | 95.2 |
| 99 | 2.9 | 0.9 | 2.7 | 1.0 | 122.0 | 101.1 |
| 102 | 3.6 | 1.4 | 3.8 | 1.7 | 135.1 | 101.4 |
| 120 | 4.0 | 2.1 | 3.8 | 2.3 | 115.4 | 95.7 |
| 123 | 2.7 | 1.3 | 2.7 | 1.6 | 114.1 | 92.2 |
| 126 | 3.3 | 1.3 | 3.2 | 1.3 | 113.5 | 96.9 |
| 144 | 3.4 | 1.2 | 3.8 | 1.4 | 108.8 | 95.7 |
| 147 | 2.5 | 1.2 | 2.6 | 1.2 | 121.7 | 103.7 |
| 150 | 3.4 | 1.3 | 3.0 | 1.4 | 121.3 | 98.3 |
| 168 | 3.4 | 1.5 | 3.1 | 1.8 | 119.1 | 102.0 |

Mean percent inhibition of hemolysis compared to baseline reached ≥95% beginning at the first time point following dosing, 3 hours after dosing on Day 1, and continued throughout the 7 days of dosing (see the following Table). All individual subjects showed ≥90% reduction of hemolysis at all time points. Hemolysis at day 8 (24 hours after receiving the last dose) was observed to be ≤3% in all subjects. Hemolysis returned to pre-dose levels within two weeks following the last dose.

The study suggests that low daily doses will achieve steady-state levels suitable for complete and sustained inhibition of complement and suppression of hemolysis. The study also suggests that once-weekly dosing may be sufficient to inhibit complement activity and reduce hemolysis in humans.

Figure 10A:
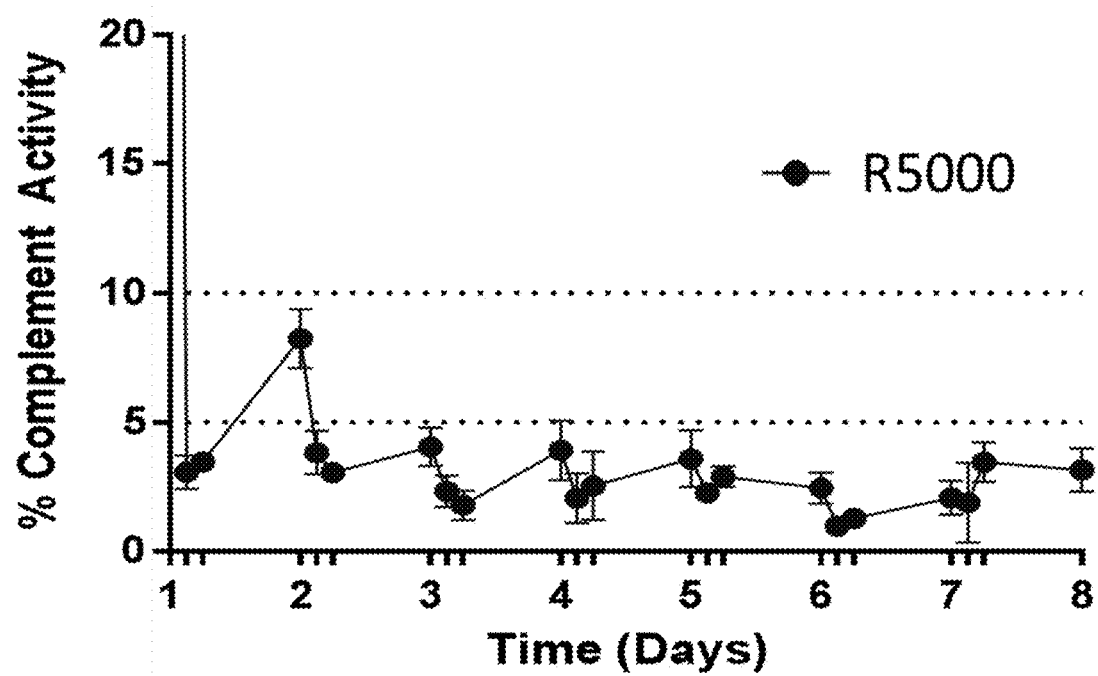
FIG. 10A is a graph showing changes in complement activity over time with R5000 treatment in a multi-dose human study.

Complement activity in subject plasma samples was determined by WIESLAB® ELISA (Euro Diagnostica, Malmo, Sweden) analysis. This assay measures the alternative pathway of complement activation. As measured via this assay, suppression of complement activity was rapid, complete, and sustained across the dosing period in all subjects (see FIG. 10A and the following Table). In the following Table, SEM indicates standard error of mean.

TABLE 15

% complement activity in multiple dose study

| | Hours after first treatment | | |
|---|---|---|---|
| | 3 | 48 | 96 |
| Minimum % complement activity (SEM) | 1.8 (0.8) | 6.9 (0.3) | 2.1 (0.1) |
| Average % complement activity (SEM) | 3.1 (0.6) | 8.2 (1.1) | 3.1 (0.8) |

Figure 10B:
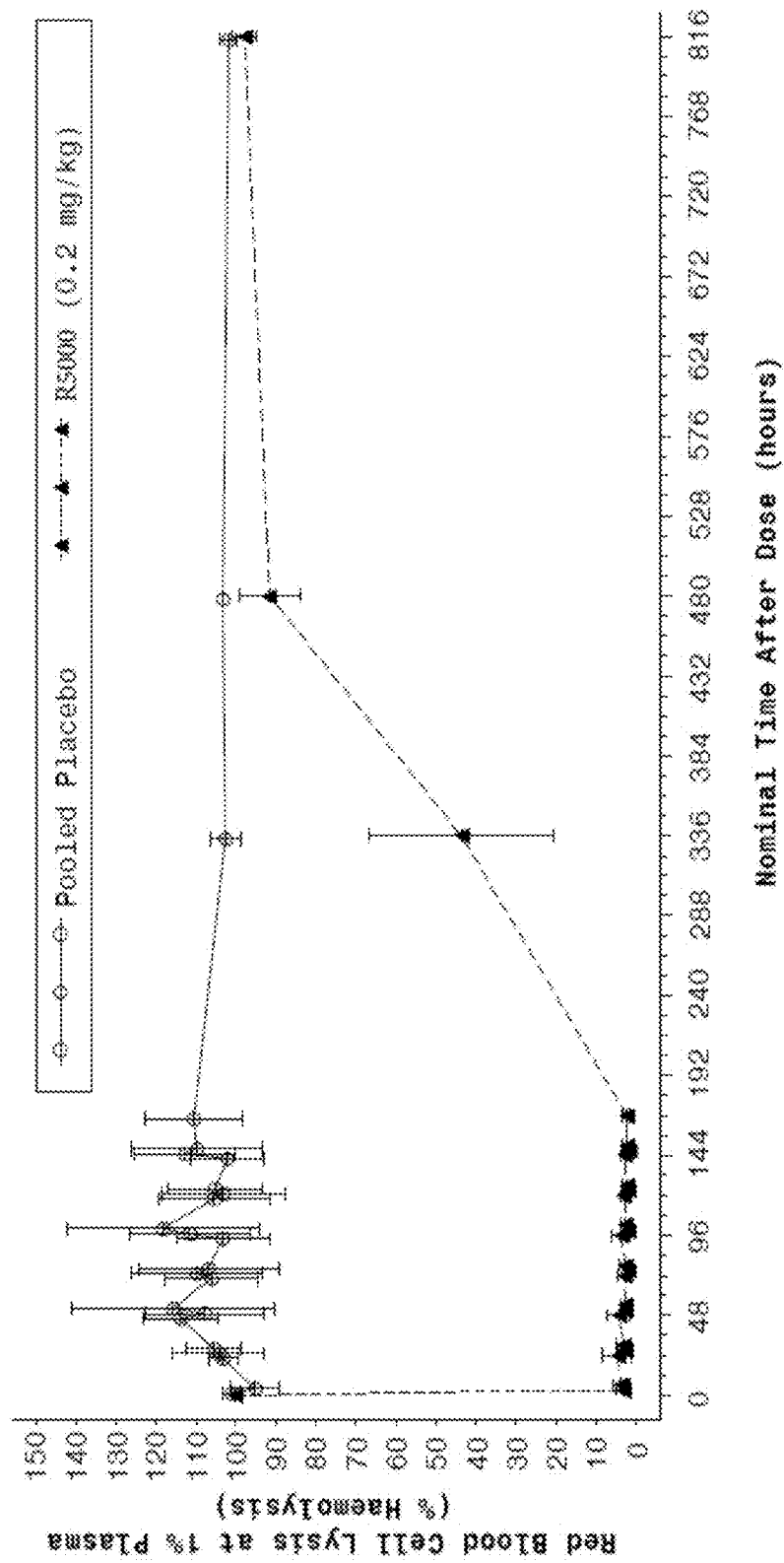
FIG. 10B is a graph showing changes in complement activity over an extended period with R5000 treatment in a multi-dose human study.

Complement activity at day 8 (24 hours after the last dose) was observed to be ≤5% in all subjects. Complement activity returned to pre-dose levels within two weeks following the last dose (FIG. 10B).

R5000 was safe and well-tolerated in healthy volunteers with the exception of some injection site erythema (ISE) in 3 out of 6 subject, but with no pain, induration, tenderness or swelling. All resolved spontaneously. No clinically significant changes were observed in vital signs, clinical laboratory parameters (hematology, blood chemistry, coagulation, and urinalysis), physical exams and ECGs.

R5000 was measured in the 0.20 mg/kg dose group of the multi-dose arm of the study (see the following Table). In the following Table, $C_{max}$ refers to maximum plasma drug concentration, and $AUC_{0-24}$ refers to area under the plasma concentration-time curve from time zero to 24 hours.

TABLE 16

Mean exposure of R5000

| Compound | $C_{max}$ (ng/mL) | $AUC_{0-24}$ (ng * h/mL) |
|---|---|---|
| R5000 | 7255 | 151815 |

Example 15. Phase 1 Single-Ascending-Dose Clinical Study of R5000

A Phase 1 single-ascending-dose clinical pharmacology study in healthy human volunteers designed to evaluate the safety, tolerability, pharmacokinetics and pharmacodynamics of R5000 following subcutaneous (SC) injection was carried out. The study was randomized, double-blinded, and placebo (PBO)-controlled with 4 SC single-ascending-dose cohorts housed in a clinical pharmacology unit for 3 days. All subjects received 1 dose of R5000 on Day 1. Four subjects (2 receiving R5000 and 2 receiving PBO) were administered the lowest dose level (0.05 mg/kg) and 6 subjects per cohort (4 receiving R5000 and 2 receiving PBO) were sequentially administered the 3 higher dose levels (0.1, 0.2, and 0.4 mg/kg). Subject demographic information is provided in the following Table.

TABLE 17

| Subject demographics | | | | | | |
|---|---|---|---|---|---|---|
| | Placebo treated, n = 8 | R5000 treated, 0.05 mg/kg, n = 2 | R5000 treated, 0.1 mg/kg, n = 4 | R5000 treated, 0.2 mg/kg, n = 4 | R5000 treated, 0.4 mg/kg, n = 4 | All, n = 22 |
| Male:Female ratio | 2:6 | 0:2 | 0:4 | 0:4 | 1:3 | 3:19 |
| Mean Age, years (min, max) | 39 (20, 59) | 23 (22, 23) | 27 (20, 37) | 34 (22, 65) | 32 (21, 58) | 33 (20, 65) |
| Mean body mass index, kg/m2 | 24 | 20 | 21 | 26 | 27 | 24 |
| White:Black:Asian | 7:1:0 | 2:0:0 | 2:1:1 | 3:0:1 | 4:0:0 | 18:2:2 |

Safety was assessed by intensive clinical monitoring, and frequent blood samples were obtained for determination of R5000 concentrations by liquid chromatography/high resolution mass spectroscopy and ability to inhibit complement-mediated RBC lysis in an ex vivo antibody-sensitized sheep erythrocyte hemolysis assay.

Figure 11A:
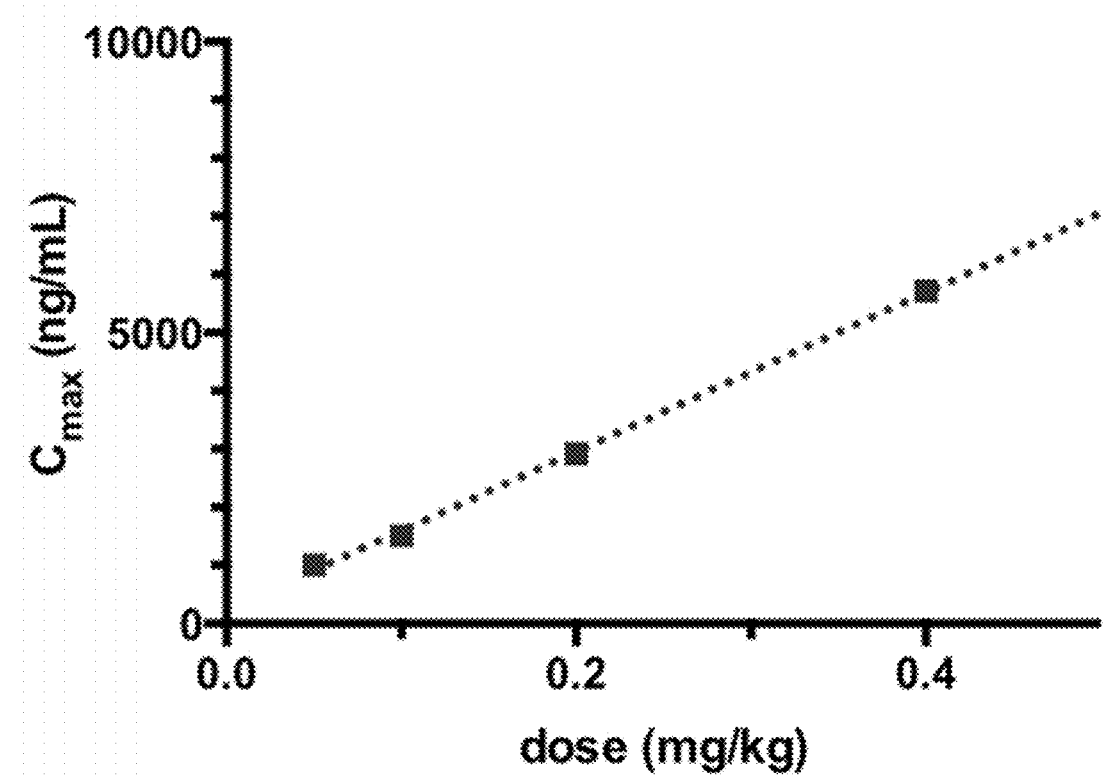
FIG. 11A is a graph showing R5000 dose-dependent maximum plasma concentration levels in a single-ascending-dose clinical study in humans.

The pharmacokinetic (PK) parameters measured in this study include clearance (CL), $C_{max}$ (maximum plasma drug concentration, FIG. 11A), $T_{max}$ (time taken to reach maximum plasma concentration following drug administration), $t_{1/2}$ (half-life), $AUC_{0-24}$ (area under the plasma concentration-time curve from time zero to 24 hours; see FIG. 11B for plasma concentration over time), $AUC_{0-inf}$ (area under the plasma concentration-time curve from time zero to infinity; see FIG. 11B for plasma concentration over time), $V_z$ (apparent volume of distribution during terminal phase), K (elimination rate), and F (fractions). Results for each parameter are presented in the following Table.

across doses. These results indicate that with increasing R5000 dose, there is an approximately proportional increase in plasma concentration ($C_{max}$) and exposure ($AUC_{0-24}$). The median time to maximum observed plasma concentration ($t_{max}$) ranged from 3.0 to 4.6 hours across doses indicating R5000 exhibits an intermediate rate of absorption from the SC space to the central (blood) compartment. The mean apparent total body clearance (CL/F) after R5000 administration was low and ranged from 0.2481 to 0.4711 mL/h/kg. The mean half-life ($t_{1/2}$) was consistent across dose levels and ranged from 155.6 to 185.4 hours. The mean apparent total volume of distribution ($V_z$/F) at the terminal phase after extravascular administration ranged from 61.89 to 105.1 mL/kg which indicates R5000 is localized primarily in the circulating blood compartment with minimal extravascular distribution. The approximate $t_{1/2}$ across all cohorts was determined to be 7 days.

TABLE 18

| Pharmacokinetic parameters | | | | | |
|---|---|---|---|---|---|
| PK Parameter | Statistic | R5000 (0.05 mg/kg) N = 2 | R5000 (0.10 mg/kg) N = 4 | R5000 (0.20 mg/kg) N = 4 | R5000 (0.40 mg/kg) N = 4 |
| $C_{max}$ (ng/mL) | Mean (SD) | 1010 (14.142) | 1550 (197.82) | 2970 (317.80) | 5873 (440.71) |
| $T_{max}$ (h) | Median (min, max) | 4.5 (3, 6) | 3.0 (3, 24) | 4.5 (3, 48) | 4.6 (3, 6) |
| $AUC_{0-24}$ (ng * h/mL) | Mean (SD) | 21440 (1020.9) | 33230 (4605.6) | 60350 (4624.8) | 112300 (8623.2) |
| $AUC_{0-last}$ (ng * h/mL) | Mean (SD) | 179800 (3214.7) | 375400 (47513) | 655100 (113710) | 822600 (120760) |
| $AUC_{0-inf}$ (ng * h/mL) | Mean (SD) | 190700 (3081.0) | 408600 (52716) | 702900 (143630) | 863200 (134870) |
| $t_{1/2}$ (h) | Mean (SD) | 163.5 (10.9) | 185.4 (6.4) | 172.0 (24.8) | 155.6 (14.3) |
| $K_{el}$ (1/h) | Mean (SD) | 0.004248 (0.000283) | 0.003743 (0.000128) | 0.004092 (0.00058001) | 0.004482 (0.00041984) |
| CL/F (mL/h/kg) | Mean (SD) | 0.2622 (0.0042) | 0.2481 (0.0353) | 0.2933 (0.0574) | 0.4711 (0.0660) |
| $V_z$/F (mL/kg) | Mean (SD) | 61.89 (5.13) | 66.41 (10.20) | 71.43 (7.52) | 105.10 (11.68) |

Figure 12A:
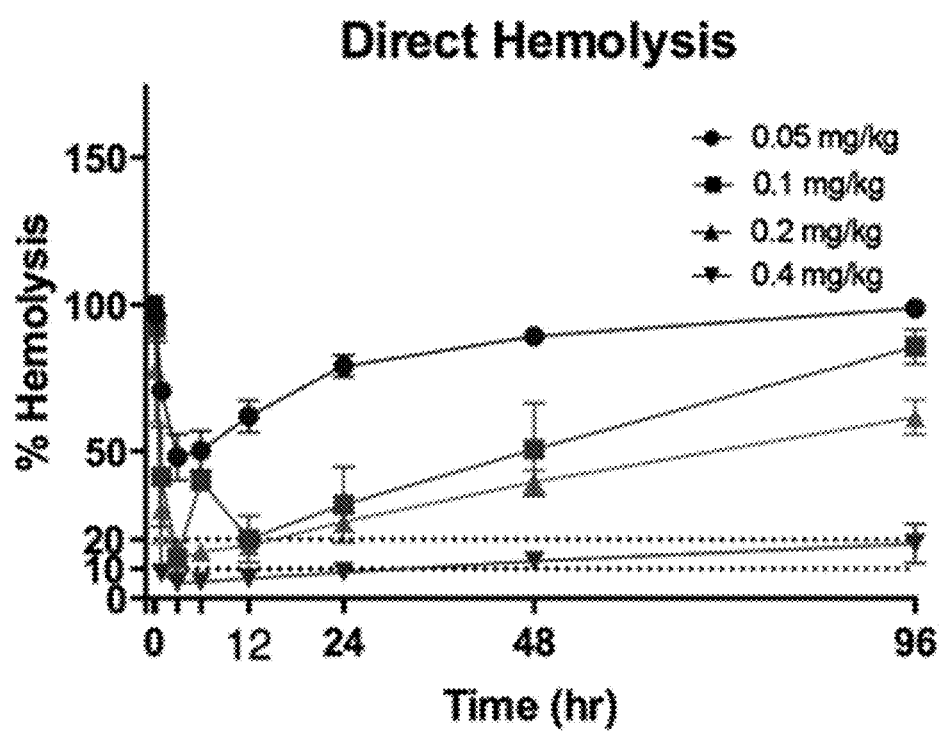
FIG. 12A is a graph showing percent hemolysis over time after single dose administration of R5000 over the duration of 4 days in humans.
Figure 12B:
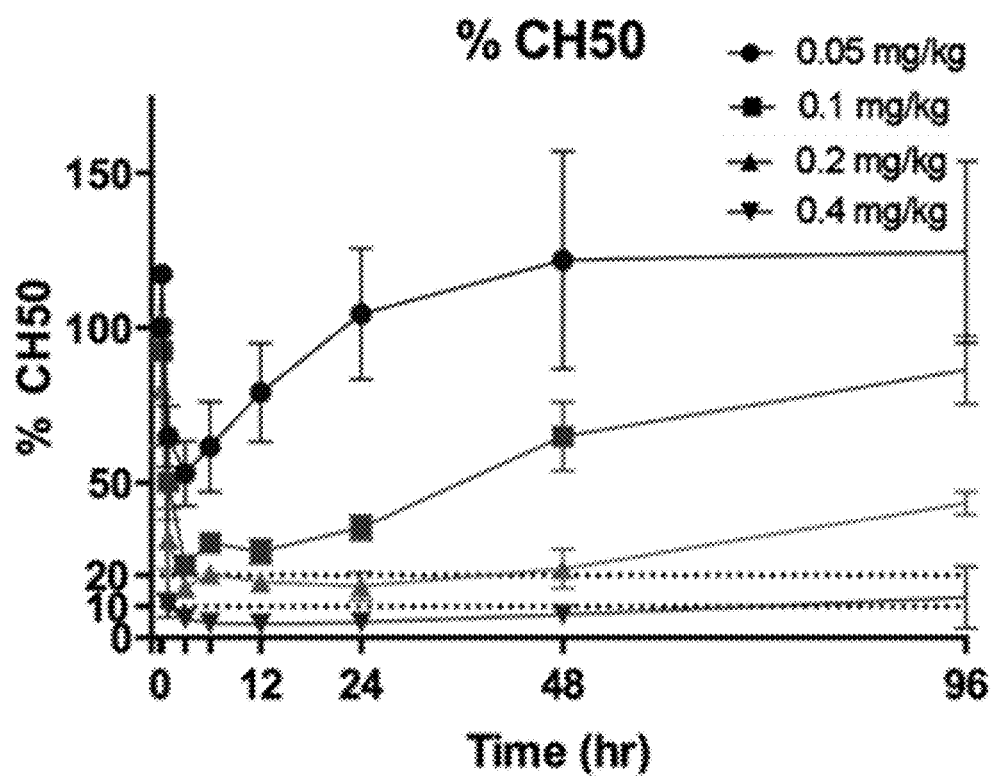
FIG. 12B is a graph showing percent $CH_{50}$ over time after single dose administration of R5000 in humans.
Figure 12C:
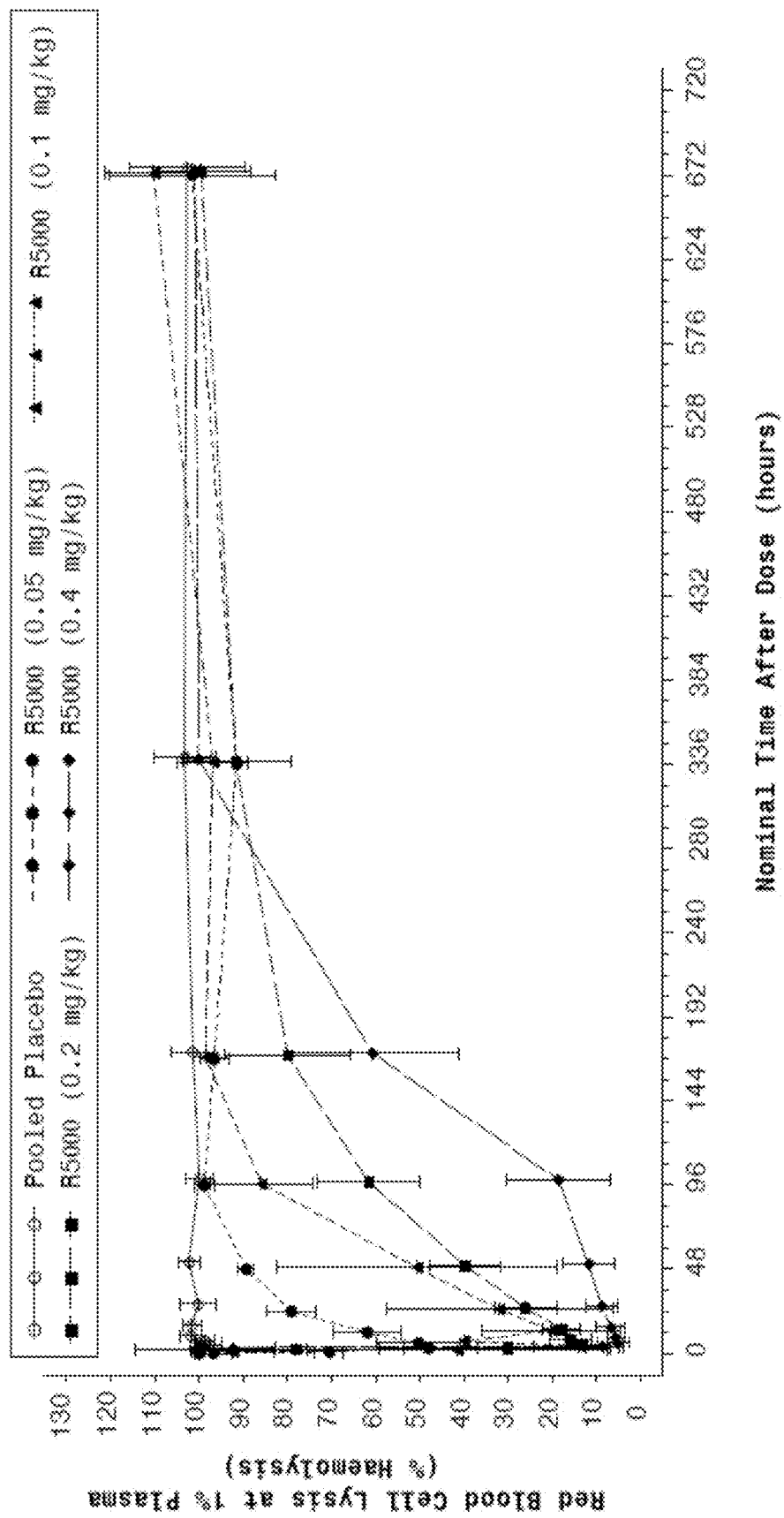
FIG. 12C is a graph showing percent hemolysis with various doses over the duration of 28 days in humans.

All cohorts achieved $C_{max}$ levels consistent with predicted values from an in silico PK model generated using data from non-human primate (NHP) studies. Plasma concentrations of a single SC injection showed a linear relationship between $C_{max}$ and dose level (FIG. 11A) and dose-dependent exposure across all dose levels was confirmed (FIG. 11B). The mean maximum plasma concentration ($C_{max}$) ranged from 1010 to 5873 ng/mL across doses. The mean area under the concentration-time curve from time 0 to 24 hours post dose ($AUC_{0-24}$) ranged from 21,440 to 112,300 ng*h/mL R5000 also exhibited a rapid dose-dependent inhibition of hemolysis [direct hemolysis (FIG. 12A) and % $CH_{50}$ (FIG. 12B) and red blood cell lysis at 1% plasma over time (FIG. 12C)] and suppression of complement activity (as determined by WIESLAB® ELISA in all subjects after a single dose, see FIG. 13). The maximum pharmacodynamics effect was observed approximately 3 hours after dosing. Results demonstrated that at the maximum plasma concentration, the maximal percent inhibition of hemolysis compared to baseline reached >90% for the 0.1, 0.2, and 0.4 mg/kg dose cohorts and 60% for the lowest dose (0.05 mg/kg) cohort. Dose-dependent inhibition of hemolysis of up to 4 days was observed for the 0.1, 0.2, and 0.4 mg/kg dose cohorts. Notably, mean hemolysis remained above baseline for up to 2 days in the 0.05 mg/kg cohort, up to 4 days in the 0.1 mg/kg cohort, and for up to 7 days in the 0.2 and 0.4 mg/kg cohorts.

Figure 13:
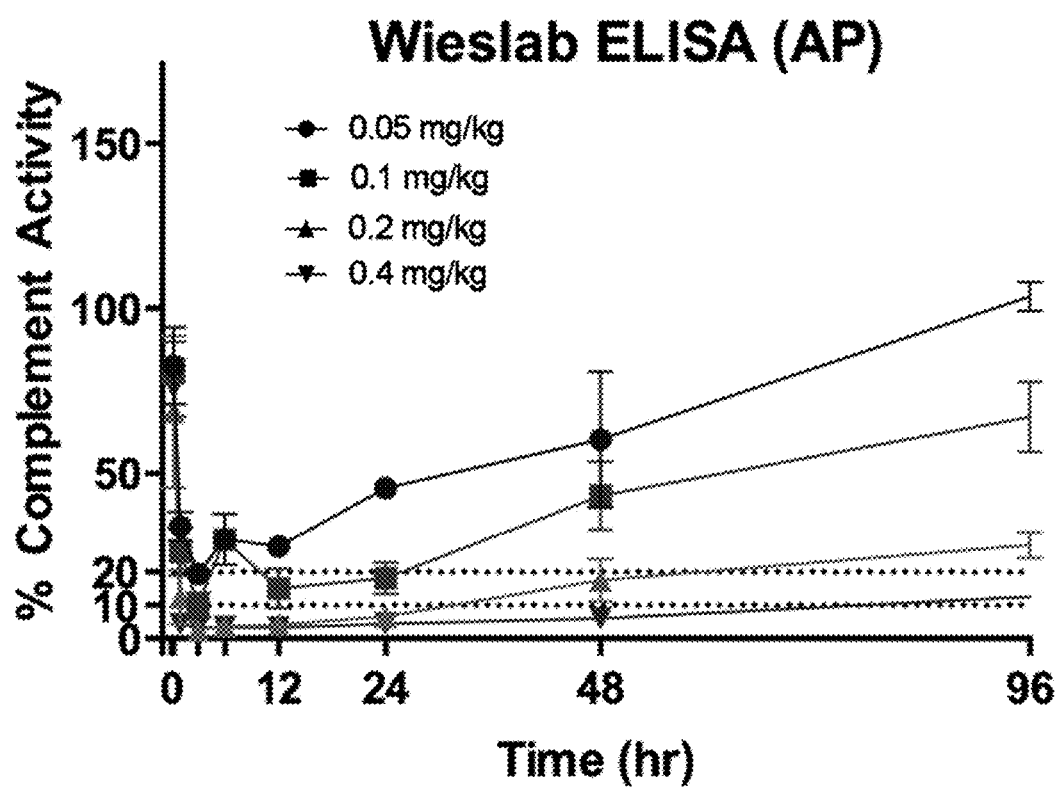
FIG. 13 is a graph showing percent complement activity over time after a single dose administration of R5000 in humans.

Similarly, analysis of complement activity demonstrated that inhibition of complement activity remained strong over the course of 4 days following the 0.4 mg/kg injection (see FIG. 13). Human plasma samples taken from subjects receiving 0.4 mg/kg injection were subjected to WIESLAB® ELISA (Euro Diagnostica, Malmo, Sweden) analysis. This assay measures the alternative pathway of complement activity. As measured via this assay, complement activity was suppressed to 3% at 3 hours following dosing and remained below 13% 96 hours after receiving R5000.

Single SC doses of R5000 were safe and well tolerated in healthy volunteers. ISE was observed in 3 subjects at the highest dose and was mild (grade 1) with no pain, induration, tenderness, or swelling and resolved spontaneously within 2-5 hours post-injection. No clinically significant changes were observed in vital signs, clinical laboratory parameters, physical exams, and ECGs.

This study suggests that low daily doses may achieve steady-state levels suitable for >80% suppression of hemolysis and that once-weekly dosing may be sufficient. Specifically, 0.2 mg/kg may result in full suppression of complement activity and complete inhibition of hemolysis.

What is claimed is:

1. A pharmaceutical composition comprising
a C5 inhibitor polypeptide comprising the core amino acid sequence of SEQ ID NO: 1;
a salt; and
a buffering agent.

2. The pharmaceutical composition of claim 1, wherein the salt comprises sodium chloride.

3. The pharmaceutical composition of claim 1, wherein the salt is present at a concentration of from about 25 mM to about 100 mM.

4. The pharmaceutical composition of claim 1, wherein the buffering agent comprises sodium phosphate.

5. The pharmaceutical composition of claim 1, wherein the buffering agent is present at a concentration of from about 10 mM to about 100 mM.

6. The pharmaceutical composition of claim 1 comprising a pH of from about 6.5 to 7.5.

7. The pharmaceutical composition of claim 1, wherein the polypeptide is present at a concentration of from about 1 mg/mL to about 400 mg/mL.

8. The pharmaceutical composition of claim 7, wherein the polypeptide binds to C5 with an equilibrium dissociation constant ($K_D$) of from about 0.1 nM to about 1 nM.

9. The pharmaceutical composition of claim 8, wherein the polypeptide blocks production of C5a following activation of the alternative pathway of complement activation.

10. The pharmaceutical composition of claim 8, wherein the polypeptide blocks formation of the membrane attack complex (MAC) following activation of the classical pathway, alternative pathway, or lectin pathway of complement activation.

11. The pharmaceutical composition of claim 1, wherein the polypeptide is present at a concentration of about 40 mg/mL.

12. The pharmaceutical composition of claim 1, wherein the pharmaceutical composition comprises about 75.7 mM sodium chloride.

13. The pharmaceutical composition of claim 1, wherein the pharmaceutical composition comprises about 50 mM sodium phosphate.

14. A method of treating a complement-related disorder in a subject, the method comprising providing the pharmaceutical composition of claim 1 to the subject.

15. The method of claim 14, wherein the pharmaceutical composition is administered subcutaneously (SC) or intravenously (IV) to the subject.

16. The method of claim 14, wherein the subject is vaccinated against *Neisseria meningitides*.

17. The method of claim 14, wherein the subject is coadministered eculizumab, cyclosporin, and/or an antibiotic.

18. An auto-injector device comprising the pharmaceutical composition of claim 1.

* * * * *